United States Patent
Gotoh et al.

(10) Patent No.: US 10,053,425 B2
(45) Date of Patent: *Aug. 21, 2018

(54) PIPERIDINE DERIVATIVE, LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Ichihara-shi, Chiba (JP)

(72) Inventors: Yasuyuki Gotoh, Tokyo (JP); Kenji Hirata, Chiba (JP); Maiko Matsukuma, Chiba (JP); Chikahide Kanadani, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/034,809

(22) PCT Filed: Oct. 29, 2014

(86) PCT No.: PCT/JP2014/078687
§ 371 (c)(1),
(2) Date: May 5, 2016

(87) PCT Pub. No.: WO2015/076077
PCT Pub. Date: May 28, 2015

(65) Prior Publication Data
US 2016/0289189 A1 Oct. 6, 2016

(30) Foreign Application Priority Data
Nov. 19, 2013 (JP) .................. 2013-239021

(51) Int. Cl.
G02F 1/1333 (2006.01)
C07D 211/12 (2006.01)
C07D 211/22 (2006.01)
C07D 211/26 (2006.01)
C09K 19/42 (2006.01)
(Continued)

(52) U.S. Cl.
CPC .......... *C07D 211/12* (2013.01); *C07D 211/18* (2013.01); *C07D 211/22* (2013.01); *C07D 211/26* (2013.01); *C07D 239/26* (2013.01); *C07D 317/16* (2013.01); *C07D 405/14* (2013.01); *C09K 19/3068* (2013.01); *C09K 19/3402* (2013.01); *C09K 19/3483* (2013.01); *C09K 19/42* (2013.01); *C09K 19/44* (2013.01); *C09K 19/54* (2013.01); *C09K 2019/0466* (2013.01); *C09K 2019/122* (2013.01); *C09K 2019/123* (2013.01); *C09K 2019/3019* (2013.01); *C09K 2019/3071* (2013.01); *C09K 2019/3422* (2013.01)

(58) Field of Classification Search
CPC .... C09K 19/42; C09K 19/54; C09K 19/3483; C09K 19/44; C09K 19/3068; C09K 19/3402; C09K 2019/0466; C09K 2019/122; C09K 2019/123; C09K 2019/3019; C09K 2019/3071; C09K 2019/3422; C07D 211/12; C07D 211/22; C07D 211/26; C07D 211/18; C07D 317/16; C07D 239/26; C07D 405/14; G02F 1/1333
USPC ........................................ 252/299.6; 428/1.1
See application file for complete search history.

(56) References Cited

U.S. PATENT DOCUMENTS 4,166,814 A    9/1979  Karrer
5,198,546 A    3/1993  Borzatta et al.
(Continued)

FOREIGN PATENT DOCUMENTS

JP    H9-291282    11/1997
WO    02/18515     3/2002

OTHER PUBLICATIONS

International Search Report dated Dec. 16, 2014 in corresponding PCT application No. PCT/JP2014/078687.

*Primary Examiner* — Geraldina Visconti
(74) *Attorney, Agent, or Firm* — Hogan Lovells US LLP

(57) ABSTRACT

To provide a compound having an effect for preventing photolysis of a liquid crystal composition, and having a high solubility in the liquid crystal composition, a liquid crystal composition containing the compound, and a liquid crystal display device including the composition. The compound is represented by formula (1), the liquid crystal composition contains the compound, and the liquid crystal display device includes the composition.

(1)

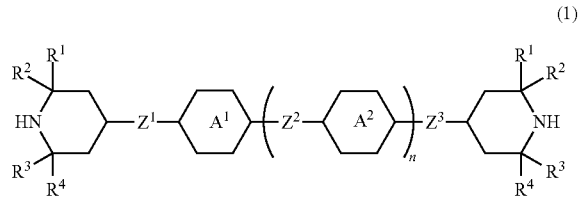

In formula (1), $R^1$, $R^2$, $R^3$ and $R^4$ are independently hydrogen or alkyl having 1 to 4 carbons; ring $A^1$ and ring $A^2$ are independently 1,4-cyclohexylene, 1,4-phenylene or the like; $Z^1$, $Z^2$ and $Z^3$ are independently a single bond, alkylene or the like; and n is 0, 1 or 2.

11 Claims, No Drawings

(51) Int. Cl.
*C09K 19/54* (2006.01)
*C09K 19/34* (2006.01)
*C09K 19/44* (2006.01)
*C07D 317/16* (2006.01)
*C07D 239/26* (2006.01)
*C07D 211/18* (2006.01)
*C07D 405/14* (2006.01)
*C09K 19/04* (2006.01)
*C09K 19/12* (2006.01)
*C09K 19/30* (2006.01)

(56) References Cited

U.S. PATENT DOCUMENTS

| | | | |
|---|---|---|---|
| 6,958,176 B2 * | 10/2005 | Li | C07D 211/46 252/299.01 |
| 2003/0127627 A1 | 7/2003 | Amakawa | |
| 2007/0108411 A1 | 5/2007 | Saito et al. | |
| 2012/0268706 A1 | 10/2012 | Goebel | |
| 2016/0376505 A1 * | 12/2016 | Furusato | C09K 19/3483 252/299.4 |

* cited by examiner

PIPERIDINE DERIVATIVE, LIQUID CRYSTAL COMPOSITION AND LIQUID CRYSTAL DISPLAY DEVICE

RELATED APPLICATIONS

This application is a U.S. National Phase under 35 U.S.C. § 371 of International Application PCT Patent Application No. PCT/JP2014/078687, filed on Oct. 29, 2014, which claims priority to Japanese Patent Application No. 2013-239021, filed on Nov. 19, 2013; the contents of which are all herein incorporated by this reference in their entireties. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The present invention relates to a piperidine derivative, a liquid crystal composition and a liquid crystal display device. More specifically, the invention relates to a 2,2,6,6-tetramethylpiperidine derivative, a liquid crystal composition that contains the compound and has a positive dielectric anisotropy, and a liquid crystal display device including the composition.

The liquid crystal display device is widely used for a display of a personal computer, a television and so forth. The device uses optical anisotropy, dielectric anisotropy and so forth of a liquid crystal compound. An operating mode for the liquid crystal display device includes a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a vertical alignment (VA) mode, a fringe field switching (FFS) mode and a polymer sustained alignment (PSA) mode.

In the liquid crystal display device, the liquid crystal composition having suitable physical properties is used. In order to further improve characteristics of the liquid crystal display device, the liquid crystal compound contained in the composition preferably has the physical properties described in (1) to (8) below.

(1) High stability to heat, light and so forth
(2) High clearing point
(3) Low minimum temperature of a liquid crystal phase
(4) Small viscosity ($\eta$)
(5) Suitable optical anisotropy ($\Delta n$)
(6) Large dielectric anisotropy ($\Delta \varepsilon$)
(7) Suitable elastic constant (K)
(8) Excellent compatibility with other liquid crystal compounds An effect of the physical properties of the liquid crystal compound on the characteristics of the device is as described below. A compound having the high stability to heat, light and so forth as described in (1) increases a voltage holding ratio of the device. Accordingly, a service life of the device is elongated. A compound having the high clearing point as described in (2) extends a temperature range in which the device can be used. A compound having the low minimum temperature of the liquid crystal phase, such as a nematic phase and a smectic phase as described in (3), particularly a compound having the low minimum temperature of the nematic phase also extends the temperature range in which the device can be used. A compound having the small viscosity as described in (4) shortens a response time of the device.

A compound having the suitable optical anisotropy as described in (5) improves a contrast of the device. According to a design of the device, a compound having a large optical anisotropy or a small optical anisotropy namely, the compound having the suitable optical anisotropy is required. When the response time is shortened by decreasing a cell gap of the device, a compound having the large optical anisotropy is suitable. A compound having the large dielectric anisotropy as described in (6) decreases a threshold voltage of the device. Accordingly, power consumption of the device becomes small. On the other hand, a compound having the small dielectric anisotropy shortens the response time of the device by reducing the viscosity of the composition.

A compound having a large elastic constant as described in (7) shortens the response time of the device. A compound having a small elastic constant decreases the threshold voltage of the device. Therefore, the suitable elastic constant is required according to the characteristics to be desirably improved. A compound having the excellent compatibility with other liquid crystal compounds as described in (8) is preferred. The reason is that the liquid crystal compounds having different physical properties are mixed to adjust the physical properties of the composition.

The liquid crystal composition is prepared by selecting the liquid crystal compounds having at least one of the physical properties described in (1) to (8) and mixing the compounds. An additive such as a polymerizable compound, a polymerization initiator, a polymerization inhibitor, an optically active compound, an antioxidant, an ultraviolet light absorber, a light stabilizer, a heat stabilizer and an antifoaming agent is added to the composition, when necessary. Among the additives, the light stabilizer is effective in preventing the liquid crystal compound from being decomposed by light from backlight or the sun. A high voltage holding ratio in the device is maintained by the effect described above, and therefore the service life of the device is elongated. A hindered amine light stabilizer (HALS) is suitable for such a purpose. However, development of a superb light stabilizer has been expected.

CITATION LIST

Patent Literature

Patent literature No. 1: JP H9-291282 A.
Patent literature No. 2: JP 2003-226876 A.
Patent literature No. 3: JP 2004-507607 A.
Patent literature No. 4: JP 2012-224632 A.

SUMMARY OF INVENTION

Technical Problem

A first object of the invention is to provide a compound having an effect of preventing photolysis of a liquid crystal composition, and having a high solubility in the liquid crystal composition. A second object is to provide a liquid crystal composition that contains the compound and satisfies at least one of characteristics such as a high maximum temperature of a nematic phase, a low minimum temperature of the nematic phase, a small viscosity, a suitable optical anisotropy, a large dielectric anisotropy, a large specific resistance, a high stability to ultraviolet light, a high stability to heat and a large elastic constant. The object is also to provide a liquid crystal composition having stability to light. A third object is to provide a liquid crystal display device that includes the composition and has a wide temperature range in which the device can be used, a short response time, a high voltage holding ratio, a low threshold voltage, a large contrast ratio and a long service life.

Solution to Problem

The invention concerns a compound represented by formula (1), a liquid crystal composition containing the compound and a liquid crystal display device including the composition.

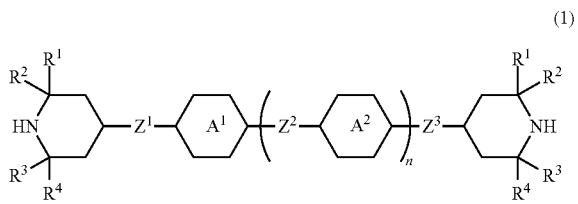

In formula (1), $R^1$, $R^2$, $R^3$, and $R^4$ are independently hydrogen or alkyl having 1 to 4 carbons; ring $A^1$ and ring $A^2$ are independently 1,4-cyclohexylene, 1,4-cyclohexenylene, 1,2-phenylene, 1,3-phenylene, 1,4-phenylene, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, decahydronaphthalene-2,6-diyl, dihydropyrane-2,5-diyl, tetrahydropyran-2,5-diyl, 1,3-dioxane-2,5-diyl, pyrimidine-2,5-diyl or pyridine-2,5-diyl, and in the rings, at least one piece of hydrogen may be replaced by halogen, alkyl having 1 to 5 carbons, alkoxy having 1 to 5 carbons, or alkyl having 1 to 5 carbons in which at least one piece of hydrogen is replaced by halogen; $Z^1$, $Z^2$ and $Z^3$ are independently a single bond or alkylene having 1 to 10 carbons, and in the alkylene, at least one piece of —$CH_2$— may be replaced by —O— and at least one piece of —$CH_2$—$CH_2$— may be replaced by —CH=CH— or —C≡C—, and in the groups, at least one piece of hydrogen may be replaced by fluorine; and n is 0, 1 or 2.

Advantageous Effects of Invention

A first advantage of the invention is a compound having an effect of preventing photolysis of a liquid crystal composition, and having a high solubility in the liquid crystal composition. A second advantage is also a liquid crystal composition that contains the compound and satisfies at least one of physical properties such as a high maximum temperature of a nematic phase, a low minimum temperature of the nematic phase, a small viscosity, a suitable optical anisotropy, a large dielectric anisotropy, a suitable elastic constant and a large specific resistance. The advantage is also to provide a liquid crystal composition having stability to light. A third advantage is to provide a liquid crystal display device that includes the composition and has a wide temperature range in which the device can be used, a short response time, a high voltage holding ratio, a low threshold voltage, a large contrast ratio and a long service life.

DESCRIPTION OF EMBODIMENTS

Usage of terms herein is as described below. "Liquid crystal compound" is a generic term for a compound having a liquid crystal phase such as a nematic phase and a smectic phase, and a compound having no liquid crystal phase but to be added for the purpose of adjusting characteristics of a composition, such as a maximum temperature, a minimum temperature, viscosity and dielectric anisotropy. The compounds have a 6-membered ring such as 1,4-cyclohexylene and 1,4-phenylene, and a rod-like molecular structure. A liquid crystal composition is prepared by mixing such liquid crystal compounds. A proportion (content) of the liquid crystal compounds is expressed in terms of weight percent (% by weight) based on the weight of the liquid crystal composition. An additive such as a polymerizable compound, a polymerization initiator, a polymerization inhibitor, an optically active compound, an antioxidant, an ultraviolet light absorber, a light stabilizer, a heat stabilizer and an antifoaming agent is added to the composition, when necessary. A proportion (amount of addition) of the additive is expressed in terms of weight percent (% by weight) based on the weight of the liquid crystal composition in a manner similar to the proportion of the liquid crystal compounds. Weight parts per million (ppm) may be occasionally used.

A liquid crystal display device is a generic term for a liquid crystal display panel and a liquid crystal display module. The liquid crystal compound, the liquid crystal composition and the liquid crystal display device may be occasionally abbreviated as "compound," "composition" and "device," respectively. A clearing point is a transition temperature between the liquid crystal phase and an isotropic phase in the liquid crystal compound. A minimum temperature of the liquid crystal phase is a transition temperature between a solid and the liquid crystal phase (the smectic phase, the nematic phase or the like) in the liquid crystal compound. A maximum temperature of the nematic phase is a transition temperature between the nematic phase and the isotropic phase in the liquid crystal composition, and may be occasionally abbreviated as the maximum temperature. A minimum temperature of the nematic phase may be occasionally abbreviated as the minimum temperature.

A compound represented by formula (1) may be occasionally abbreviated as compound (1). A same rule also applies to a compound represented by formula (2) or the like. In formulas (1) to (8), a symbol such as $A^1$, $B^1$, $C^1$ or the like surrounded by a hexagonal shape corresponds to ring $A^1$, ring $B^1$, ring $C^1$ or the like, respectively. A symbol of terminal group used for a plurality of compounds. In the compounds, two groups represented by two pieces of arbitrary $R^{11}$ may be identical or different. For example, in one case, $R^{11}$ of compound (2) is ethyl and $R^{11}$ of compound (3) is ethyl. In another case, $R^{11}$ of compound (2) is ethyl and $R^{11}$ of compound (3) is propyl. A same rule also applies to a symbol of any other terminal group, a ring, a bonding group or the like. In formula (8), when i is 2, two rings $D^1$ exist. In the compound, two groups represented by two rings D1 may be identical or different. A same rule also applies to two arbitrary rings $D^1$ when i is larger than 2. A same rule also applies to a symbol of any other ring, a bonding group or the like.

An expression in the context of "at least one piece of 'A' may be replaced by 'B'" means that, when the number of 'A' is one, a position of 'A' is arbitrary, and also when the number of 'A' is two or more, positions thereof can be freely selected without restriction. An expression in the context of "at least one piece of A may be replaced by B, C or D" means inclusion of a case where at least one piece of A is replaced by B, a case where at least one piece of A is replaced by C, and a case where at least one piece of A is replaced by D, and also a case where a plurality of pieces of A are replaced by at least two of B, C and D. For example, alkyl in which at least one piece of —CH$_2$— (or —CH$_2$CH$_2$—) may be replaced by —O— (or —CH=CH—) includes alkyl, alkenyl, alkoxy, alkoxyalkyl, alkoxyalkenyl and alkenyloxyalkyl. In addition, a case where two pieces of consecutive —CH$_2$— are replaced by —O— to form —O—O— is not preferred. In alkyl or the like, a case where —CH$_2$— of a methyl part (—CH$_2$—H) is replaced by —O— to form —O—H is not preferred, either.

Then, 2-fluoro-1,4-phenylene means two divalent groups described below. In a chemical formula thereof, fluorine may be leftward (L) or rightward (R). A same rule also applies to a divalent group derived from an asymmetrical ring, such as tetrahydropyran-2,5-diyl.

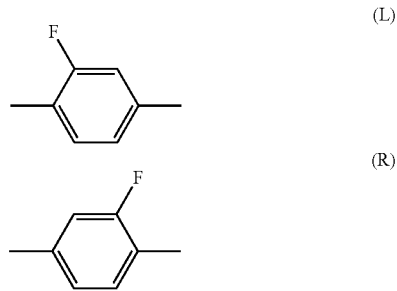

The invention includes items described below.
Item 1. A compound represented by formula (1):

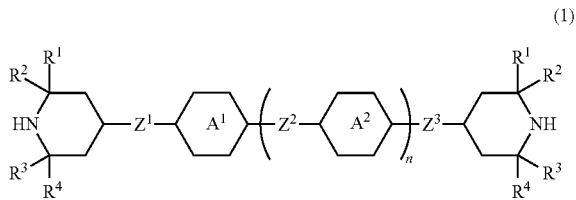

wherein, in formula (1), $R^1$, $R^2$, $R^3$, and $R^4$ are independently hydrogen or alkyl having 1 to 4 carbons; ring $A^1$ and ring $A^2$ are independently 1,4-cyclohexylene, 1,4-cyclohexenylene, 1,2-phenylene, 1,3-phenylene, 1,4-phenylene, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, decahydronaphthalene-2,6-diyl, dihydropyrane-2,5-diyl, tetrahydropyran-2,5-diyl, 1,3-dioxane-2,5-diyl, pyrimidine-2,5-diyl or pyridine-2,5-diyl, and in the rings, at least one piece of hydrogen may be replaced by halogen, alkyl having 1 to 5 carbons, alkoxy having 1 to 5 carbons, or alkyl having 1 to 5 carbons in which at least one piece of hydrogen is replaced by halogen; $Z^1$, $Z^2$ and $Z^3$ are independently a single bond or alkylene having 1 to 10 carbons, and in the alkylene, at least one piece of —CH$_2$— may be replaced by —O— and at least one piece of —CH$_2$—CH$_2$— may be replaced by —CH=CH— or —CH≡CH—, and in the groups, at least one piece of hydrogen may be replaced by fluorine; and n is 0, 1 or 2.

Item 2. The compound according to item 1, wherein, in formula (1) described in item 1, $R^1$, $R^2$, $R^3$ and $R^4$ are independently hydrogen or alkyl having 1 to 4 carbons; ring $A^1$ and ring $A^2$ are independently 1,4-cyclohexylene, 1,4-cyclohexenylene, 1,4-phenylene, 1,4-phenylene in which at least one piece of hydrogen is replaced by fluorine, tetrahydropyran-2,5-diyl, pyrimidine-2,5-diyl, pyridine-2,5-diyl, 1,3-dioxane-2,5-diyl, naphthalene-2,6-diyl, naphthalene-2,6-diyl in which at least one piece of hydrogen is replaced by fluorine, or decahydronaphthalene-2,6-diyl; $Z^1$, $Z^2$ and $Z^3$ are independently a single bond or alkylene having 1 to 10 carbons, and in the alkylene, at least one piece of —CH$_2$— may be replaced by —O— and at least one piece of —CH$_2$—CH$_2$— may be replaced by —CH=CH—; and n is 0, 1 or 2.

Item 3. The compound according to item 1, wherein, in formula (1) described in item 1, $R^1$, $R^2$, $R^3$ and $R^4$ are independently alkyl having 1 to 4 carbons; ring $A^1$ and ring $A^2$ are independently 1,4-cyclohexylene, 1,4-cyclohexenylene, 1,4-phenylene, 1,4-phenylene in which at least one piece of hydrogen is replaced by fluorine, naphthalene-2,6-diyl, or naphthalene-2,6-diyl in which at least one piece of hydrogen is replaced by fluorine; $Z^1$, $Z^2$ and $Z^3$ are independently a single bond or alkylene having 1 to 10 carbons, and in the alkylene, at least one piece of —CH$_2$— may be replaced by —O— and at least one piece of —CH$_2$—CH$_2$— may be replaced by —CH=CH—; and n is 0, 1 or 2.

Item 4. The compound according to item 1, wherein, in formula (1) described in item 1, $R^1$, $R^2$, $R^3$ and $R^4$ are methyl; ring $A^1$ and ring $A^2$ are independently 1,4-cyclohexylene, 1,4-phenylene, or 1,4-phenylene in which at least one piece of hydrogen is replaced by fluorine; $Z^1$ and $Z^3$ are single bonds, and $Z^2$ is a single bond, —CH$_2$—, —CH$_2$CH$_2$—, —CH=CH—, —OCH$_2$— or —CH$_2$O—; and n is 0 or 1.

Item 5. The compound according to item 1, wherein, in formula (1) described in item 1, $R^1$, $R^2$, $R^3$ and $R^4$ are methyl; ring $A^1$ and ring $A^2$ are independently 1,4-phenylene or 2-fluoro-1,4-phenylene; $Z^1$, $Z^2$ and $Z^3$ are single bonds; and n is 0 or 1.

Item 6. A liquid crystal composition, containing at least one compound according to any one of items 1 to 5.

Item 7. The liquid crystal composition according to item 6, further containing at least one compound selected from the group of compounds represented by formulas (2) to (4):

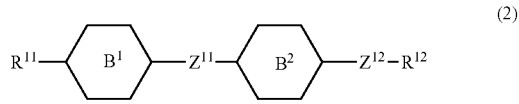

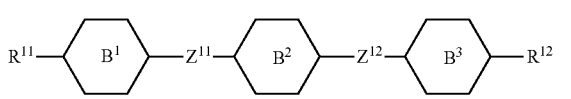

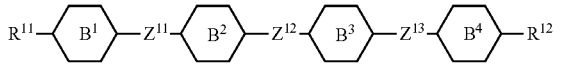

wherein, in formulas (2) to (4),
$R^{11}$ and $R^{12}$ are independently alkyl having 1 to 10 carbons or alkenyl having 2 to 10 carbons, and in the alkyl or the alkenyl, at least one piece of —CH$_2$— may be replaced by —O—, and at least one piece of hydrogen may be replaced by fluorine;

ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and $Z^{11}$, $Z^{12}$ and $Z^{13}$ are independently a single bond, —$CH_2CH_2$—, —CH=CH—, —C≡C— or —COO—.

Item 8. The liquid crystal composition according to item 6 or 7, further containing at least one compound selected from the group of compounds represented by formulas (5) to (7):

(5)

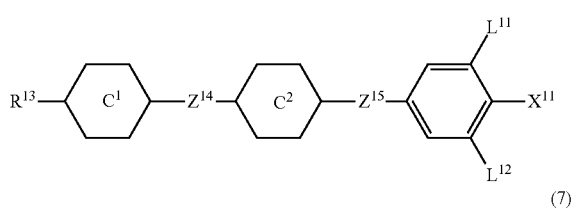
(6)

(7)

wherein, in formulas (5) to (7), $R^{13}$ is alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine;

$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

ring $C^1$, $C^2$ and $C^3$ are independently 1,4-cyclohexylene, 1,4-phenylene in which at least one piece of hydrogen may be replaced by fluorine, tetrahydropyran-2,5-diyl, 1,3-dioxane-2,5-diyl or pyrimidine-2,5-diyl;

$Z^{14}$, $Z^{15}$ and $Z^{16}$ are independently a single bond, —$CH_2CH_2$—, —CH=CH—, —C≡C—, —COO—, —$CF_2O$—, —$OCF_2$—, —$CH_2O$— or —$(CH_2)_4$—; and $L^{11}$ and $L^{12}$ are independently hydrogen or fluorine.

Item 9. The liquid crystal composition according to item 6 or 7, further containing at least one compound selected from the group of compounds represented by formula (8):

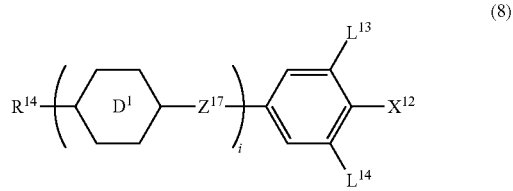
(8)

wherein, in formula (8), $R^{14}$ is alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine;

$X^{12}$ is —C≡N or —C≡C—C≡N;

ring $D^1$ is 1,4-cyclohexylene, 1,4-phenylene in which at least one piece of hydrogen may be replaced by fluorine, tetrahydropyran-2,5-diyl, 1,3-dioxane-2,5-diyl or pyrimidine-2,5-diyl;

$Z^{17}$ is a single bond, —$CH_2CH_2$—, —C≡C—, —COO—, —$CF_2O$—, —$OCF_2$— or —$CH_2O$—;

$L^{13}$ and $L^{14}$ are independently hydrogen or fluorine; and i is 1, 2, 3 or 4.

Item 10. The liquid crystal composition according to any one of items 6 to 9, further containing at least one of a polymerizable compound, a polymerization initiator, a polymerization inhibitor, an optically active compound, an antioxidant, an ultraviolet light absorber, a light stabilizer, a heat stabilizer and an antifoaming agent.

Item 11. A liquid crystal display device, including at least one liquid crystal composition according to any one of items 6 to 10.

The invention further includes the following items: (a) the liquid crystal composition, further containing at least two additives such as a polymerizable compound, a polymerization initiator, a polymerization inhibitor, an optically active compound, an antioxidant, an ultraviolet light absorber, a light stabilizer, a heat stabilizer and an antifoaming agent; (b) a polymerizable composition prepared by adding the polymerizable compound to the liquid crystal composition; (c) a liquid crystal composite prepared by polymerizing the polymerizable composition; (d) a polymer sustained alignment (PSA) mode AM device including the liquid crystal composite; (e) use of compound (1) as the light stabilizer; (f) use of compound (1) as the heat stabilizer; (g) use in combination of a light stabilizer different from compound (1) with compound (1); (h) use as an optically active composition by adding the optically active compound to the liquid crystal composition.

The compound, the liquid crystal composition and the liquid crystal display device according to the invention will be described in the order.

1. Compound (1)

Compound (1) of the invention has two 2,2,6,6-tetra alkyl piperidine rings, and therefore is useful as a hindered amine light stabilizer. The compound can be added to the liquid crystal composition. The reason is that the compound has a high solubility in the liquid crystal composition. The liquid crystal composition is a mixture of the liquid crystal compounds. Compound (1) is effective in preventing the liquid crystal compound from being decomposed by light from backlight or the sun. The compound also seems to have an effect as the heat stabilizer.

When the liquid crystal display device is used for a long period of time, the liquid crystal compound therein tends to be decomposed by light to produce a decomposition product. The product is an impurity, and therefore is unfavorable for the device. The reason is that the impurity causes a phenomenon such as reduction of contrast, occurrence of display unevenness and image persistence. The phenomenon can be easily identified by visual observation, and is significantly distinguished even if a degree thereof is only limited. Accordingly, the light stabilizer that generates the impurity in an amount smaller even by 1% in comparison with a conventional light stabilizer is preferred. Compound (1) is such a light stabilizer described above.

Preferred examples of compound (1) are described. Preferred examples of substituent R, ring A and a bonding group Z in compound (1) are also applied to a subordinate formula of formula (1) for compound (1). In compound (1), physical properties can be arbitrarily adjusted by suitably combining kinds of the groups. Compound (1) may contain an isotope such as $^{2}H$ (deuterium) and $^{13}C$ in an amount larger than an amount of natural abundance because no significant difference exists in the physical properties of the compound.

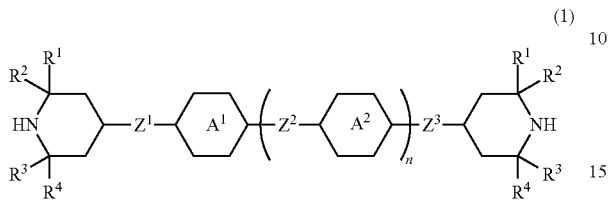

In formula (1), $R^1$, $R^2$, $R^3$, and $R^4$ are independently hydrogen or alkyl having 1 to 4 carbons. A preferred example of $R^1$, $R^2$, $R^3$, or $R^4$ is methyl or ethyl. A further preferred example is methyl. Two symbols $R^1$ exist in formula (1). Two groups represented by two pieces of $R^1$ may be identical or different. A same rule also applies to $R^2$ or the like.

In formula (1), ring $A^1$ and ring $A^2$ are independently 1,4-cyclohexylene, 1,4-cyclohexenylene, 1,2-phenylene, 1,3-phenylene, 1,4-phenylene, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, decahydronaphthalene-2,6-diyl, dihydropyrane-2,5-diyl, tetrahydropyran-2,5-diyl, 1,3-dioxane-2,5-diyl, pyrimidine-2,5-diyl or pyridine-2,5-diyl. In the rings, at least one piece of hydrogen may be replaced by halogen, alkyl having 1 to 5 carbons, alkoxy having 1 to 5 carbons, or alkyl having 1 to 5 carbons in which at least one piece of hydrogen is replaced by halogen.

Preferred examples of 1,4-phenylene in which at least one piece of hydrogen is replaced by halogen include 2-fluoro-1,4-phenylene, 2-chloro-1,4-phenylene, 2,3-difluoro-1,4-phenylene, 2-chloro-3-fluoro-1,4-phenylene, 2,5-difluoro-1,4-phenylene, 2-chloro-5-fluoro-1,4-phenylene, 2-chloro-6-fluoro-1,4-phenylene or 2,6-difluoro-1,4-phenylene. Further preferred examples of 1,4-phenylene in which at least one piece of hydrogen is replaced by halogen include 2-fluoro-1,4-phenylene or 2, 3-difluoro-1,4-phenylene.

Preferred examples of naphthalene-2,6-diyl in which at least one piece of hydrogen is replaced by halogen include 1-fluoro-naphthalene-2,6-diyl or 3-fluoro-naphthalene-2,6-diyl.

Preferred examples of ring $A^1$ or ring $A^2$ include 1,4-cyclohexylene, 1,4-phenylene, 1,4-phenylene in which at least one piece of hydrogen is replaced by fluorine or chlorine, 2-methyl-1,4-phenylene and naphthalene-2,6-diyl. Cis and trans configurations exist in 1,4-cyclohexylene. From a viewpoint of a high maximum temperature, a trans configuration is preferred. Further preferred examples include 1,4-cyclohexylene, 1,4-phenylene or 2-fluoro-1,4-phenylene. Most preferred examples include 1,4-phenylene or 2-fluoro-1,4-phenylene.

In formula (1), bonding groups $Z^1$, $Z^2$ and $Z^3$ are independently a single bond or alkylene having 1 to 10 carbons, and in the alkylene, at least one piece of $-CH_2-$ may be replaced by $-O-$, at least one piece of $-CH_2-CH_2-$ may be replaced by $-CH=CH-$ or $-CH\equiv CH-$, and at least one piece of hydrogen may be replaced by fluorine.

Preferred examples of $Z^1$, $Z^2$ or $Z^3$ include a single bond, alkylene having 1 to 5 carbons, $-OCH_2-$ or $-CH_2O-$. A further preferred example is a single bond.

In formula (1), n is 0, 1 or 2. Preferred examples of n are 0 or 1. Preferred examples are also 1 or 2. A further preferred example is 0. A still further preferred example is also 1.

With referring to the preferred examples described above, compound (1) having objective physical properties can be obtained by suitably selecting a combination of substituent A, ring A and bonding group Z. A preferred example of compound (1) is compound (1-1).

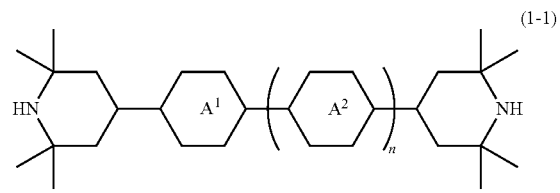

In compound (1-1), ring $A^1$ and ring $A^2$ are independently 1,4-cyclohexylene, 1,4-phenylene, 2-fluoro-1,4-phenylene or 2,3-difluoro-1,4-phenylene; and n is 0 or 1. The compound has a feature of having a piperidine ring in which replacement is made by four methyl groups in 2-position and 6-position. An amino group (NH) positioned between the groups is subjected to steric hindrance, and therefore subjected to control of reactivity. Accordingly, compound (1) is suitable for trapping the decomposition product formed by photoreaction of the liquid crystal compound.

Further preferred examples of compound (1) include compound (1-1-1), compound (1-1-2) or compound (1-1-3).

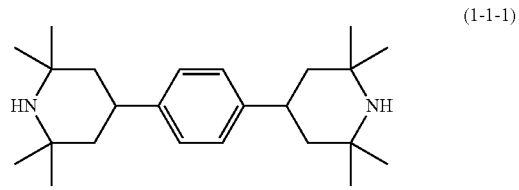

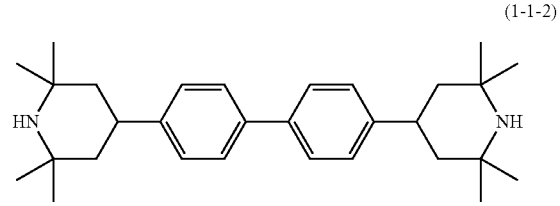

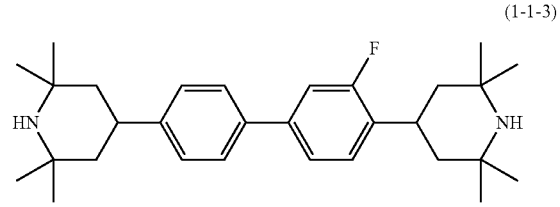

Synthesis of compound (1)

A method for synthesizing compound (1) is described. Compound (1) can be prepared by using 2,2,6,6-tetraalkylpiperidine-4-one as a starting material and repeating reactions of forming carbon-carbon bonds. Preparation procedures are described in sections in Examples. The reactions of forming the carbon-carbon bonds and reactions of converting functional groups are described in books such as "Organic Syntheses" (John Wiley & Sons, Inc.), "Organic Reactions" (John Wiley & Sons, Inc.), "Comprehensive Organic Synthesis" (Pergamon Press), and New Experimental Chemistry Course (Shin Jikken Kagaku Koza in Japanese) (Maruzen Co., Ltd.).

2. Liquid Crystal Composition

The liquid crystal composition of the invention contains compound (1) as component A. Compound (1) is suitable for preventing the liquid crystal composition from being decomposed by light or heat. The composition contains compound (1) as component A, and preferably further contains a compound selected from components B, C and D described below. Component B includes compounds (2) to (4). Component C includes compounds (5) to (7). Component D includes compound (8). Upon preparing the composition, components B, C and D are preferably selected in taking into account positive or negative dielectric anisotropy, magnitude of dielectric anisotropy or the like. A composition in which the component is suitably selected has a high maximum temperature, a low minimum temperature, a small viscosity, a suitable optical anisotropy (more specifically, large optical anisotropy or small optical anisotropy), a large positive or negative dielectric anisotropy and a suitable elastic constant (more specifically, large elastic constant or small elastic constant).

A preferred proportion of compound (1) is about 0.01% by weight or more in order to maintain the high stability to ultraviolet light, and about 5% by weight or less in order to be dissolved into the liquid crystal composition, based on the total weight of the liquid crystal composition. A further preferred proportion is in the range of about 0.05% by weight to about 2% by weight. A most preferred proportion is in the range of about 0.05% by weight to about 1% by weight.

Component B is a compound in which two terminal groups are alkyl or the like. Specific preferred examples of component B include compounds (2-1) to (2-11), compounds (3-1) to (3-19) and compounds (4-1) to (4-7). In the compound of component B, definitions of $R^{11}$ and $R^{12}$ are identical with the definitions in formulas (2) to (4) described in item 7.

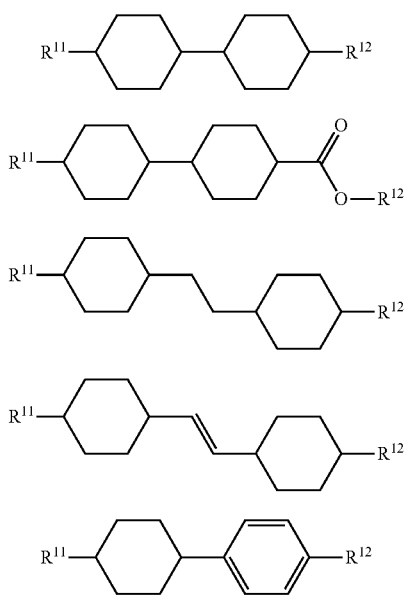

-continued

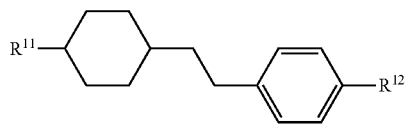
(2-6)

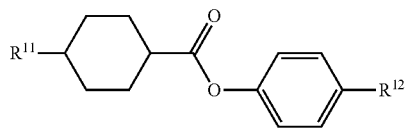
(2-7)

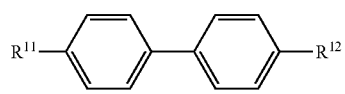
(2-8)

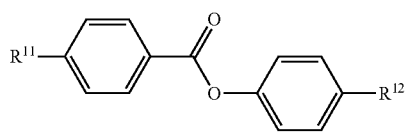
(2-9)

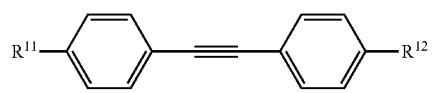
(2-10)

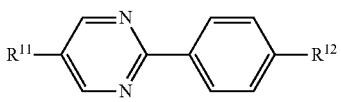
(2-11)

(3-1)

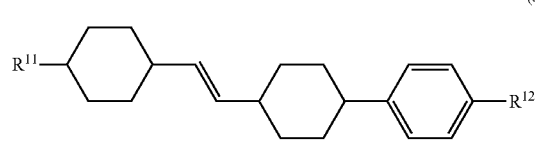
(3-2)

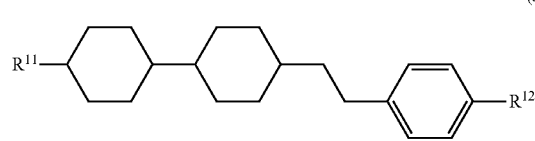
(3-3)

(3-4)

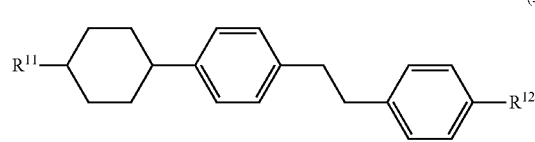
(3-5)

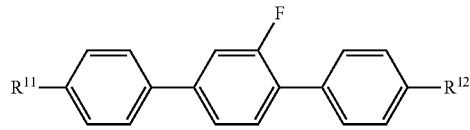
(3-6)

(3-7) 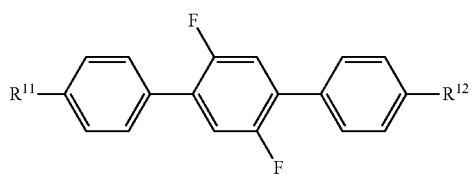

(3-8) 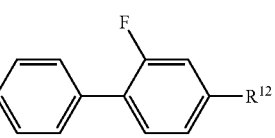

(3-9) 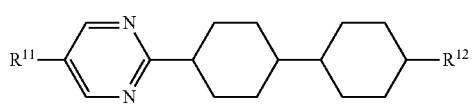

(3-10) 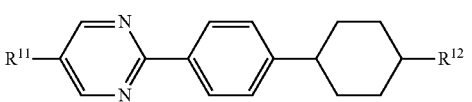

(3-11) 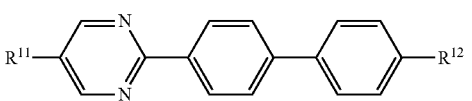

(3-12) 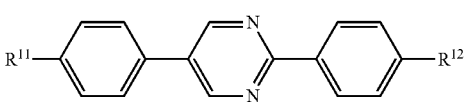

(3-13) 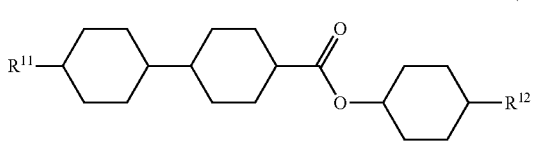

(3-14) 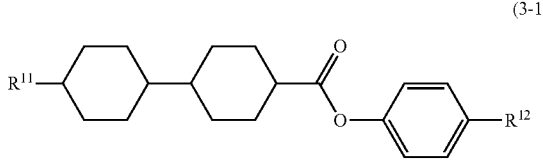

(3-15) 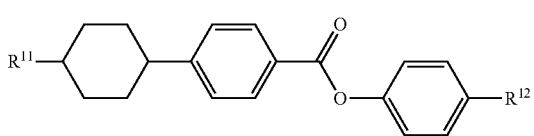

(3-16) 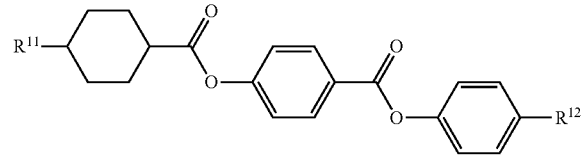

(3-17) 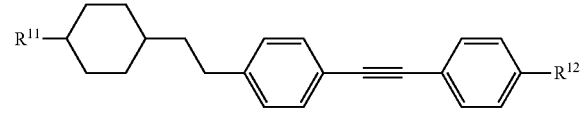

(3-18) 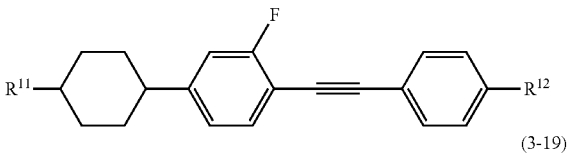

(3-19) 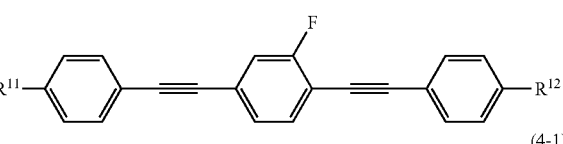

(4-1) 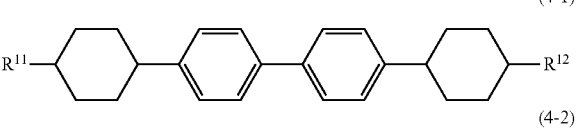

(4-2) 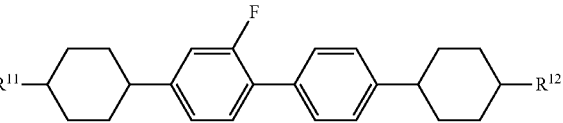

(4-3) 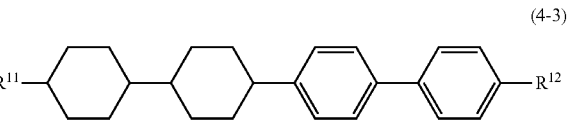

(4-4) 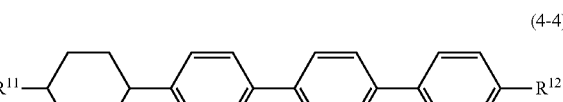

(4-5) 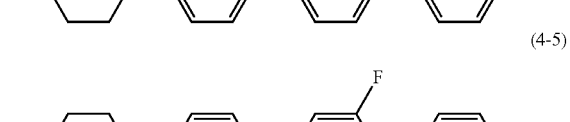

(4-6) 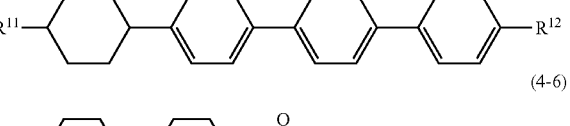

(4-7) 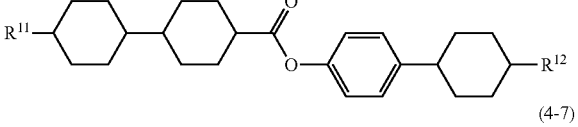

Component B has a small absolute value of dielectric anisotropy, and therefore is a compound close to neutrality. Compound (2) is effective mainly in adjusting the viscosity or the optical anisotropy. Compounds (3) and (4) are effective in extending the temperature range of the nematic phase by increasing the maximum temperature, or in adjusting the optical anisotropy.

Accordingly as a content of component B is increased, the viscosity of the composition is decreased, but the dielectric anisotropy decreases. Thus, as long as a desired value of threshold voltage of the device is met, the content is preferably as large as possible. Therefore, when a composition for an IPS mode, a VA mode or the like is prepared, the content of component (B) is preferably 30% by weight or more, and further preferably 40% by weight or more, based on the weight of the liquid crystal composition.

Component C is a compound having a halogen-containing group or a fluorine-containing group at a right terminal. Specific preferred examples of component C include compounds (5-1) to (5-16), compounds (6-1) to (6-113) and compounds (7-1) to (7-57). In the compound of component C, definitions of $R^{13}$ and $X^{11}$ are identical with the definitions in formulas (5) to (7) described in item 8.

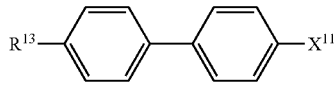 (5-1)

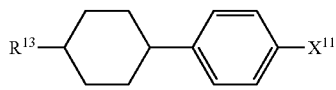 (5-2)

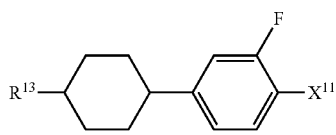 (5-3)

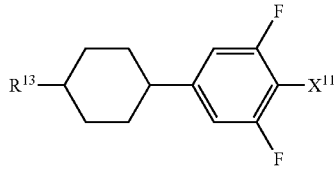 (5-4)

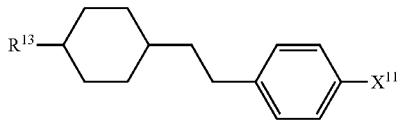 (5-5)

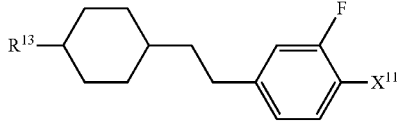 (5-6)

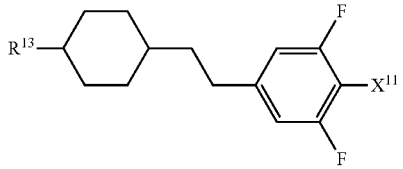 (5-7)

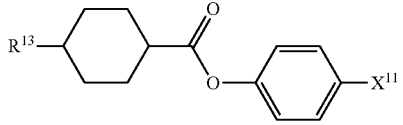 (5-8)

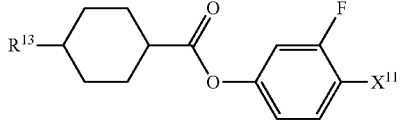 (5-9)

-continued

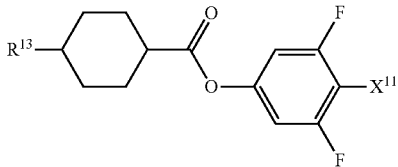 (5-10)

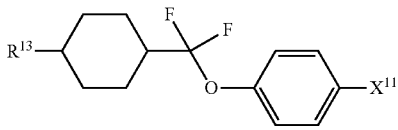 (5-11)

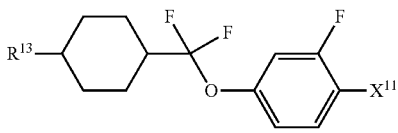 (5-12)

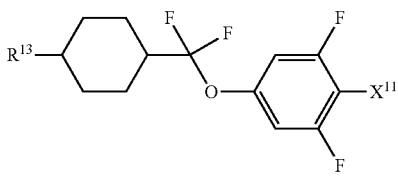 (5-13)

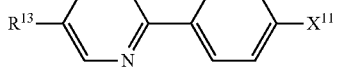 (5-14)

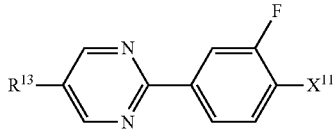 (5-15)

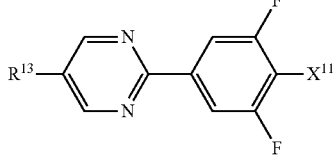 (5-16)

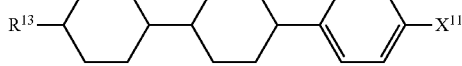 (6-1)

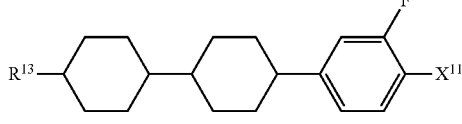 (6-2)

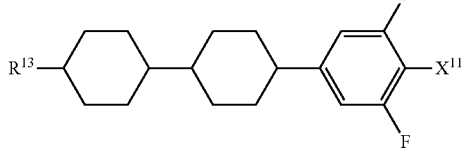 (6-3)

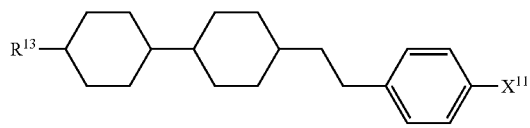(6-4)
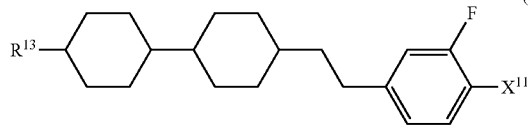(6-5)
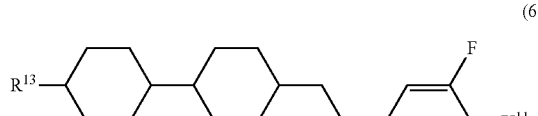(6-6)
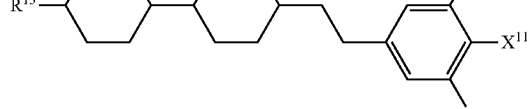(6-7)
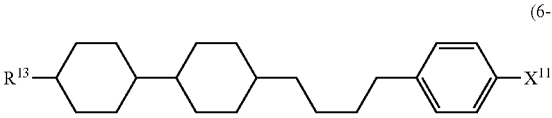(6-8)
(6-9)
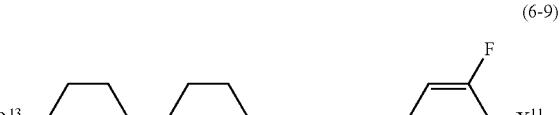(6-10)
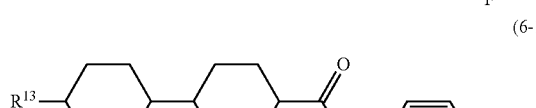(6-11)
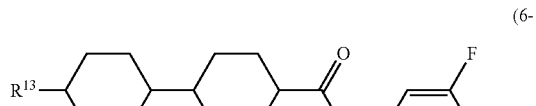(6-12)
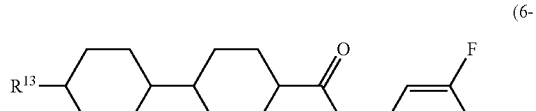(6-13)
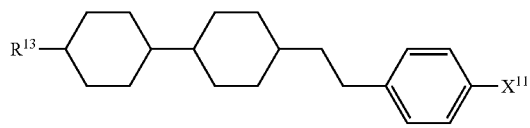(6-14)
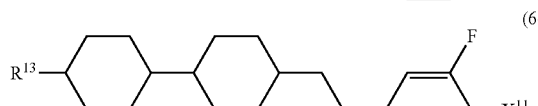(6-15)
(6-16)
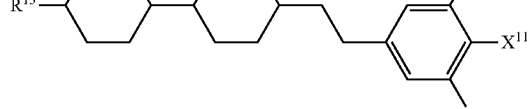(6-17)
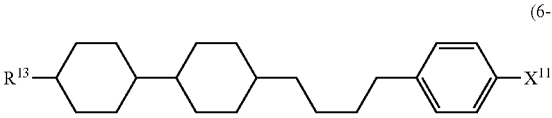(6-18)
(6-19)
(6-20)
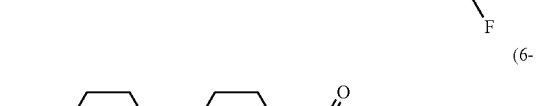(6-21)
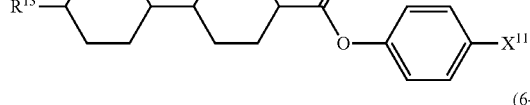(6-22)
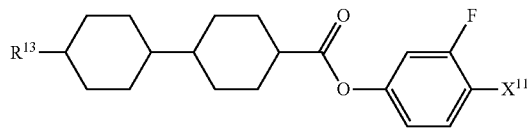(6-23)

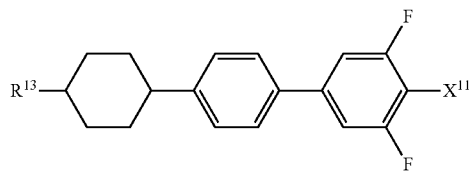
(6-24)
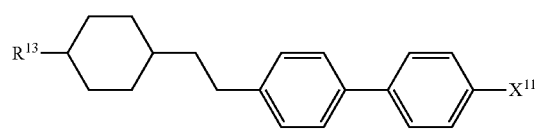
(6-25)
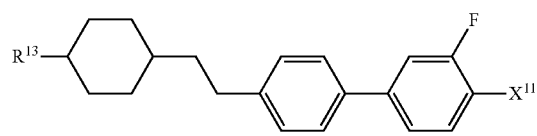
(6-26)
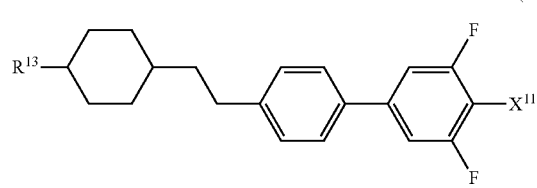
(6-27)
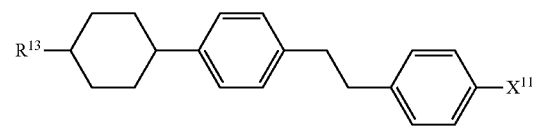
(6-28)
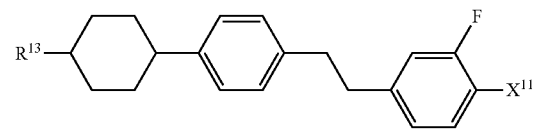
(6-29)
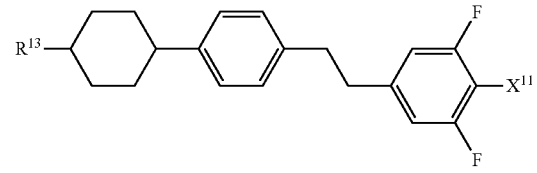
(6-30)
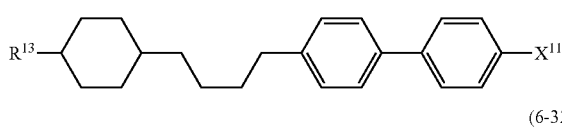
(6-31)
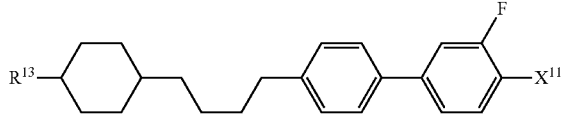
(6-32)
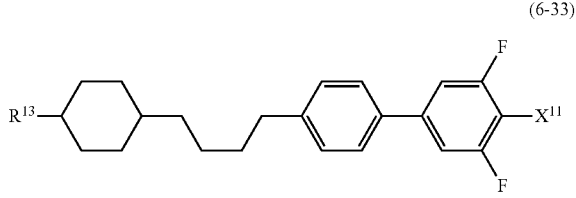
(6-33)
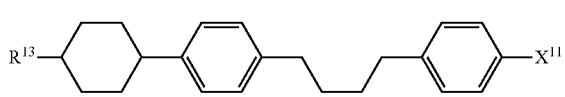
(6-34)
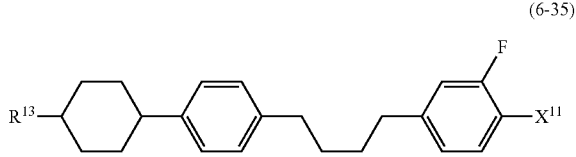
(6-35)
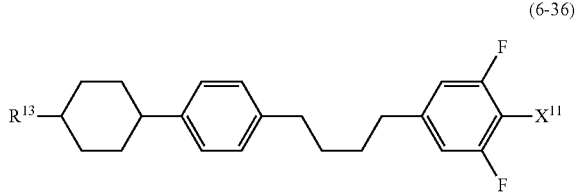
(6-36)
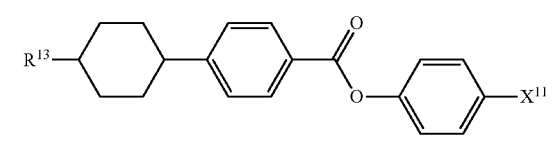
(6-37)
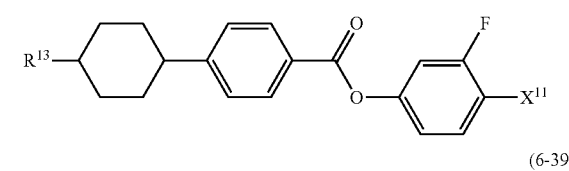
(6-38)
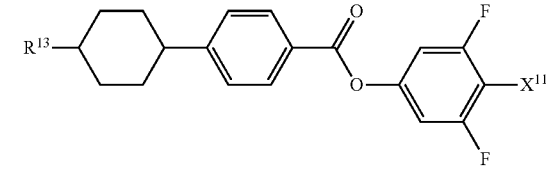
(6-39)
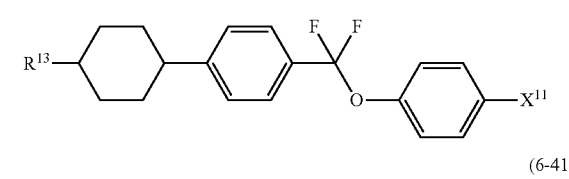
(6-40)
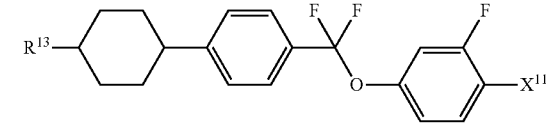
(6-41)

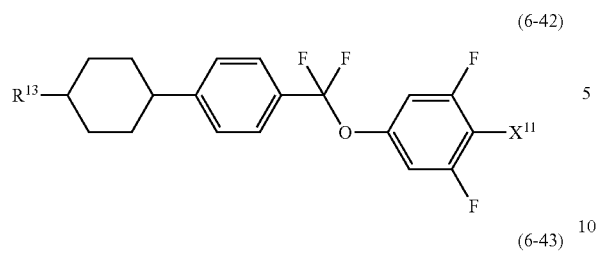
(6-42)
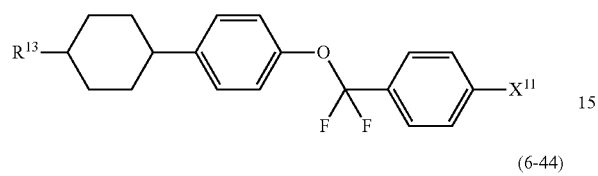
(6-43)
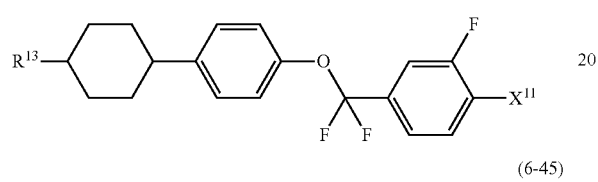
(6-44)
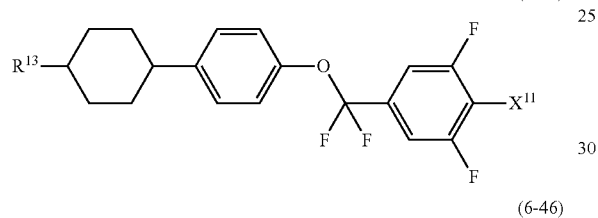
(6-45)
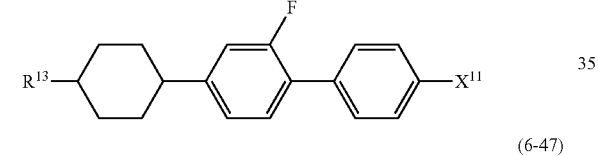
(6-46)
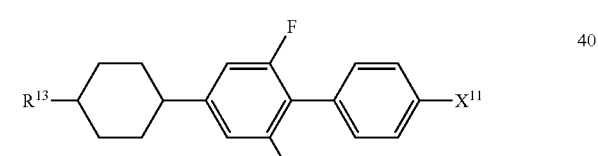
(6-47)
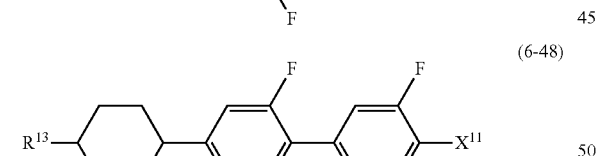
(6-48)
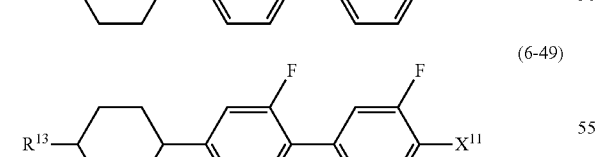
(6-49)
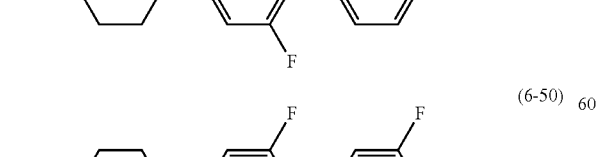
(6-50)
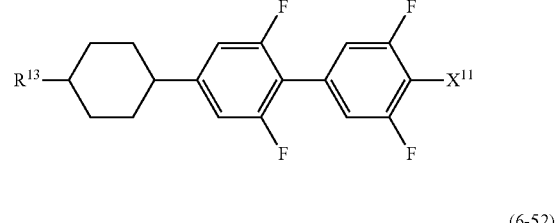
(6-51)
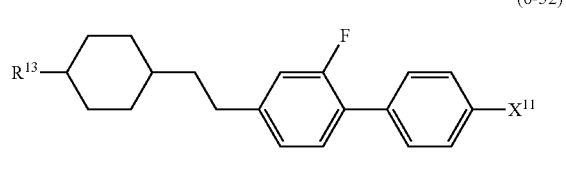
(6-52)
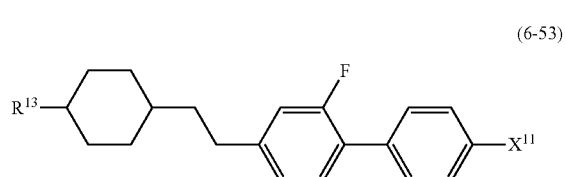
(6-53)
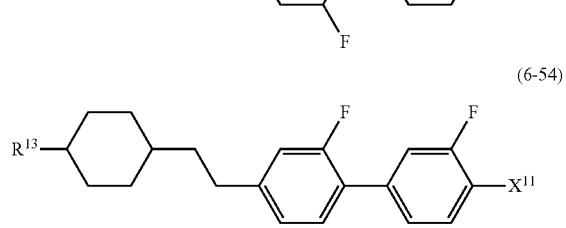
(6-54)
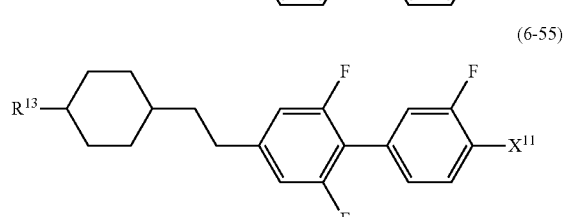
(6-55)
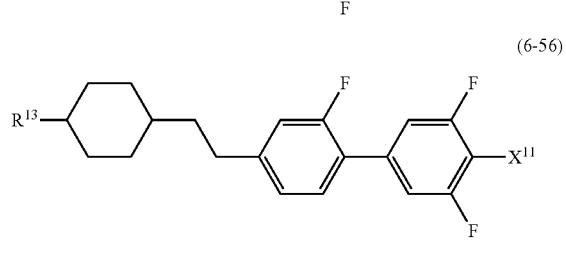
(6-56)
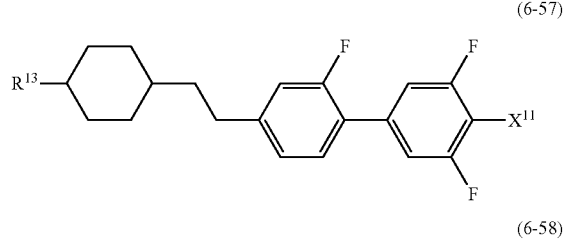
(6-57)
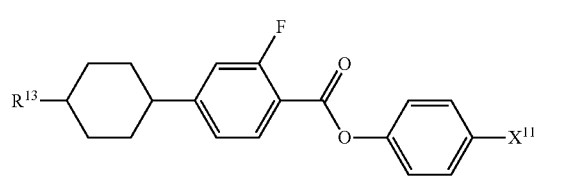
(6-58)

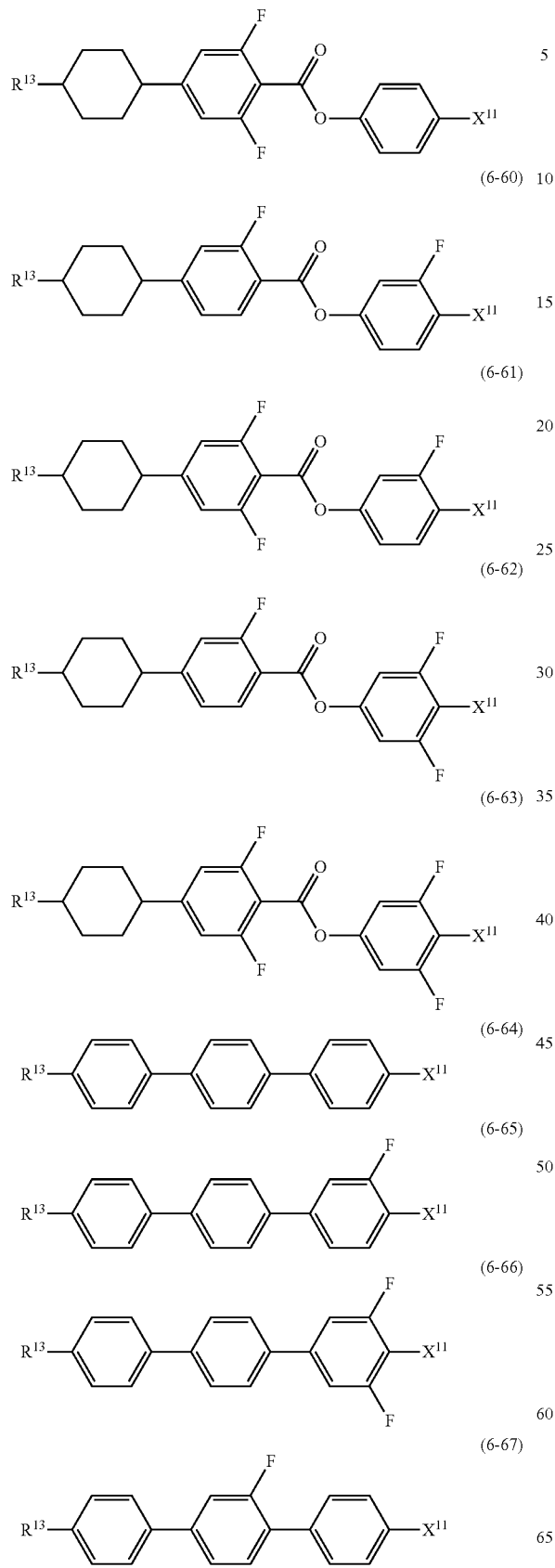
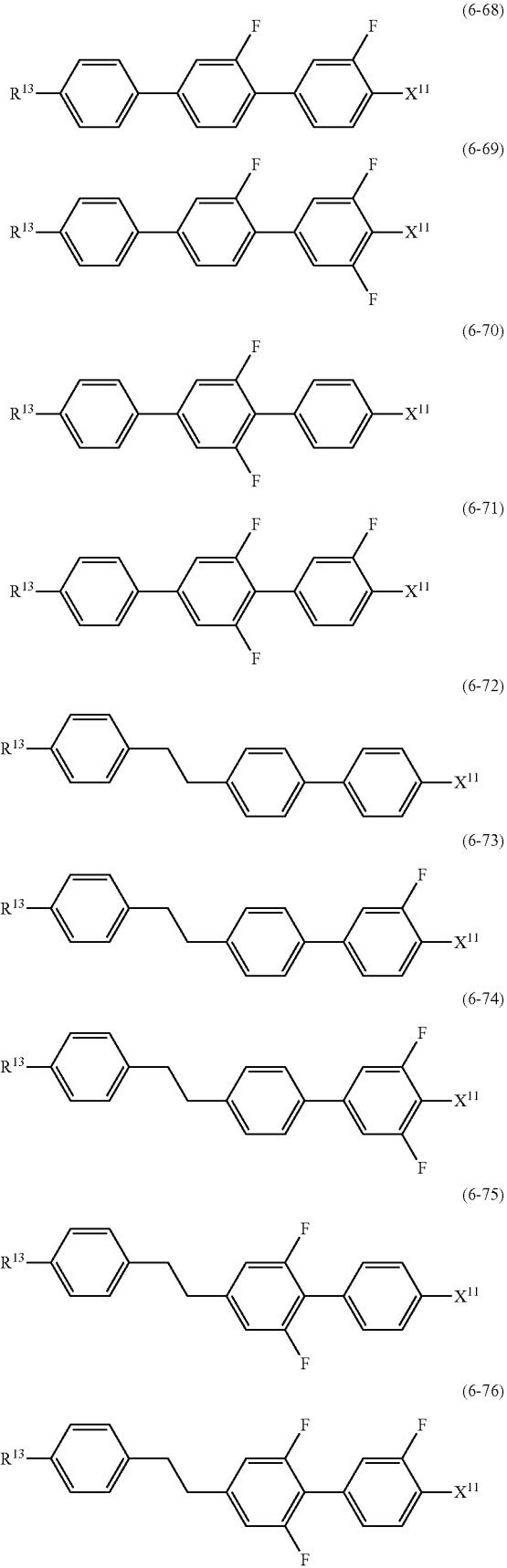

-continued (6-77)
(6-78)
(6-79)
(6-80)
(6-81)
(6-82)
(6-83)
(6-84)
(6-85)

-continued (6-86)
(6-87)
(6-88)
(6-89)
(6-90)
(6-91)
(6-92)
(6-93)

(6-94)
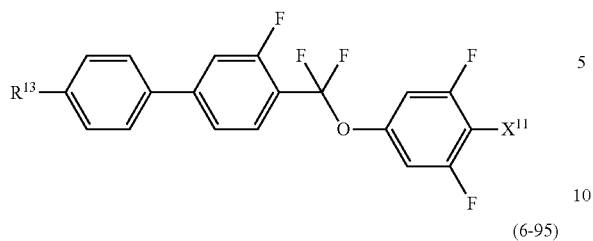
(6-95)
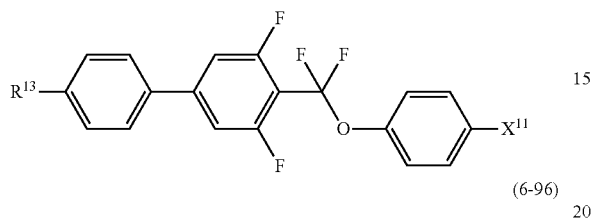
(6-96)
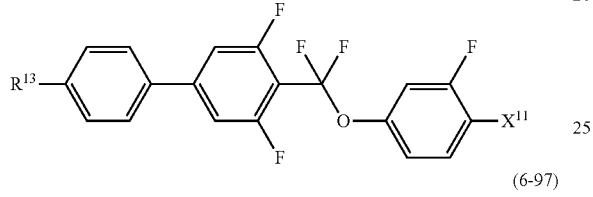
(6-97)
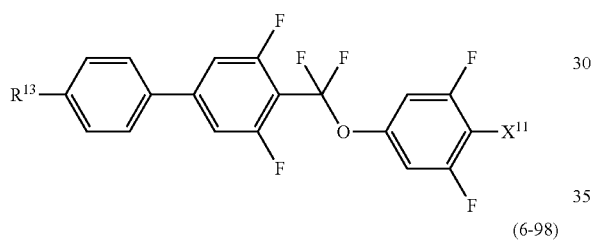
(6-98)
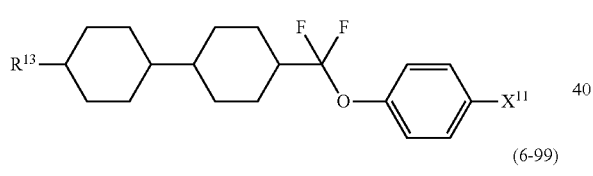
(6-99)
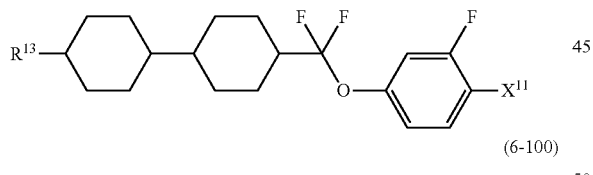
(6-100)
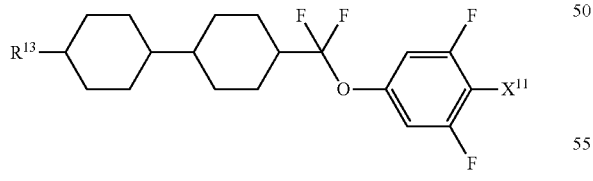
(6-101)
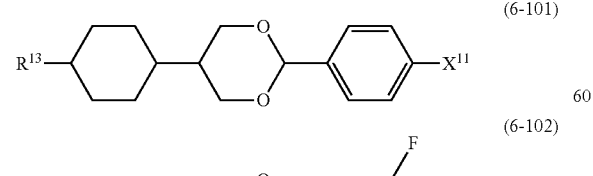
(6-102)
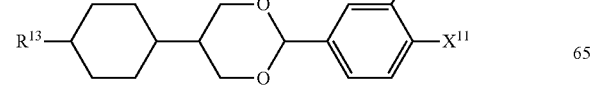
(6-103)
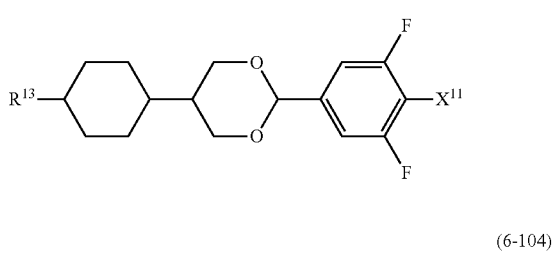
(6-104)
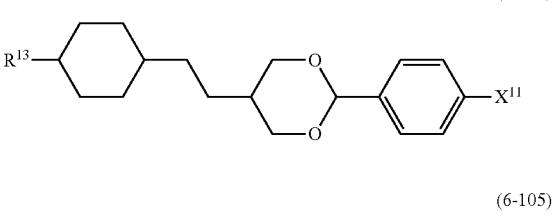
(6-105)
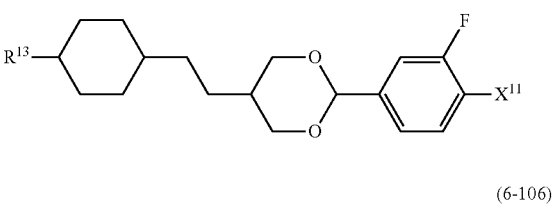
(6-106)
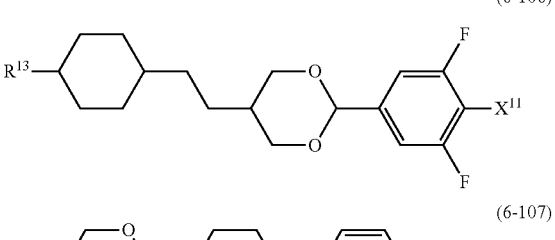
(6-107)
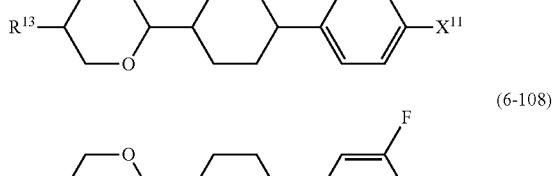
(6-108)
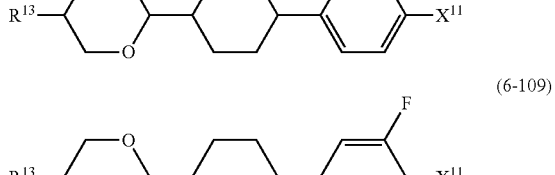
(6-109)
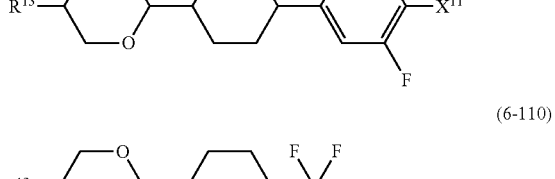
(6-110)
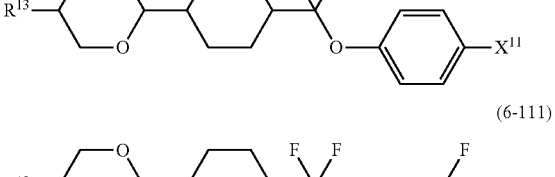
(6-111)
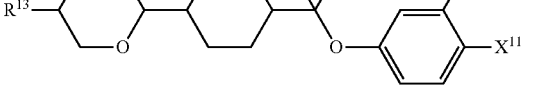

(6-112)
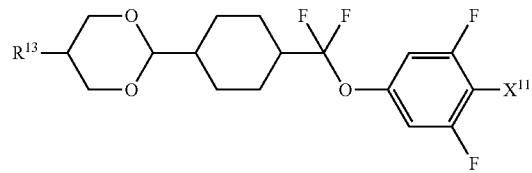
(6-113)
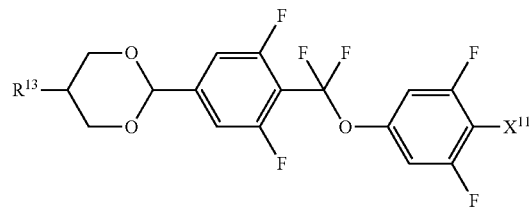
(7-1)
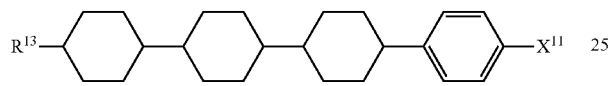
(7-2)
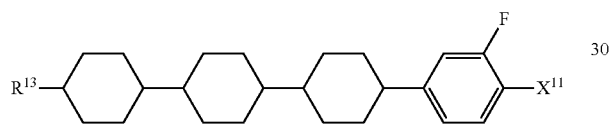
(7-3)
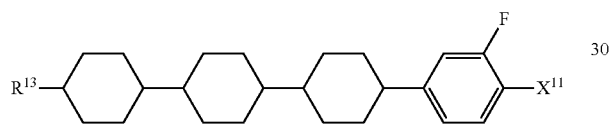
(7-4)
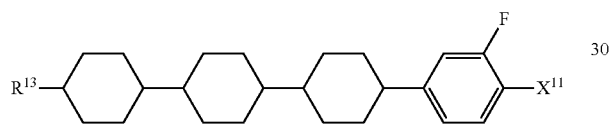
(7-5)
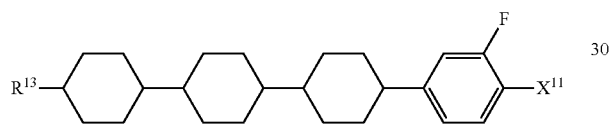
(7-6)
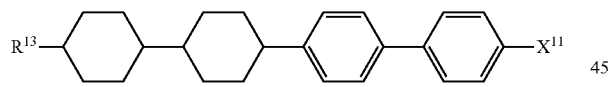
(7-7)
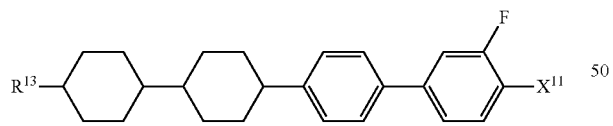
(7-8)
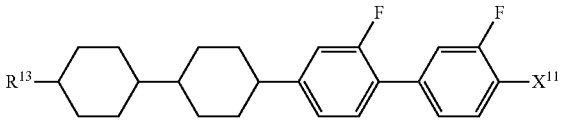
(7-9)
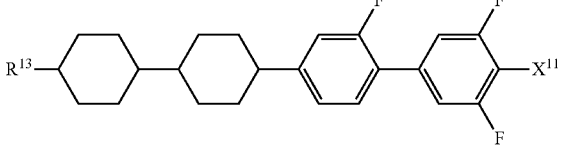
(7-10)
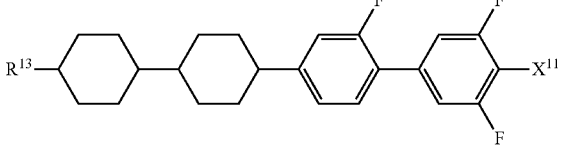
(7-11)
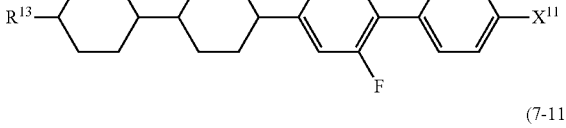
(7-12)
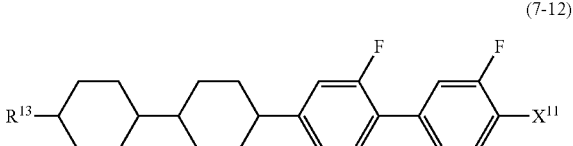
(7-13)
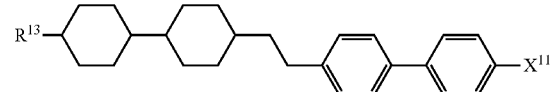
(7-14)
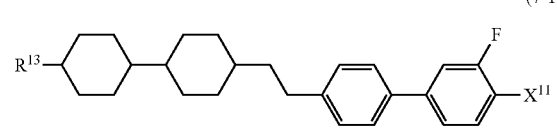
(7-15)
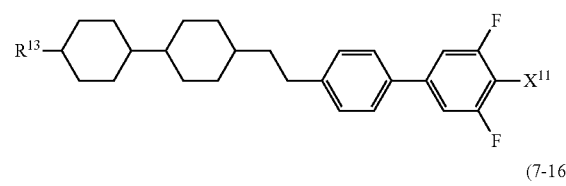
(7-16)
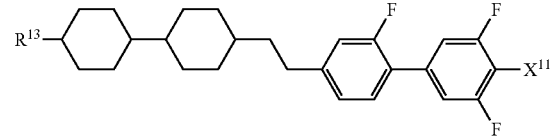

(7-17)
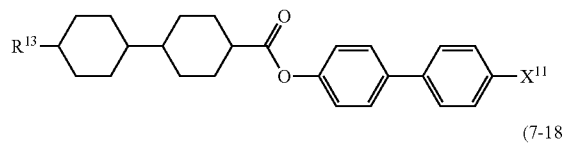
(7-18)
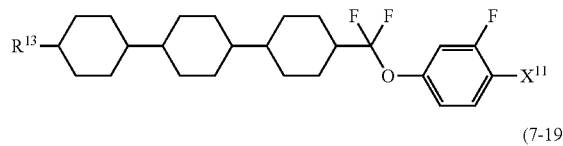
(7-19)
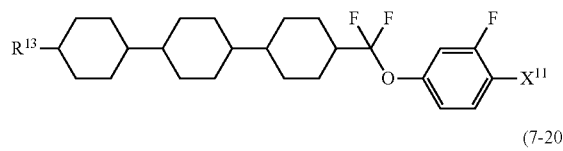
(7-20)
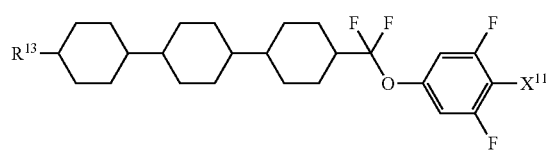
(7-21)
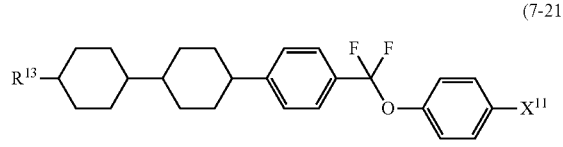
(7-22)
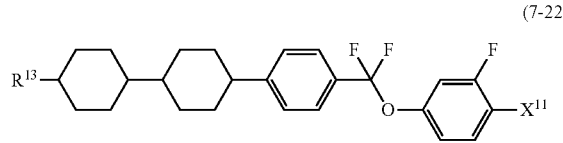
(7-23)
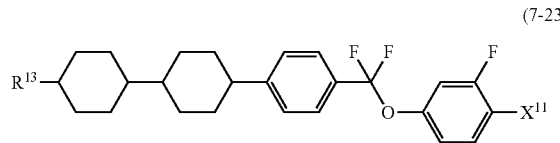
(7-24)
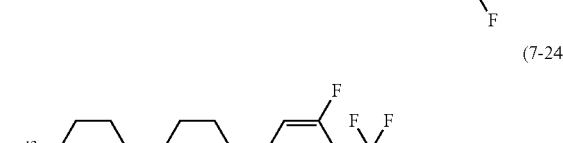
(7-25)
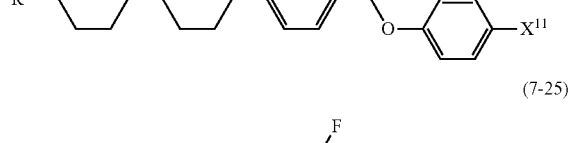
(7-26)
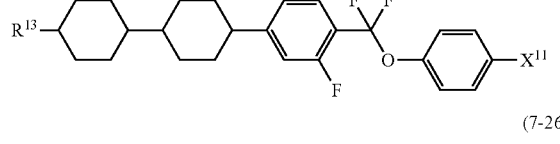
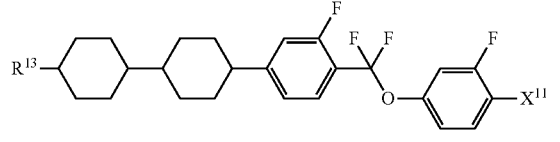
(7-27)
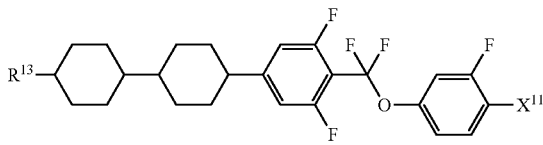
(7-28)
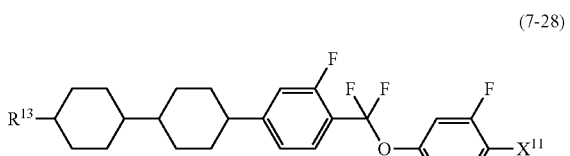
(7-29)
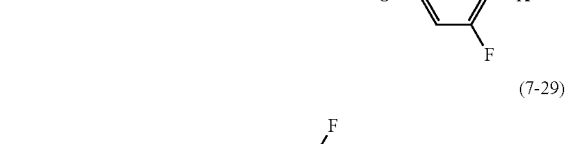
(7-30)
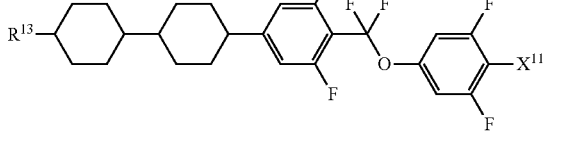
(7-31)
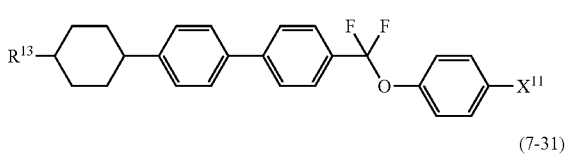
(7-32)
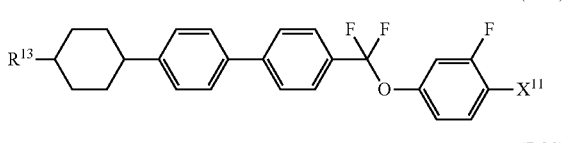
(7-33)
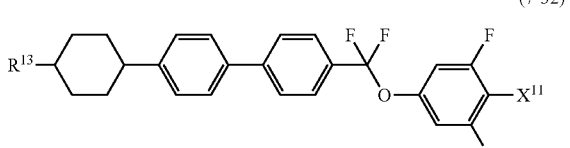
(7-34)
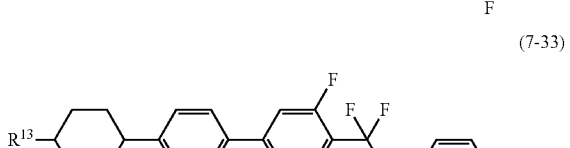
(7-35)
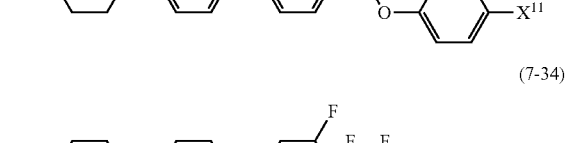
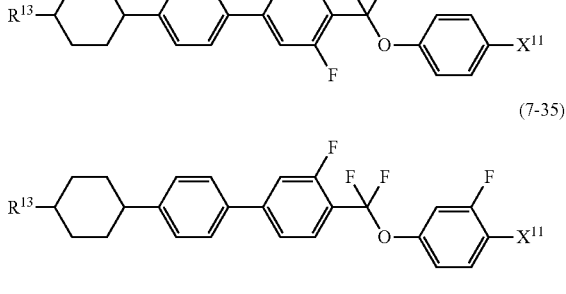

(7-36) 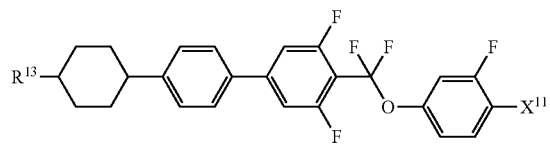
(7-37) 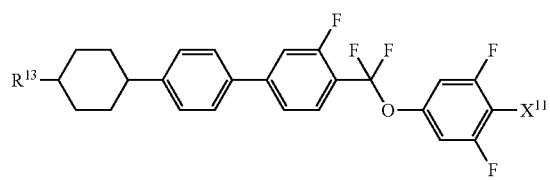
(7-38) 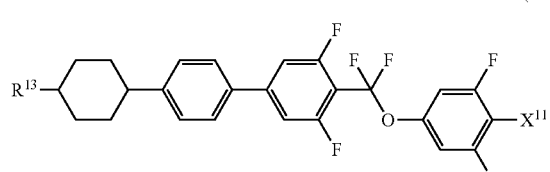
(7-39) 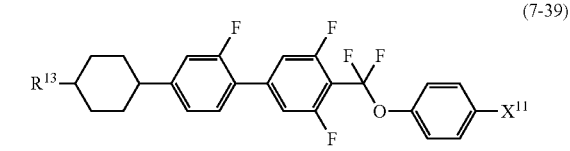
(7-40) 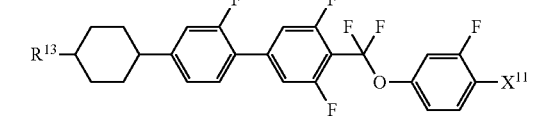
(7-41) 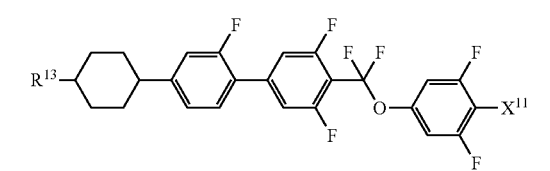
(7-42) 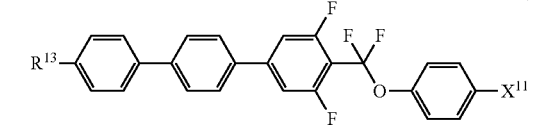
(7-43) 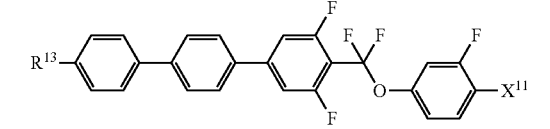
(7-44) 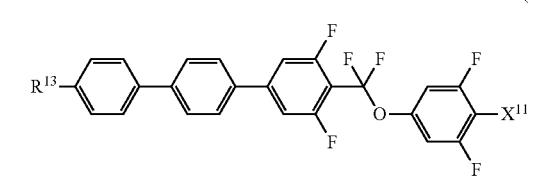
(7-45) 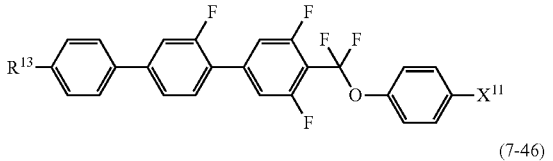
(7-46) 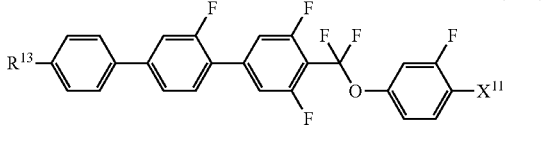
(7-47) 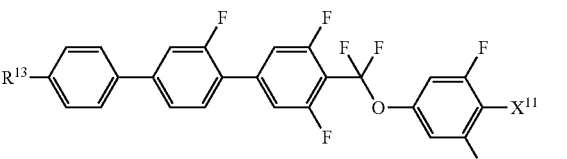
(7-48) 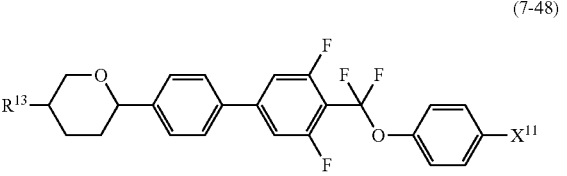
(7-49) 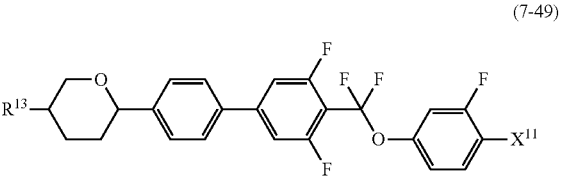
(7-50) 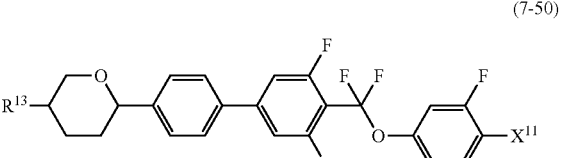
(7-51) 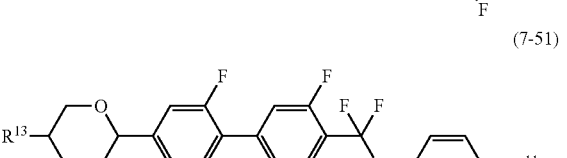
(7-52) 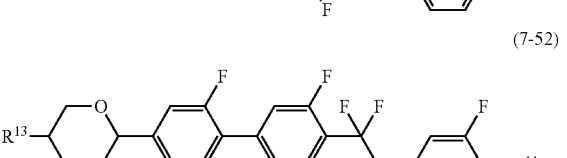
(7-53) 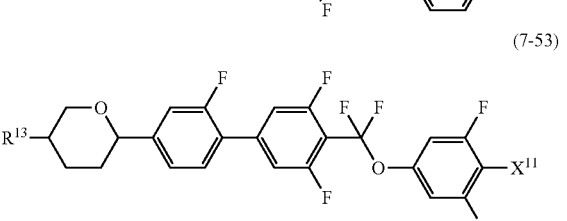

(7-54)

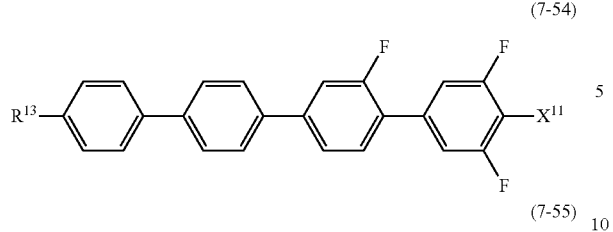

(7-55)

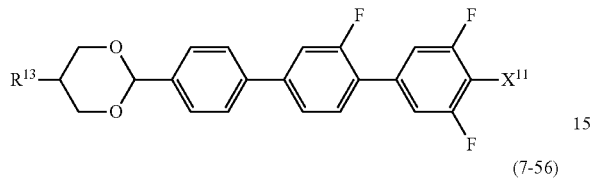

(7-56)

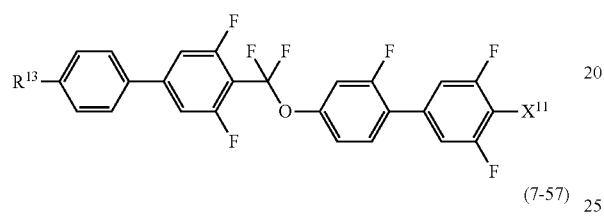

(7-57)

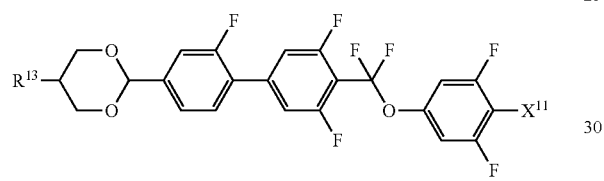

Component C has the positive dielectric anisotropy, and superb stability to heat, light and so forth, and therefore is used when a composition for a mode such as IPS, FFS and OCB is prepared. A content of component C is suitably in the range of 1% by weight to 99% by weight, preferably in the range of 10% by weight to 97% by weight, and further preferably in the range of 40% by weight to 95% by weight, based on the weight of the liquid crystal composition. When component C is added to a composition having the negative dielectric anisotropy, the content of component C is preferably 30% by weight or less based on the weight of the composition. An elastic constant of the composition and a voltage-transmittance curve of the device can be adjusted by adding component C thereto.

Component D is compound (8) in which a right-terminal group is —C≡N or —C≡C—C≡N. Preferred examples of component D include compounds (8-1) to (8-64). In the compound of component D, definitions of $R^{14}$ and $X^{12}$ are identical with the definitions in formula (8) described in item 9.

(8-1)

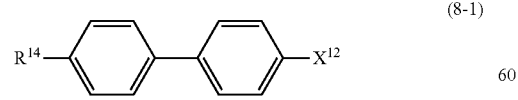

(8-2)

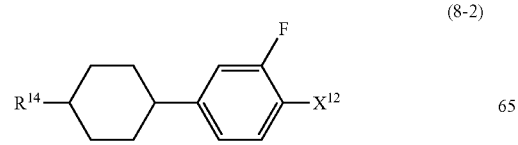

(8-3)

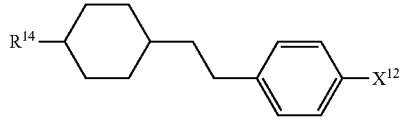

(8-4)

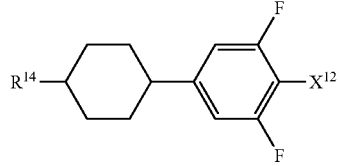

(8-5)

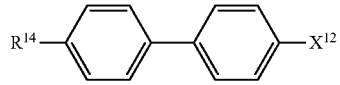

(8-6)

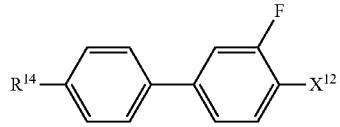

(8-7)

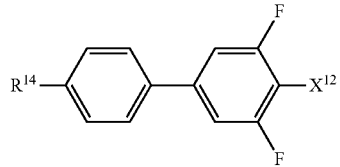

(8-8)

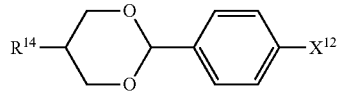

(8-9)

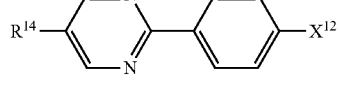

(8-10)

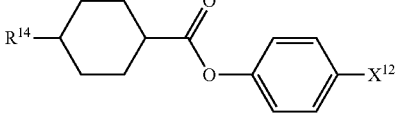

(8-11)

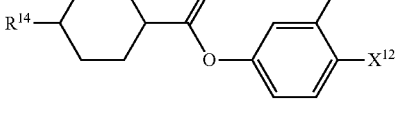

(8-12)

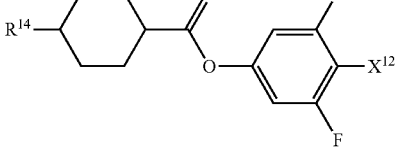

(8-13)

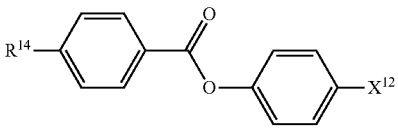

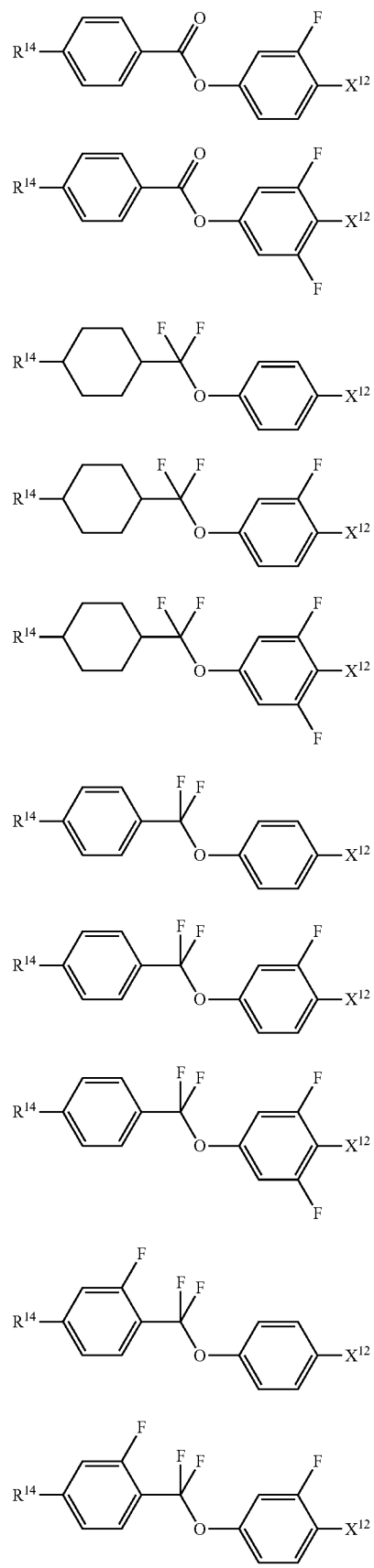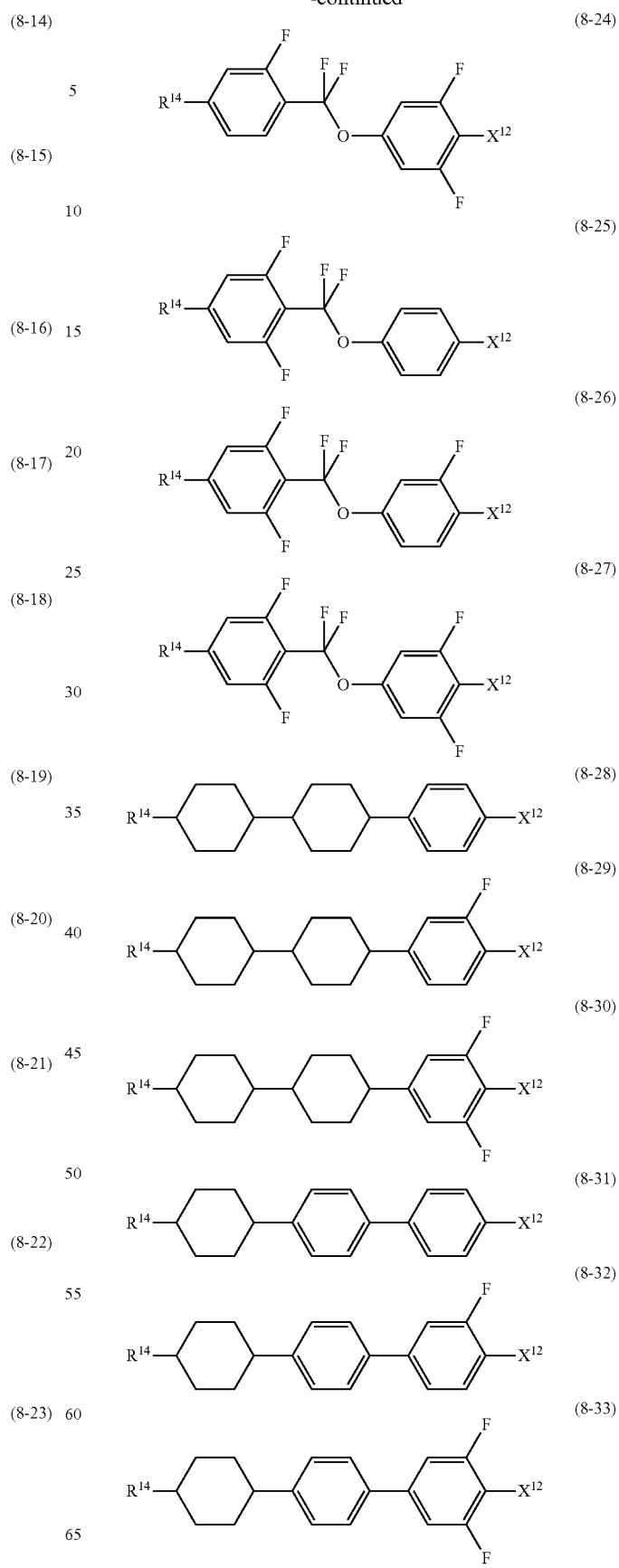

 (8-34)
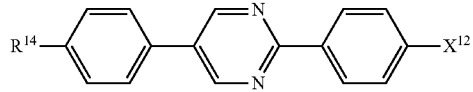 (8-35)
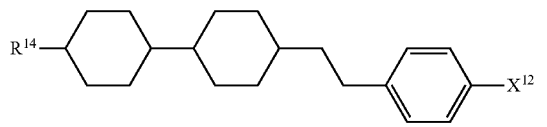 (8-36)
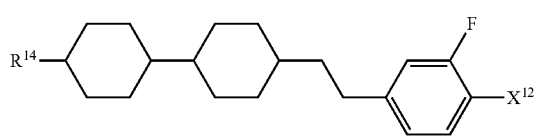 (8-37)
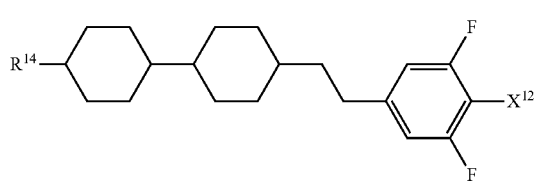 (8-38)
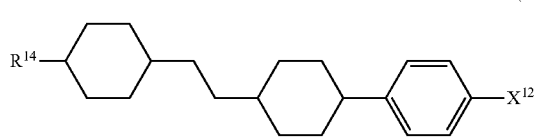 (8-39)
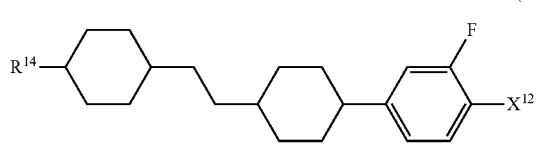 (8-40)
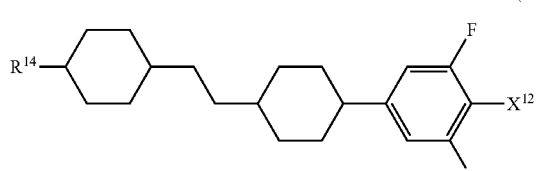 (8-41)
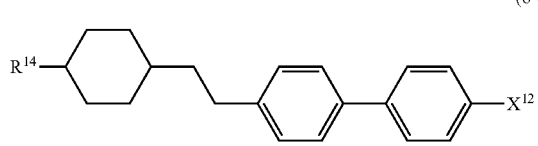 (8-42)
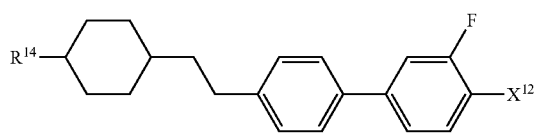 (8-43)
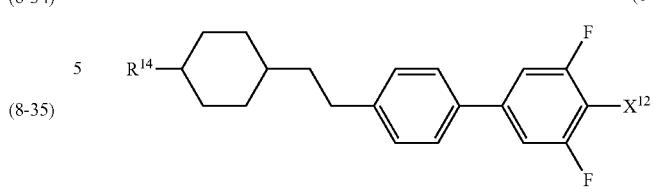 (8-44)
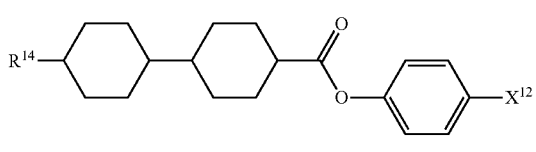 (8-45)
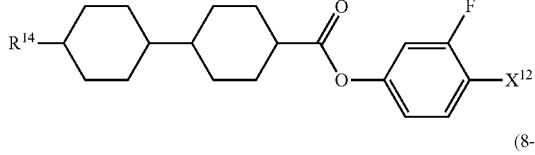 (8-46)
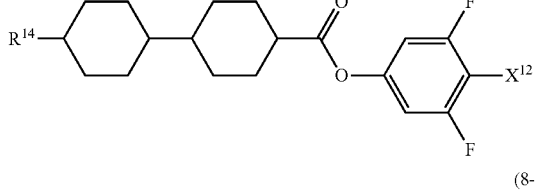 (8-47)
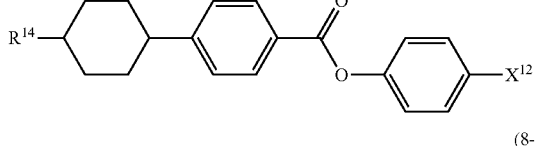 (8-48)
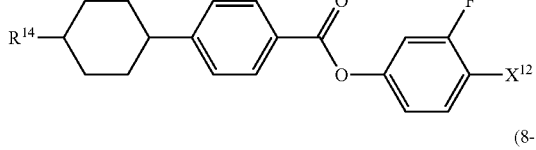 (8-49)
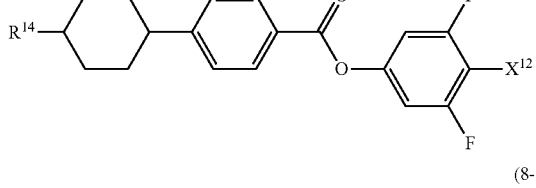 (8-50)
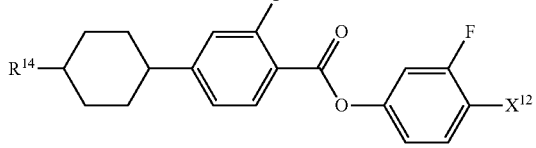 (8-51)
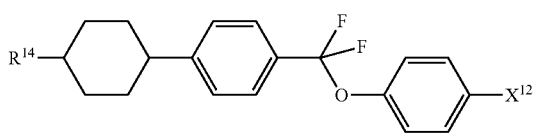 (8-52)

(8-53)
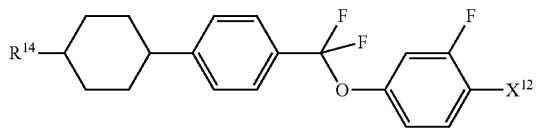

(8-54)
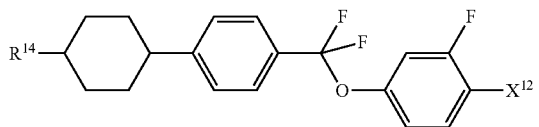

(8-55)
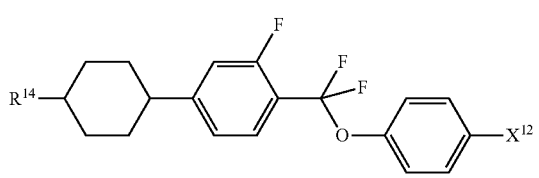

(8-56)
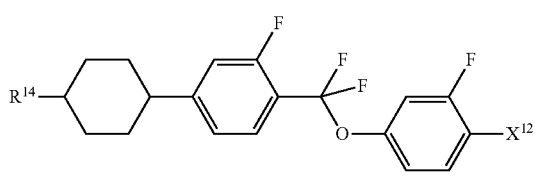

(8-57)
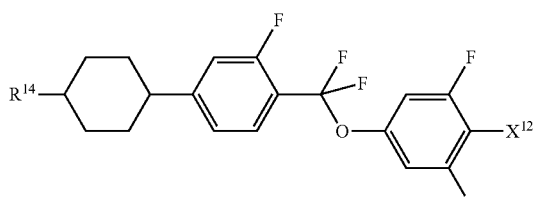

(8-58)
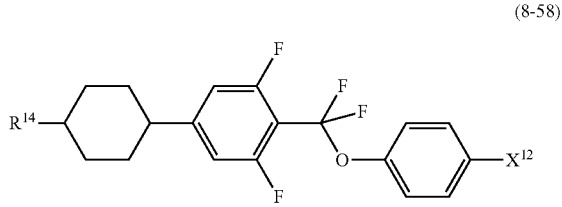

(8-59)
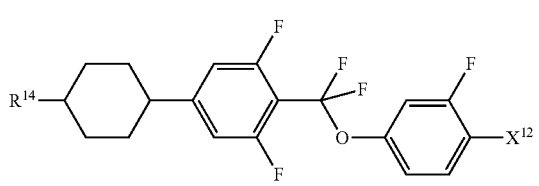

(8-60)
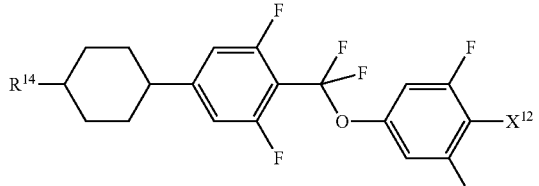

(8-61)
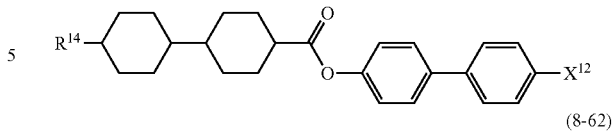

(8-62)
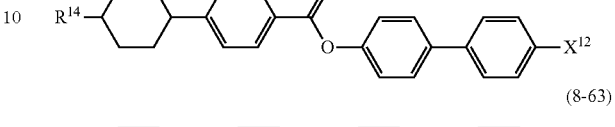

(8-63)
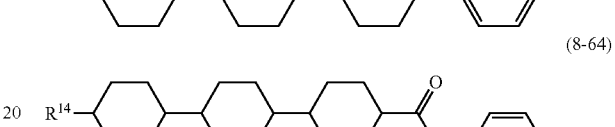

(8-64)
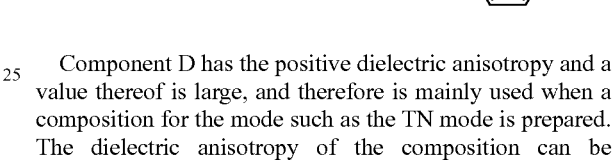

Component D has the positive dielectric anisotropy and a value thereof is large, and therefore is mainly used when a composition for the mode such as the TN mode is prepared. The dielectric anisotropy of the composition can be increased by adding component D thereto. Component D is effective in extending the temperature range of the liquid crystal phase, and adjusting the viscosity or adjusting the optical anisotropy. Component D is also useful for adjusting the voltage-transmittance curve of the device.

When a composition for the TN mode or the like is prepared, a content of component D is suitably in the range of 1% by weight to 99% by weight, preferably in the range of 10% by weight to 97% by weight, and further preferably in the range of 40% by weight to 95% by weight, based on the weight of the liquid crystal composition. When component D is added to a composition having the negative dielectric anisotropy, the content of component D is preferably 30% by weight or less based on the weight of the composition. The elastic constant of the composition and the voltage-transmittance curve of the device can be adjusted by adding component D thereto.

The liquid crystal composition satisfying at least one of physical properties such as the high maximum temperature, the low minimum temperature, the small viscosity, the suitable optical anisotropy, the large dielectric anisotropy, the suitable elastic constant and the large specific resistance can be prepared by suitably combining components B, C and D described above. When necessary, a component different from components B, C and D may be added thereto. Example of such a component includes a compound having 2, 3-difluoro-1,4-phenylene. The compound has the negative dielectric anisotropy. When such a compound is added to a composition having the positive dielectric anisotropy, the elastic constant of the composition and the voltage-transmittance curve of the device can be adjusted.

When compound (1) is added to a mixture of such components, a liquid crystal composition stable to light can be prepared. Preparation of the liquid crystal composition is performed by a method of dissolving required components at a temperature higher than room temperature, or the like.

According to an application, an additive may be added to the composition. Specific examples of the additive include the polymerizable compound, the polymerization initiator, the polymerization inhibitor, the optically active compound, the antioxidant, the ultraviolet light absorber, the light stabilizer, the heat stabilizer and the antifoaming agent. Such additives are well known to those skilled in the art, and described in literature.

The polymerizable compound is added for the purpose of forming the polymer in the composition. The polymerizable compound is polymerized by irradiation with ultraviolet light while voltage is applied between electrodes, and thus the polymer is formed in the liquid crystal composition. A suitable pretilt is obtained by the method, and therefore the liquid crystal display device in which a response time is shortened and the image persistence is improved is obtained. Preferred examples of the polymerizable compound include an acrylate, a methacrylate, a vinyl compound, a vinyloxy compound, a propenyl ether, an epoxy compound (oxirane, oxetane) and a vinyl ketone. Further preferred examples include a compound having at least one piece of acryloyloxy and a compound having at least one piece of methacryloyloxy. Still further preferred examples also include a compound having both acryloyloxy and methacryloyloxy.

Further preferred examples include compounds (M-1) to (M-12). In compounds (M-1) to (M-12), $R^{25}$, $R^{26}$ and $R^{27}$ are independently hydrogen or methyl; u, x and y are independently 0 or 1; v and w are independently an integer from 1 to 10; and $L^{21}$, $L^{22}$, $L^{23}$, $L^{24}$, $L^{25}$ and $L^{26}$ are independently hydrogen or fluorine.

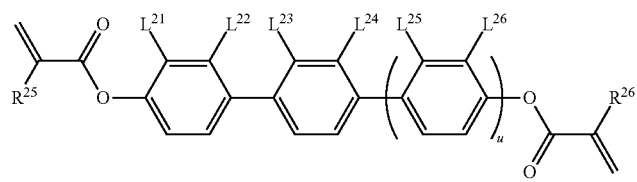

(M-1)

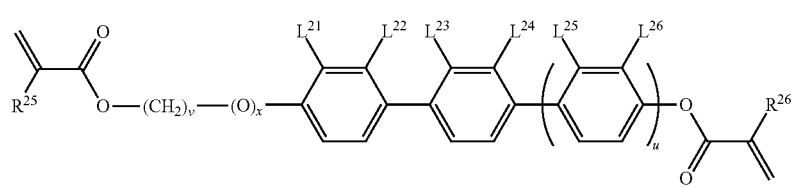

(M-2)

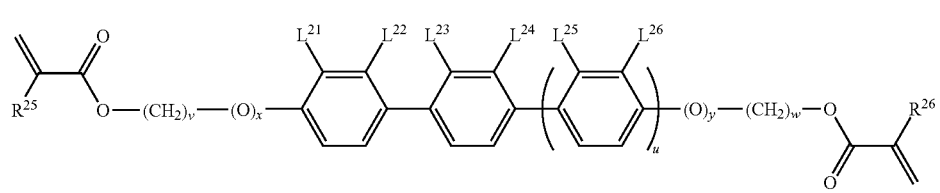

(M-3)

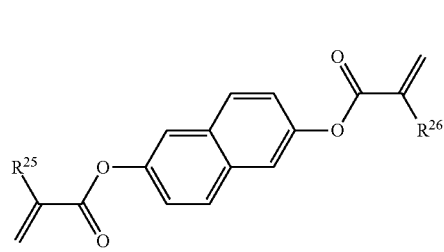

(M-4)

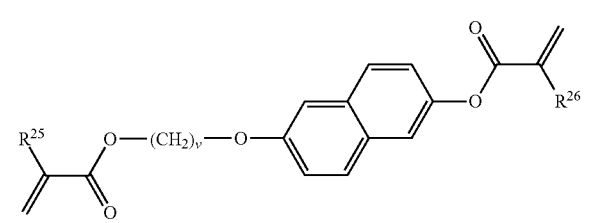

(M-5)

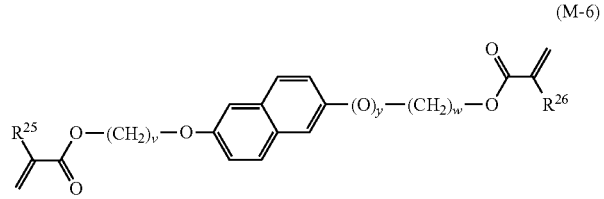

(M-6)

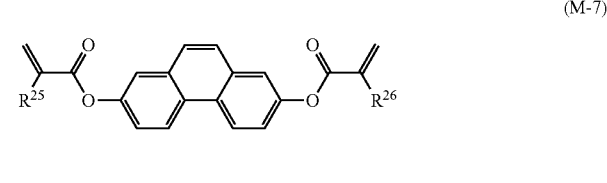

(M-7)

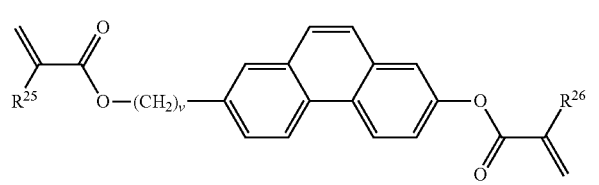

(M-8)

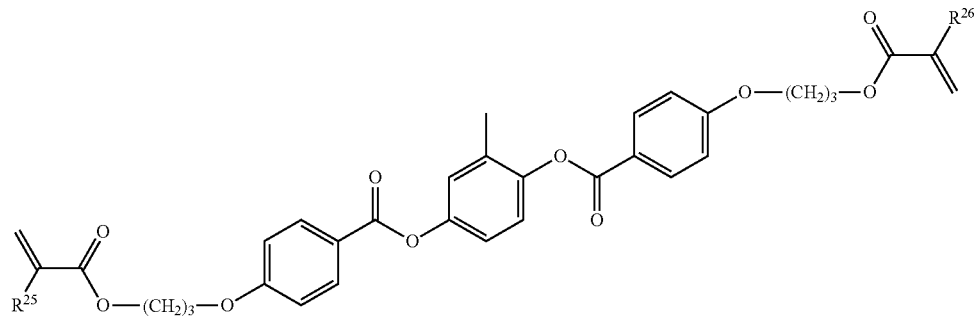

(M-9)

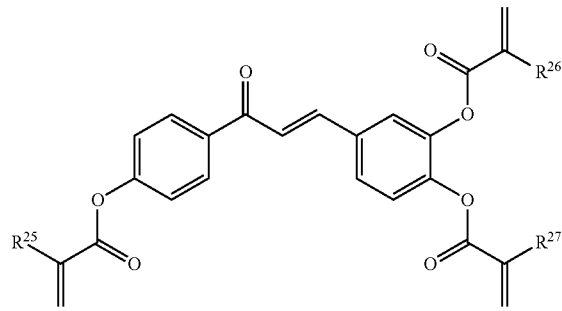

(M-10)

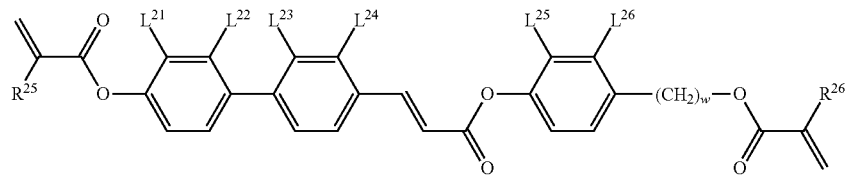

(M-11)

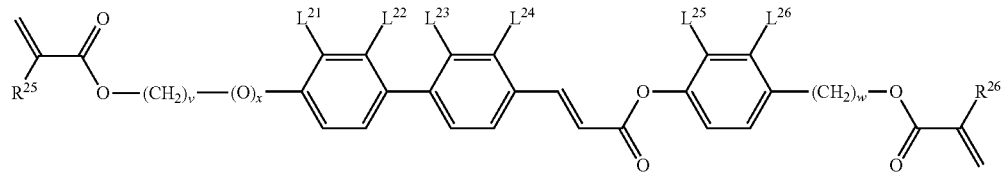

(M-12)

The polymerizable compound can be rapidly polymerized by adding the polymerizable initiator. An amount of a remaining polymerizable compound can be decreased by optimizing a reaction temperature. Specific examples of a photoradical polymerization initiator include TPO, 1173 and 4265 from Darocur series of BASF SE, and 184, 369, 500, 651, 784, 819, 907, 1300, 1700, 1800, 1850, and 2959 from Irgacure series thereof.

Additional examples of the photoradical polymerization initiator include 4-methoxyphenyl-2,4-bis(trichloromethyl) triazine, 2-(4-butoxystyryl)-5-trichloromethyl-1,3,4-oxadiazole, 9-phenylacridine, 9,10-benzphenazine, a benzophenone-Michler's ketone mixture, a hexaarylbiimidazole-mercaptobenzimidazole mixture, 1-(4-isopropylphenyl)-2-hydroxy-2-methylpropane-1-one, benzyl dimethyl ketal, 2-methyl-1-[4-(methylthio)phenyl]-2-morpholinopropane-1-one, a mixture of 2,4-diethylxanthone and methyl p-dimethylaminobenzoate and a mixture of benzophenone and methyltriethanolamine.

After the photoradical polymerization initiator is added to the liquid crystal composition, polymerization can be performed by irradiation with ultraviolet light while an electric field is applied. However, an unreacted polymerization initiator or a decomposition product of the polymerization initiator may cause a poor display such as the image persistence in the device. In order to prevent such an event, photopolymerization may be performed with no addition of the polymerization initiator. A preferred wavelength of light to be irradiated is in the range of 150 nanometers to 500 nanometers. A further preferred wavelength is in the range of 250 nanometers to 450 nanometers, and a most preferred wavelength is in the range of 300 nanometers to 400 nanometers.

Upon storing the polymerizable compound, the polymerization inhibitor may be added thereto for preventing polymerization. The polymerizable compound is ordinarily added to the composition without removing the polymerization inhibitor. Examples of the polymerization inhibitor include hydroquinone, a hydroquinone derivative such as methylhydroquinone, 4-tert-butylcatechol, 4-methoxyphenol and phenothiazine.

The optically active compound is effective in inducing a helical structure in liquid crystal molecules to give a required twist angle, thereby being effective in preventing a reverse twist. A helical pitch can be adjusted by adding the optically active compound thereto. Two or more optically active compounds may be added for the purpose of adjusting temperature dependence of the helical pitch. Preferred examples of the optically active compound include compounds (Op-1) to (Op-18) described below. In compound (Op-18), ring J is 1,4-cyclohexylene or 1,4-phenylene, and $R^{28}$ is alkyl having 1 to 10 carbons.
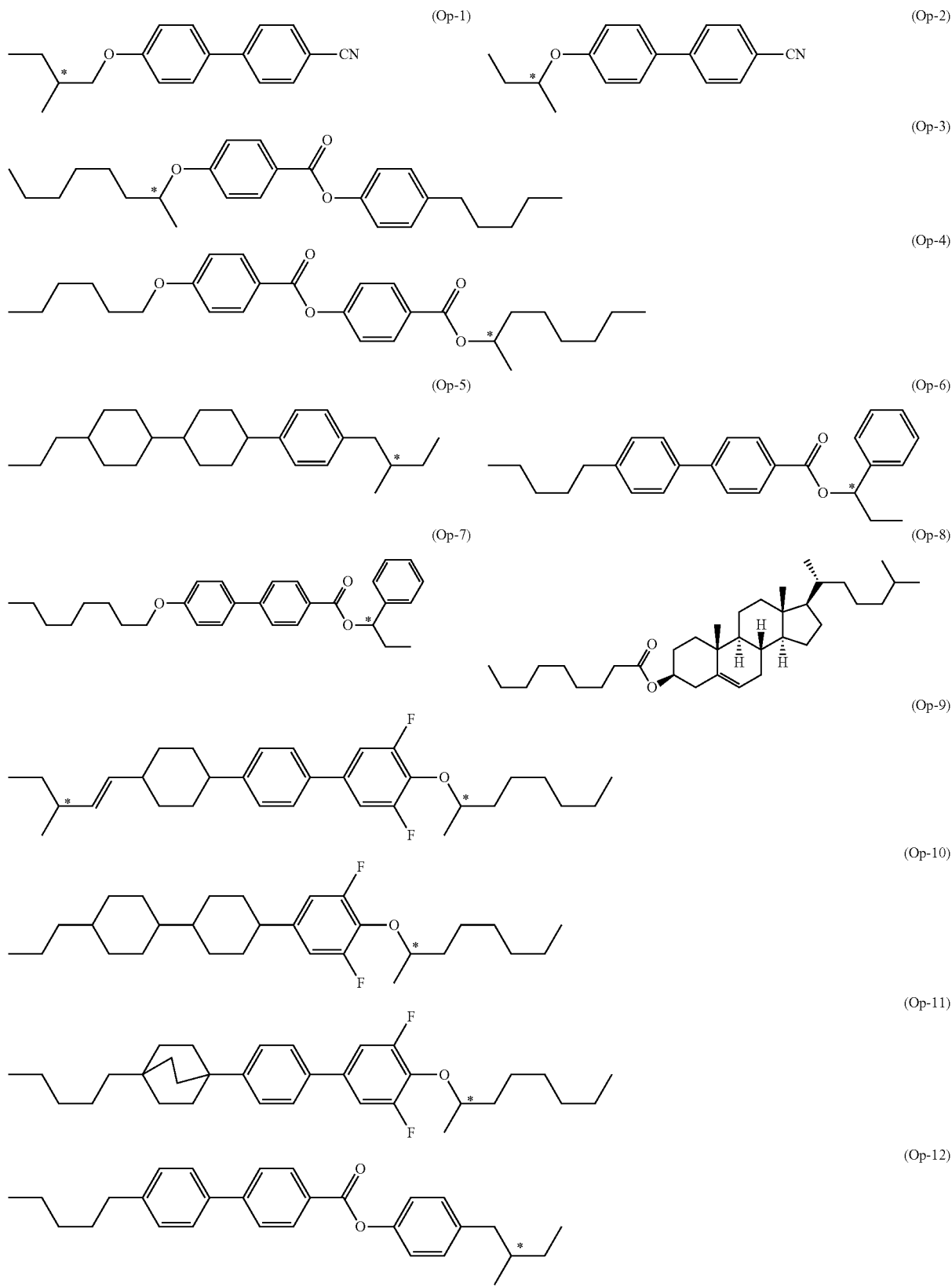

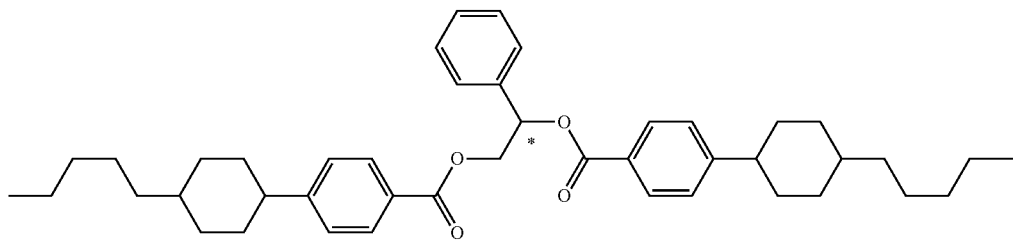

(Op-13)

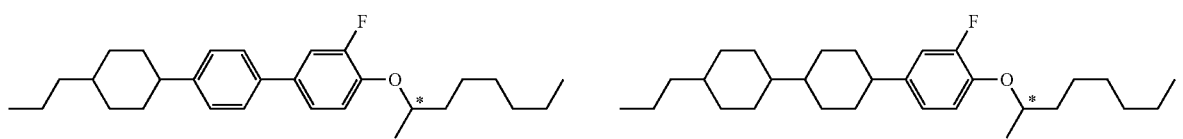

(Op-14) (Op-15)

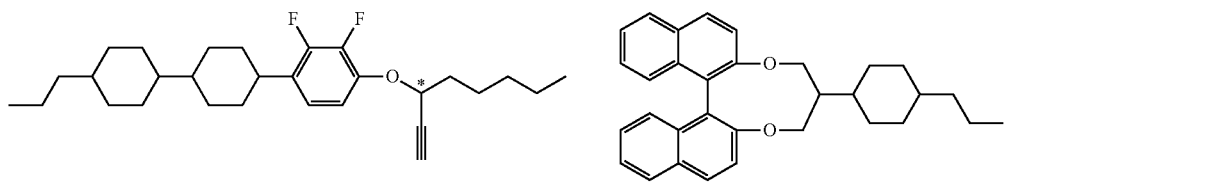

(Op-16) (Op-17)

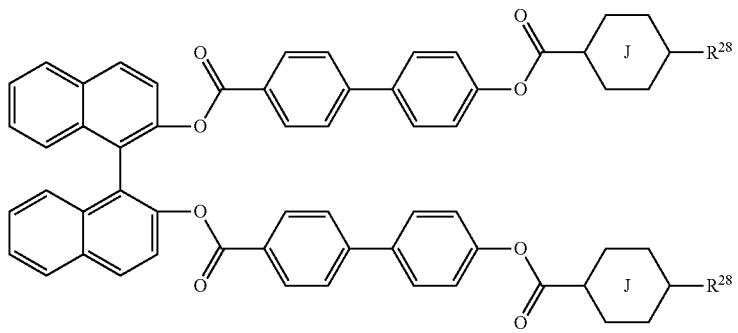

(Op-18)

The antioxidant is effective for maintaining the large voltage holding ratio. Preferred examples of the antioxidant include compounds (AO-1) and (AO-2) below; IRGANOX 415, IRGANOX 565, IRGANOX 1010, IRGANOX 1035, IRGANOX 3114 and IRGANOX 1098 (trade names: BASF SE). The ultraviolet light absorber is effective in preventing a decrease of the maximum temperature. Preferred examples of the ultraviolet light absorber include a benzophenone derivative, a benzoate derivative and a triazole derivative. Specific examples include compounds (AO-3) and (AO-4) below, TINUVIN329, TINUVIN P, TINUVIN 326, TINUVIN 234, TINUVIN 213, TINUVIN 400, TINUVIN 328 and TINUVIN 99-2 (trade names: BASF SE); and 1,4-diazabicyclo[2.2.2]octane (DABCO).

The light stabilizer such as an amine having steric hindrance is preferred for maintaining the large voltage holding ratio. Preferred examples of the light stabilizer include compounds (AO-5) and (AO-6) below; and TINUVIN 144, TINUVIN 765 and TINUVIN 770DF (trade names: BASF SE). Further preferred light stabilizer is compound (1). The heat stabilizer is also effective for maintaining the large voltage holding ratio, and preferred examples include IRGAFOS 168 (trade name: BASF SE). The antifoaming agent is effective in preventing foam formation. Preferred examples of the antifoaming agent include dimethyl silicone oil and methylphenyl silicone oil.

(AO-1)

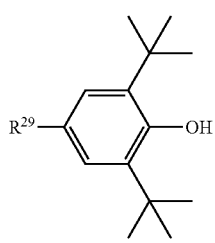

(AO-2)

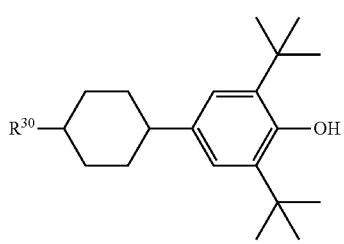

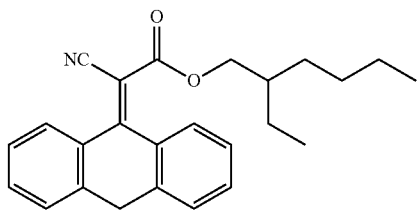

(AO-3)

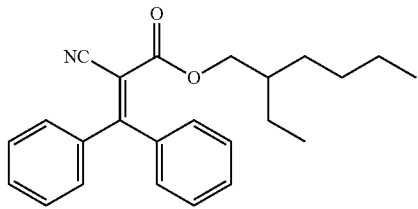

(AO-4)

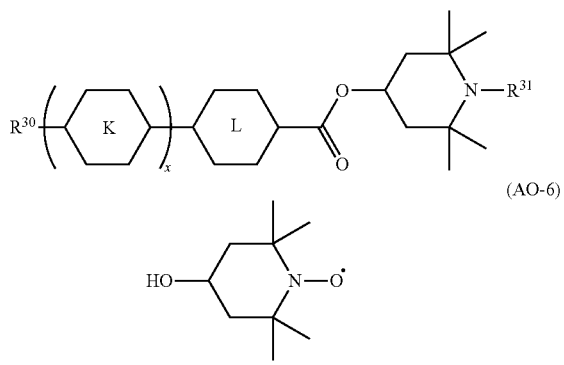

(AO-5)

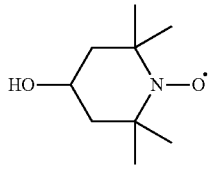

(AO-6)

In compound (AO-1), $R^{29}$ is alkyl having 1 to 20 carbons, alkoxy having 1 to 20 carbons, —COOR$^{32}$ or —CH$_2$CH$_2$COOR$^{32}$, in which $R^{32}$ is alkyl having 1 to 20 carbons. In compounds (AO-2) and (AO-5), $R^{30}$ is alkyl having 1 to 20 carbons. In compound (AO-5), $R^{31}$ is hydrogen, methyl or O. (oxygen radical), and ring K and ring L are 1,4-cyclohexylene or 1,4-phenylene, and x is 0, 1 or 2.

3. Liquid Crystal Display Device

The liquid crystal composition can be used for the liquid crystal display device having an operating mode such as the PC mode, the TN mode, the STN mode, the OCB mode and the PSA mode, and driven by an active matrix (AM mode). The composition can also be used for the liquid crystal display device having the operating mode such as the PC mode, the TN mode, the STN mode, the OCB mode, the VA mode and the IPS mode, and driven by a passive matrix (PM) mode. The AM mode and the PM mode devices can be applied to any of a reflective type, a transmissive type and a transflective type.

The composition can also be used for a nematic curvilinear aligned phase (NCAP) device prepared by microencapsulating a nematic liquid crystal, a polymer dispersed liquid crystal display device (PDLCD) and a polymer network liquid crystal display device (PNLCD), in which a three-dimensional network polymer is formed in the liquid crystal. When an amount of addition of the polymerizable compound is in the range of 0.1% by weight to 2% by weight based on the weight of the liquid crystal composition, the liquid crystal display device having the PSA mode is prepared. The device having the PSA mode can be driven by the driving mode such as the active matrix and the passive matrix. Such a device can be applied to any of the reflective type, the transmissive type and the transflective type. The device having the polymer dispersed mode can also be prepared by increasing an amount of adding the polymerizable compound.

EXAMPLES

The invention will be described in greater detail by way of Examples. The invention is not limited by the Examples.

1. Example of Compound (1)

Compound (1) was prepared according to procedures described in Examples. Unless otherwise described, a reaction was performed under a nitrogen atmosphere. Compound (1) was prepared according to procedures described in Example 1 or the like. The synthesized compound was identified by methods such as an NMR analysis. Physical properties of the compound were measured by methods described below.

NMR Analysis

For measurement, DRX-500 made by Bruker BioSpin Corporation was used. In $^1$H-NMR measurement, a sample was dissolved in a deuterated solvent such as CDCl$_3$, and measurement was carried out under conditions of room temperature, 500 MHz and 16 times of accumulation. Tetramethylsilane was used as an internal standard. In $^{19}$F-NMR measurement, measurement was carried out under conditions of 24 times of accumulation using CFCl$_3$ as an internal standard. In the explanation of a nuclear magnetic resonance spectrum, s, d, t, q, quin, sex and m stand for a singlet, a doublet, a triplet, a quartet, a quintet, a sextet and a multiplet, respectively, and br means being broad.

GC Analysis

GC-2010 Gas Chromatograph made by Shimadzu Corporation was used for measurement. A capillary column DB-1 (length 60 m, bore 0.25 mm, film thickness 0.25 μm) made by Agilent Technologies, Inc. was used. Helium was used as a carrier gas, and a flow rate was adjusted to 1 mL per minute. A temperature of a sample vaporizing chamber and a detector (FID) part were set to 300° C. and 300° C., respectively. A sample was dissolved in acetone and prepared to be a 1 weight % solution, and then 1 microliter of the solution obtained was injected into the sample injector. A recorder such as GC Solution System made by Shimadzu Corporation was used.

HPLC Analysis

For measurement, Prominence (LC-20 AD; SPD-20A) made by Shimadzu Corporation was used. As a column, YMC-Pack ODS-A (length: 150 mm, inner diameter: 4.6 mm, particle diameter: 5 μm) made by YMC GmbH was used. As an eluate, acetonitrile and water were appropriately mixed and used. As a detector, a UV detector, an RI detector, a CORONA detector or the like was appropriately used. When the UV detector was used, a detection wavelength was adjusted to 254 nm. A sample was dissolved in acetonitrile and prepared to be a 0.1 weight % solution, and then 1 microliter of the solution was injected into the sample chamber. As a recorder, C-R7Aplus made by Shimadzu Corporation was used.

Ultraviolet-Visible Spectrophotometry

For measurement, PharmaSpec UV-1700 made by Shimadzu Corporation was used. A detection wavelength was adjusted in the range from 190 nm to 700 nm. A sample was dissolved in acetonitrile, and prepared to be a solution of 0.01 mmol/L, and measurement was carried out by putting the solution in a quartz cell (optical path length 1 cm).

Sample for Measurement:

Upon measuring phase structure and a transition temperature (a clearing point, a melting point, a polymerization starting temperature or the like), a liquid crystal compound itself was used as a sample. Upon measuring physical properties such as a maximum temperature of a nematic phase, viscosity, optical anisotropy and dielectric anisotropy, a mixture of a compound and a base liquid crystal was used as a sample.

Measuring Methods

Physical properties were measured by methods described below. Most of the measuring methods are applied as described in the Standard of the Japan Electronics and Information Technology Industries Association (JEITA EIAJ ED-2521B) discussed and established by JEITA, or modified thereon. No thin film transistor (TFT) was attached to a TN device used for measurement.

(1) Phase Structure

A sample was placed on a hot plate of a melting point apparatus (FP-52 Hot Stage made by Mettler-Toledo International Inc.) equipped with a polarizing microscope, and a state of phase and a change thereof were observed with the polarizing microscope while the sample was heated at a rate of 3° C. per minute, and a kind of the phase was specified.

(2) Transition Temperature (° C.)

For measurement, a scanning calorimeter, Diamond DSC System, made by PerkinElmer, Inc., or a high-sensitivity differential scanning calorimeter, X-DSC7000, made by SII NanoTechnology Inc. was used. A sample was heated and then cooled at a rate of 3° C. per minute, and a starting point of an endothermic peak or an exothermic peak caused by a phase change of the sample was determined by extrapolation, and thus a transition temperature was determined. A polymerization starting temperature and a melting point of a compound were also measured using the apparatus. Temperature at which a compound undergoes transition from a solid to a liquid crystal phase such as the smectic phase and the nematic phase may be occasionally abbreviated as "minimum temperature of the liquid crystal phase." Temperature at which the compound undergoes transition from the liquid crystal phase to the liquid may be occasionally abbreviated as "clearing point."

A crystal was expressed as C. When kinds of the crystals were distinguishable, each of the crystals was expressed as $C_1$ or $C_2$. The smectic phase or the nematic phase was expressed as S or N. When smectic A phase, smectic B phase, smectic C phase or smectic F phase was distinguishable among the smectic phases, the phases were expressed as $S_A$, $S_B$, $S_C$ or $S_F$, respectively. A liquid (isotropic) was expressed as I. A transition temperature was expressed as "C, 50.0; N, 100.0; I," for example. The expression indicates that a transition temperature from the crystals to the nematic phase is 50.0° C., and a transition temperature from the nematic phase to the liquid is 100.0° C.

(3) Maximum Temperature of Nematic Phase ($T_{NI}$ or NI; ° C.)

A sample was placed on a hot plate in a melting point measuring apparatus equipped with a polarizing microscope and was heated at a rate of 1° C. per minute. Temperature when part of the sample began to change from a nematic phase to an isotropic liquid was measured. A higher limit of a temperature range of the nematic phase may be occasionally abbreviated as "maximum temperature." When the sample was a mixture of compound (1) and the base liquid crystal, the maximum temperature was expressed using a symbol $T_{NI}$. When the sample was a mixture of compound (1) and a compound such as components B, C and D, the maximum temperature was expressed using a symbol NI.

(4) Minimum Temperature of Nematic Phase ($T_C$; ° C.)

Samples each having a nematic phase were kept in freezers at temperatures of 0° C., −10° C., −20° C., −30° C. and −40° C. for 10 days, and then liquid crystal phases were observed. For example, when the sample maintained the nematic phase at −20° C. and changed to the crystals or the smectic phase at −30° C., $T_C$ was expressed as $T_C \leq -20°$ C. A lower limit of the temperature range of the nematic phase may be occasionally abbreviated as "minimum temperature."

(5) Viscosity (Bulk Viscosity; η; Measured at 20° C.; mPa·s)

A cone-plate (E type) rotational viscometer made by Tokyo Keiki Inc. was used for measurement.

(6) Optical Anisotropy (Refractive Index Anisotropy; Measured at 25° C.; Δn)

Measurement was carried out by an Abbe refractometer having a polarizing plate mounted on an ocular, using light at a wavelength of 589 nm. A surface of a main prism was rubbed in one direction, and then a sample was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of optical anisotropy was calculated from an equation: Δn=n∥−n⊥.

(7) Specific Resistance (ρ; Measured at 25° C.; Ω Cm)

Into a vessel provided with electrodes, 1.0 milliliter of sample was injected. Direct current voltage (10 V) was applied to the vessel, and a direct current after 10 seconds was measured. The specific resistance was calculated from the following equation: (Specific resistance)={(voltage)×(electric capacity of a vessel)}/{(direct current)×(dielectric constant of a vacuum)}.

(8) Voltage Holding Ratio (VHR-1; Measured at 25° C.; %)

A TN device used for measurement had a polyimide alignment film and a distance (cell gap) between two glass substrates was 5 micrometers. A sample was put in the device, and then the device was sealed with an ultraviolet-curable adhesive. The device was charged by applying a pulse voltage (60 microseconds at 5 V). A decaying voltage was measured for 16.7 milliseconds with a high-speed voltmeter, and area A between a voltage curve and a horizontal axis in a unit cycle was determined. Area B was an area without decay. A voltage holding ratio is expressed in terms of a percentage of area A to area B.

(9) Voltage Holding Ratio (VHR-2; Measured at 80° C.; %)

A voltage holding ratio was measured in procedures identical with the procedures described above except that the voltage holding ratio was measured at 80° C. in place of 25° C. The results obtained were expressed using a symbol VHR-2.

Methods for measuring characteristics may be occasionally different between a sample having positive dielectric anisotropy and a sample having negative dielectric anisotropy. The measurement method in positive dielectric anisotropy was described in sections (10) to (14).

(10) Viscosity (Rotational Viscosity; γ1; Measured at 25° C.; mPa·s)

Measurement was carried out according to a method described in M. Imai et al., Molecular Crystals and Liquid Crystals, Vol. 259, 37 (1995). A sample was put in a TN device in which a twist angle was 0 degrees and a distance (cell gap) between two glass substrates was 5 micrometers. A voltage was applied stepwise to the device in the range of 16 V to 19.5 V at an increment of 0.5 V. After a period of 0.2 second with no voltage application, voltage was repeatedly applied under conditions of only one rectangular wave (rectangular pulse; 0.2 second) and no voltage application (2 seconds). A peak current and a peak time of a transient current generated by the applied voltage were measured. A value of rotational viscosity was obtained from the measured values and calculation equation (8) on page 40 of the paper presented by M. Imai et al. A value of dielectric anisotropy required for the calculation was determined using the device by which the rotational viscosity was measured and by a method described below.

(11a) Dielectric Anisotropy (Δε; Measured at 25° C.)

A sample was put in a TN device in which a distance (cell gap) between two glass substrates was 9 micrometers and a twist angle was 80 degrees. Sine waves (10 V, 1 kHz) were applied to the device, and after 2 seconds, a dielectric constant ($\varepsilon\parallel$) in a major axis direction of liquid crystal molecules was measured. Sine waves (0.5 V, 1 kHz) were applied to the device, and after 2 seconds, a dielectric constant ($\varepsilon\perp$) in a minor axis direction of the liquid crystal molecules was measured. A value of dielectric anisotropy was calculated from an equation: $\Delta\varepsilon=\varepsilon\parallel-\varepsilon\perp$.

(12) Elastic Constant (K; Measured at 25° C.; pN)

HP4284A LCR Meter made by Yokogawa-Hewlett-Packard Co. was used for measurement. A sample was put in a horizontal alignment device in which a distance (cell gap) between two glass substrates was 20 micrometers. An electric charge of 0 V to 20 V was applied to the device, and electrostatic capacity and applied voltage were measured. The measured values of electrostatic capacity (C) and applied voltage (V) were fitted to equation (2.98) and equation (2.101) on page 75 of "Liquid Crystal Device Handbook" (Ekisho Debaisu Handobukku in Japanese; The Nikkan Kogyo Shimbun, Ltd.), and values of $K_{11}$ and $K_{33}$ were obtained from equation (2.99). Next, $K_{22}$ was calculated using the previously determined values of $K_{11}$ and $K_{33}$ in formula (3.18) on page 171. Elastic constant K was expressed using a mean value of thus determined $K_{11}$, $K_{22}$ and $K_{33}$.

(13) Threshold Voltage (Vth; Measured at 25° C.; V)

An LCD-5100 luminance meter made by Otsuka Electronics Co., Ltd. was used for measurement. A light source was a halogen lamp. A sample was put in a normally white mode TN device in which a distance (cell gap) between two glass substrates was 0.45/An (μm) and a twist angle was 80 degrees. A voltage (32 Hz, rectangular waves) to be applied to the device was stepwise increased from 0 V to 10 V at an increment of 0.02 V. On the occasion, the device was irradiated with light from a perpendicular direction, and an amount of light transmitted through the device was measured. A voltage-transmittance curve was prepared, in which a maximum value of the amount of light corresponded to 100% transmittance and a minimum value of an amount of light corresponded to 0% transmittance. A threshold voltage is expressed in terms of a voltage at 90% transmittance.

(14a) Response Time (τ; Measured at 25° C.; Ms)

An LCD-5100 luminance meter made by Otsuka Electronics Co., Ltd. was used for measurement. A light source was a halogen lamp. A low-pass filter was set to 5 kHz. A sample was put in a normally white mode TN device in which a distance (cell gap) between two glass substrates was 5.0 micrometers and a twist angle was 80 degrees. Rectangular waves (60 Hz, 5 V, 0.5 second) were applied to the device. On the occasion, the device was irradiated with light from a perpendicular direction, and an amount of light transmitted through the device was measured. The maximum amount of light corresponded to 100% transmittance, and the minimum amount of light corresponded to 0% transmittance. A rise time (τr: rise time; millisecond) is a period of time required for a change in transmittance from 90% to 10%. A fall time (τf: fall time; millisecond) is a period of time required for a change in transmittance from 10% to 90%. A response time was expressed by a sum of the rise time and the fall time thus obtained.

Example 1

Synthesis of 1,4-bis(2,2,6,6-tetramethylpiperidine-4-yl)benzene (No. 1)

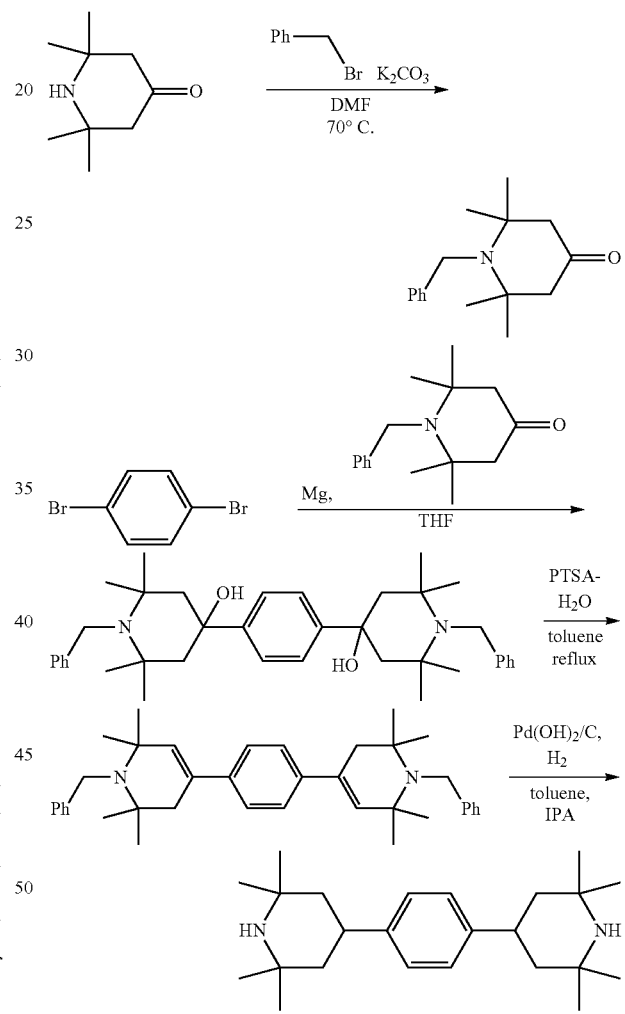

1

First Step:

A mixture of 2,2,6,6-tetramethylpiperidine-4-one (2.00 g, 12.88 mmol), bromomethylbenzene (2.64 g, 15.43 mmol) and potassium carbonate (3.56 g, 25.77 mmol) was heated and stirred in DMF at 70° C. for 8 hours. The resulting reaction mixture was poured into water and subjected to extraction with toluene. A combined organic layer was washed with a 1 N hydrochloric acid aqueous solution, water and saturated brine, and dried over anhydrous magnesium sulfate. The solvent was distilled off to obtain 1-benzyl-2,2,6,6-tetramethylpiperidine-4-one (2.53 g, yield 80.10).

Second Step:

A THF solution of 1,4-dibromobenzene (1.34 g, 5.68 mmol) was slowly added dropwise to a THF suspension of magnesium (0.15 g, 6.25 mmol), while keeping solution temperature at 50° C. or lower. The Grignard reagent obtained was cooled in an ice bath, and a THF solution of 1-benzyl-2,2,6,6-tetramethylpiperidine-4-one (2.53 g, 10.31 mmol) obtained in the first step was slowly added dropwise thereto, while keeping solution temperature at 10° C. or lower. After stirring the reaction mixture at room temperature for 1 hour, the mixture was quenched in an ammonium chloride aqueous solution, and subjected to extraction with toluene. A combined organic layer was washed with water and saturated brine, and dried over anhydrous magnesium sulfate, and a solvent was distilled off. A residue was purified by silica gel chromatography to obtain 4,4'-(1,4-phenylene)bis(1-benzyl-2,2,6,6-tetramethylpiperidine-4-ol) (4.63 g, 7.89 mmol).

Third Step:

In a reactor equipped with a Dean-Stark condenser, 4,4'-(1,4-phenylene)bis(1-benzyl-2,2,6,6-tetramethylpiperidine-4-ol) obtained in the second step (4.63 g, 7.89 mmol), p-toluenesulfonic acid hydrate (0.046 g, 0.24 mmol) and toluene were put, and the resulting mixture was refluxed for 3 hours. The reaction mixture was washed with a saturated aqueous solution of sodium hydrogen carbonate, water and saturated brine, dried over anhydrous magnesium sulfate, and the solvent was distilled off. The residue was purified by silica gel chromatography to obtain 1,4-bis(1-benzyl-2,2,6,6-tetramethyl-1,2,3,6-tetrahydropyridine-4-yl)benzene (3.62 g, yield 86.1%).

Fourth Step:

A mixture of 1,4-bis(1-benzyl-2,2,6,6-tetramethyl-1,2,3,6-tetrahydropyridine-4-yl)benzene obtained in the third step (3.62 g, 6.79 mmol) and 5% palladium hydroxide/carbon (0.11 g, 3 wt %) was stirred in a mixed solvent of toluene-isopropyl alcohol under a hydrogen atmosphere for 18 hours. The resulting reaction mixture was subjected to filtration and the solvent of the filtrate was distilled off. The residue was purified by silica gel chromatography and recrystallization to obtain 1,4-bis(2,2,6,6-tetramethylpiperidine-4-yl)benzene (1.34 g, yield 56%).

$^1$H-NMR (CDCl$_3$; δ ppm): 7.17 (s, 4H), 3.00 (tt, 2H), 1.77 (dd, 4H), 1.71-1.59 (br, 1H), 1.31-1.23 (m, 16H), 1.15 (s, 12H), 0.78-0.67 (br, 1H).

Example 2

Synthesis of 4,4-(3-fluoro-[1,1'-biphenyl]-4,4'-diyl)bis(2,2,6,6-tetramethylpiperidine) (No. 23)

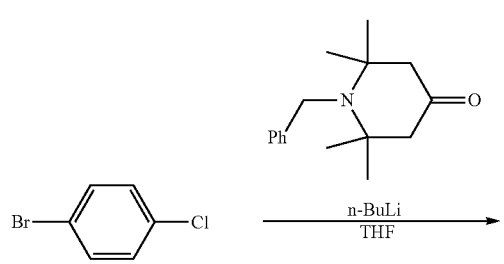

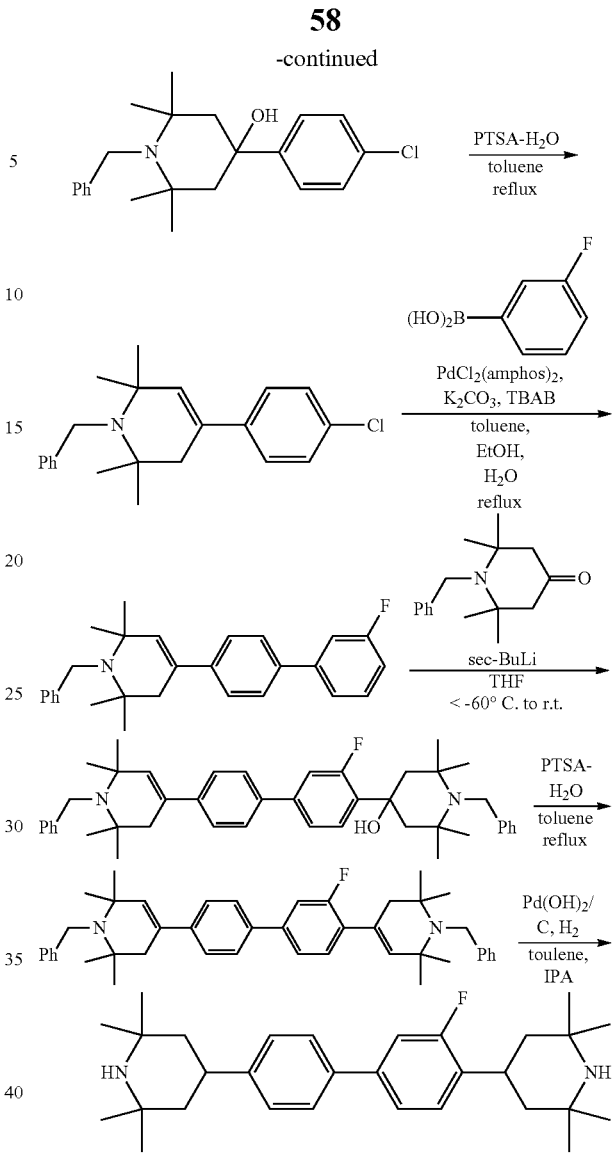

First Step:

To a THF solution of 1-bromo-4-chlorobenzene (10.0 g, 52.2 mmol), n-butyllithium (1.61 mol/l, 35.7 ml, 57.5 mmol) was added dropwise, while keeping solution temperature at −60° C. or lower. The resulting mixture was stirred for 1 hour at the same temperature, and then a THF solution of 1-benzyl-2,2,6,6-tetramethylpiperidine-4-one (14.1 g, 57.46 mmol) was added dropwise thereto. The resulting reaction mixture was returned to room temperature, and the mixture was quenched in an ammonium chloride aqueous solution and subjected to extraction with toluene. A combined organic layer was washed with water and saturated brine, and dried over anhydrous magnesium sulfate, and a solvent was distilled off. The residue was purified by silica gel chromatography to obtain 1-benzyl-4-(4-chlorophenyl)-2,2,6,6-tetramethylpiperidine-4-ol (15.5 g, yield 82.9%).

Second Step:

In a reactor equipped with a Dean-Stark condenser, 1-benzyl-4-(4-chlorophenyl)-2,2,6,6-tetramethylpiperidine-4-ol obtained in the first step (15.5 g, 43.3 mmol), p-toluenesulfonic acid hydrate (0.16 g, 0.84 mmol) and toluene were put, and the resulting mixture was refluxed for 3 hours. The reaction mixture was washed with a saturated aqueous solution of sodium hydrogen carbonate, water and saturated brine, dried over anhydrous magnesium sulfate, and the solvent was distilled off. The residue was purified by silica gel chromatography to obtain 1-benzyl-4-(4-chlorophenyl)-2,2,6,6-tetramethyl-1,2,3,6-tetrahydropyridine (12.8 g, yield 86.9%).

Third Step:

A mixture of 1-benzyl-4-(4-chlorophenyl)-2,2,6,6-tetramethyl-1,2,3,6-tetrahydropyridine (12.8 g, 37.7 mmol), (3-fluorophenyl) boronic acid (5.8 g, 41.5 mmol), bis(di-tert-butyl(4-dimethylaminophenyl)phosphine)dichloropalladium(I I) (PdCl$_2$(amphos)$_2$; 53.3 mg, 75.4 µmol), potassium carbonate (7.81 g, 56.5 mmol) and tetrabutylammonium bromide (2.43 g, 7.54 mmol) obtained in the second step was refluxed for 3 hours in a mixed solvent of toluene-ethanol-water. An organic layer was washed with water and saturated brine, and dried over anhydrous magnesium sulfate, and a solvent was distilled off. The residue was purified by silica gel chromatography to obtain 1-benzyl-4-(3'-fluoro[1,1'-biphenyl]-4-yl)-2,2,6,6-tetramethyl-1,2,3, 6-tetrahydropyridine (14.0 g, yield 93.0%).

Fourth Step:

To a THF solution of 1-benzyl-4-(3'-fluoro[1,1'-biphenyl]-4-yl)-2,2,6,6-tetramethyl-1,2,3, 6-tetrahydropyridine obtained in the third step (14.0 g, 35.0 mmol), sec-butyllithium (1.01 mol/l, 38.1 ml, 38.5 mmol) was added dropwise, while keeping solution temperature at −60° C. or lower. The resulting mixture was stirred for 1 hour at the same temperature, and then a THF solution of 1-benzyl-2,2,6,6-tetramethylpiperidine-4-one (8.60 g, 35.1 mmol) was added dropwise thereto. The resulting reaction mixture was returned to room temperature, and the mixture was quenched in an ammonium chloride aqueous solution and subjected to extraction with toluene. A combined organic layer was washed with water and saturated brine, and dried over anhydrous magnesium sulfate, and a solvent was distilled off. The residue was purified by silica gel chromatography to obtain 1-benzyl-4-(4'-(1-benzyl-2,2,6,6-tetramethyl-1,2,3,6-tetrahydropyridine-4-yl)-3-fluoro-[1,1'-biphenyl]-4-yl)-2,2,6,6-tetramethylpiperidine (13.6 g, yield 60.2%).

Fifth Step:

In a reactor equipped with a Dean-Stark condenser, 1-benzyl-4-(4'-(1-benzyl-2,2,6,6-tetramethyl-1,2,3,6-tetrahydropyridine-4-yl)-3-fluoro-[1,1'-biphenyl]-4-yl)-2,2,6,6-tetramethylpiperidine (13.6 g, 21.1 mmol), p-toluenesulfonic acid hydrate (0.14 g, 0.74 mmol) and toluene were put, and the resulting mixture was refluxed for 3 hours. The reaction mixture was washed with a saturated aqueous solution of sodium hydrogen carbonate, water and saturated brine, dried over anhydrous magnesium sulfate, and the solvent was distilled off. The residue was purified by silica gel chromatography to obtain 4,4-(3-fluoro-[1,1'-biphenyl]-4,4'-diyl)bis(1-benzyl-2,2,6,6-tetramethyl-1,2,3,6-tetrahydropyridine) (9.5 g, yield 71.9%).

Sixth Step:

A mixture of 4,4-(3-fluoro-[1,1'-biphenyl]-4,4'-diyl)bis(1-benzyl-2,2,6,6-tetramethyl-1,2,3,6-tetrahydropyridine) obtained in the fifth step and 5% palladium hydroxide/carbon (0.11 g, 3 wt o) was stirred in a mixed solvent of toluene-isopropyl alcohol under a hydrogen atmosphere for 18 hours. The resulting reaction mixture was subjected to filtration and the solvent of the filtrate was distilled off. The residue was purified by silica gel chromatography and recrystallization to obtain 4,4'-(3-fluoro-[1,1'-biphenyl]-4,4'-diyl)bis(2,2,6,6-tetramethylpiperidine) (1.6 g, yield 44.9%).

$^1$H-NMR (CDCl$_3$; δ ppm): 7.56-7.52 (m, 2H), 7.37-7.25 (m, 5H), 3.47 (tt, 1H), 3.09 (tt, 1H), 1.86-1.78 (m, 4H), 1.40-1.30 (m, 17H), 1.20 (s, 12H), 0.83-0.68 (br, 1H).

Example 3

Synthesis of 4,4'-bis(2,2,6,6-tetramethylpiperidine-4-yl)-1,1'-biphenyl (No. 22)

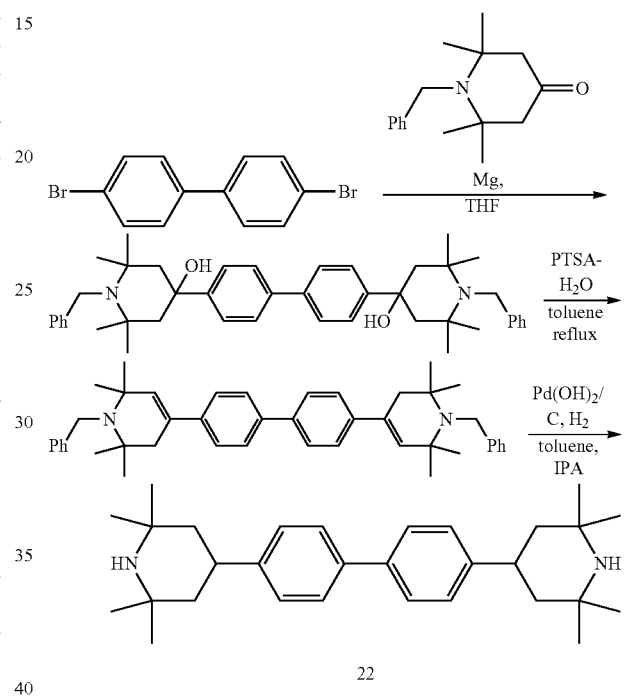

22

First Step:

A THF solution of 4,4'-dibromo-1,1'-biphenyl (10.0 g, 32.0 mmol) was slowly added dropwise to a THF suspension of magnesium (1.64 g, 67.3 mmol), while keeping solution temperature at 50° C. or lower. The Grignard reagent obtained was cooled in an ice bath, and a THF solution of 1-benzyl-2,2,6,6-tetramethylpiperidine-4-one (16.5 g, 67.3 mmol) was added dropwise thereto. After stirring the reaction mixture at room temperature for 1 hour, the mixture was quenched in an ammonium chloride aqueous solution, and subjected to extraction with toluene. A combined organic layer was washed with water and saturated brine, and dried over anhydrous magnesium sulfate, and a solvent was distilled off. The residue was purified by silica gel chromatography to obtain 4,4'-([1,1'-biphenyl]-4,4'-diyl)bis(1-benzyl-2,2,6,6-tetramethylpiperidine-4-ol) (14.9 g, yield 72.6%).

Second Step:

In a reactor equipped with a Dean-Stark condenser, 4,4'-([1,1'-biphenyl]-4,4'-diyl)bis(1-benzyl-2,2,6,6-tetramethylpiperidine-4-ol) (14.9 g, 23.1 mmol) obtained in the first step, p-toluenesulfonic acid hydrate (0.044 g, 0.23 mmol) and toluene were put, and the resulting mixture was refluxed for 3 hours. The reaction mixture was washed with a saturated aqueous solution of sodium hydrogen carbonate, water and saturated brine, dried over anhydrous magnesium sulfate, and the solvent was distilled off. The residue was purified by silica gel chromatography to obtain 4,4'-bis(1-benzyl-2,2,6,6-tetramethyl-1,2,3,6-tetrahydropyridine-4-yl)-1,1'-biphenyl (11.4 g, yield 81.0%).

Third Step:

A mixture of 1,4-bis(1-benzyl-2,2,6,6-tetramethyl-1,2,3,6-tetrahydropyridine-4-yl)benzene (11.4 g, 18.7 mmol) obtained in the second step and 5% palladium hydroxide/carbon (0.34 g, 3 wt %) was stirred in a mixed solvent of toluene-isopropyl alcohol under a hydrogen atmosphere for 18 hours. The resulting reaction mixture was subjected to filtration and the solvent of the filtrate was distilled off. The residue was purified by silica gel chromatography and recrystallization to obtain 4,4'-bis(2,2,6,6-tetramethylpiperidine-4-yl)-1,1'-biphenyl (4.5 g, yield 56%).

$^1$H-NMR (CDCl$_3$; δ ppm): 7.53 (dd, 4H), 7.29 (dd, 4H), 3.07 (tt, 2H), 1.81 (dd, 4H), 1.36-1.26 (m, 17H), 1.17 (s, 12H), 0.95-0.50 (br, 1H).

Example 4

Synthesis of 1,4-bis((2,2,6,6-tetramethylpiperidine-4-yl)methoxy)benzene (No. 9)

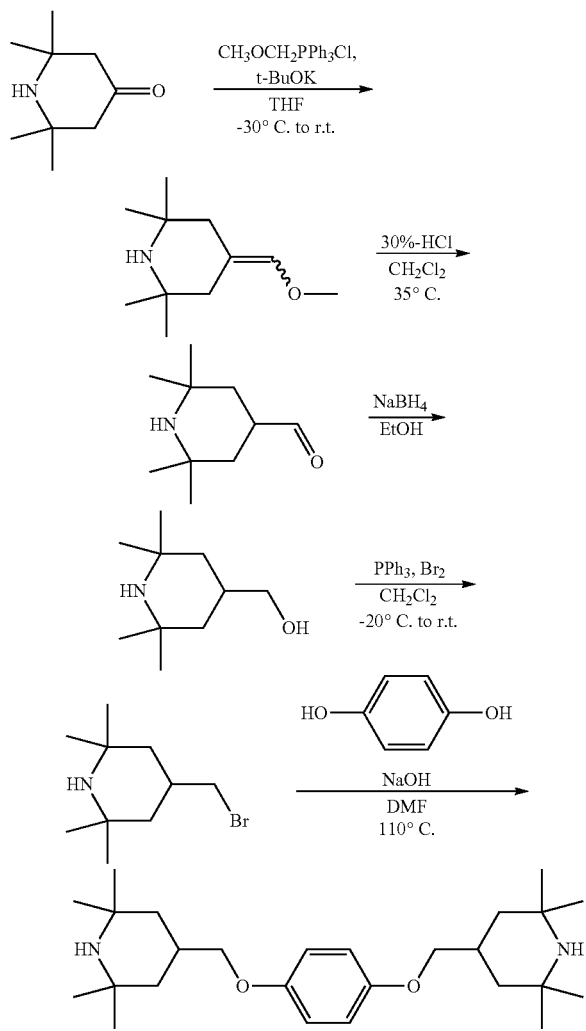

First Step:

Potassium t-butoxide (142 g, 1.25 mol) was added to a THF suspension of (methoxymethyl)triphenylphosphonium chloride (400 g, 1.17 mol) at 0° C. The resulting reaction mixture was stirred for 1 hour at 0° C., and then a THF solution of 2,2,6,6-tetramethylpiperidine-4-one (120 g, 0.77 mol) was added dropwise thereto. After stirring the reaction mixture at 5° C. for 2 hours, water was added thereto, and the mixture was quenched. The mixture was subjected to extraction with methyl t-butyl ether. A combined organic layer was concentrated. The obtained residue was subjected to extraction with hexane. Hexane was concentrated to obtain 4-(methoxymethylene)-2,2,6,6-tetramethylpiperidine (141 g, yield 99.9%).

Second Step:

A mixture of 4-(methoxymethylene)-2,2,6,6-tetramethylpiperidine (141 g, 0.77 mol) obtained in the first step and 30% hydrochloric acid (200 ml) was stirred in dichloromethane at 35° C. for 5 hours. An aqueous solution of sodium hydroxide was added thereto to achieve alkalinity (PH=9 to 10), and the mixture was subjected to extraction with dichloromethane. A combined organic layer was washed with water, and dried over anhydrous magnesium sulfate, and a solvent was distilled off to obtain 2,2,6,6-tetramethylpiperidine-4-carboaldehyde (113 g, 86.7%).

Third Step:

An ethanol solution of 2,2,6,6-tetramethylpiperidine-4-carboaldehyde (113 g, 0.67 mol) obtained in the second step was added to an ethanol solution of sodium borohydride (27 g, 0.71 mol) at room temperature, and the resulting mixture was stirred overnight. Acetone and water were added to the reaction solution, and the resulting mixture was quenched and subjected to extraction with ethyl acetate. A combined organic layer was washed with water, and dried over anhydrous magnesium sulfate, and a solvent was distilled off. The residue was washed with hexane to obtain (2,2,6,6-tetramethylpiperidine-4-yl)methanol (90 g, 78.4%).

Fourth Step:

Bromine (168 g, 1.05 mol) was added dropwise to a dichloromethane solution of triphenyl phosphine (276 g, 1.05 mol) at −20° C. After the resulting mixture was stirred at −10° C. for 30 minutes, the dichloromethane solution of (2,2,6,6-tetramethylpiperidine-4-yl)methanol (90 g, 0.53 mol) obtained in the third step was added dropwise thereto. The reaction solution was warmed to room temperature, and stirred for 1 hour, and quenched in sodium sulfite. Water was added thereto, and the mixture was subjected to extraction with dichloromethane. A combined organic layer was washed with water, and dried over anhydrous magnesium sulfate, and a solvent was distilled off. The obtained residue was subjected to extraction with hexane. An extraction liquid was concentrated, and purified by an alumina column to obtain 4-(bromomethyl)-2,2,6,6-tetramethylpiperidine (110 g, yield 88.6%).

Fifth Step:

A mixture of sodium hydroxide (5 g, 125 mmol) and hydroquinone (6 g, 54.5 mmol) was stirred in DMF at 110° C. for 1 hour. The DMF solution of 4-(bromomethyl)-2,2,6,6-tetramethylpiperidine (32 g, 137 mmol) obtained in the fourth step was added to the reaction mixture, and the resulting mixture was stirred at 110° C. for 2 hours. Water was added thereto, and the mixture was subjected to extraction with hexane. A combined organic layer was washed with water, and dried over anhydrous magnesium sulfate, and a solvent was distilled off. The residue was purified by an alumina column to obtain 1,4-bis((2,2,6,6-tetramethylpiperidine-4-yl)methoxybenzene) (16 g, 70.5%).

$^1$H-NMR (CDCl$_3$; δ ppm): 6.83 (s, 4H), 3.72 (d, 4H), 2.29 (ttt, 2H), 1.76 (dd, 4H), 1.70-1.53 (br, 2H), 1.23 (s, 12H), 1.13 (s, 12H), 0.90 (dd, 4H).
Compounds (No. 1) to (No. 44) and so forth shown below can be prepared according to the synthesis methods described in Examples 1 to 4.
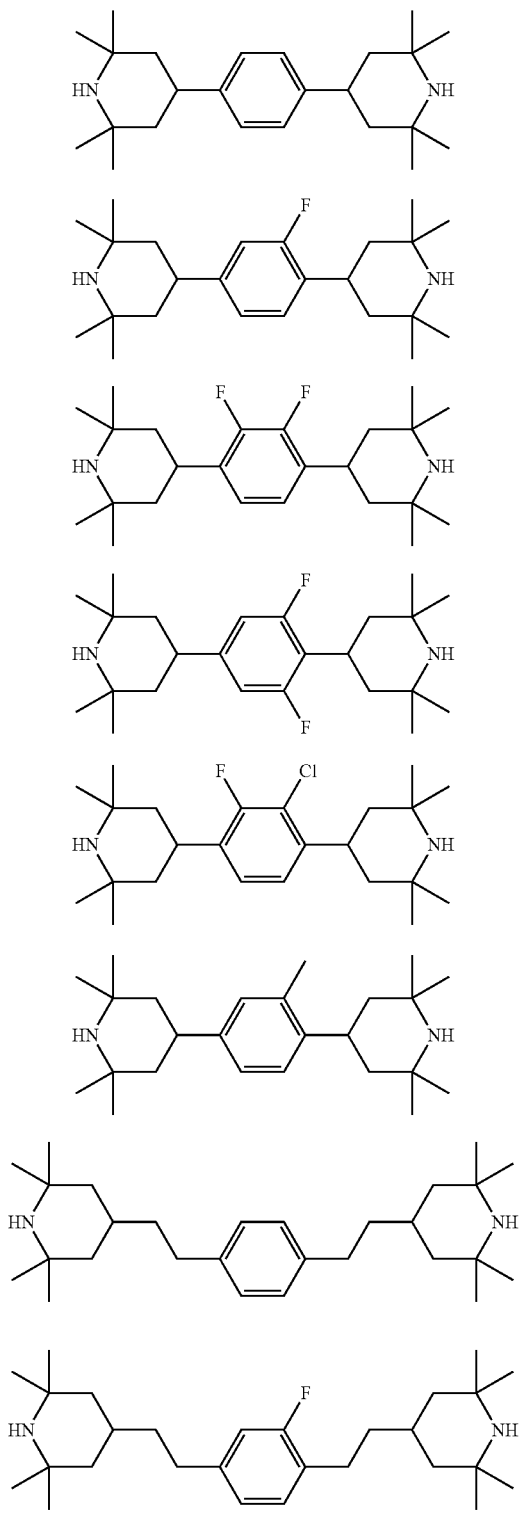
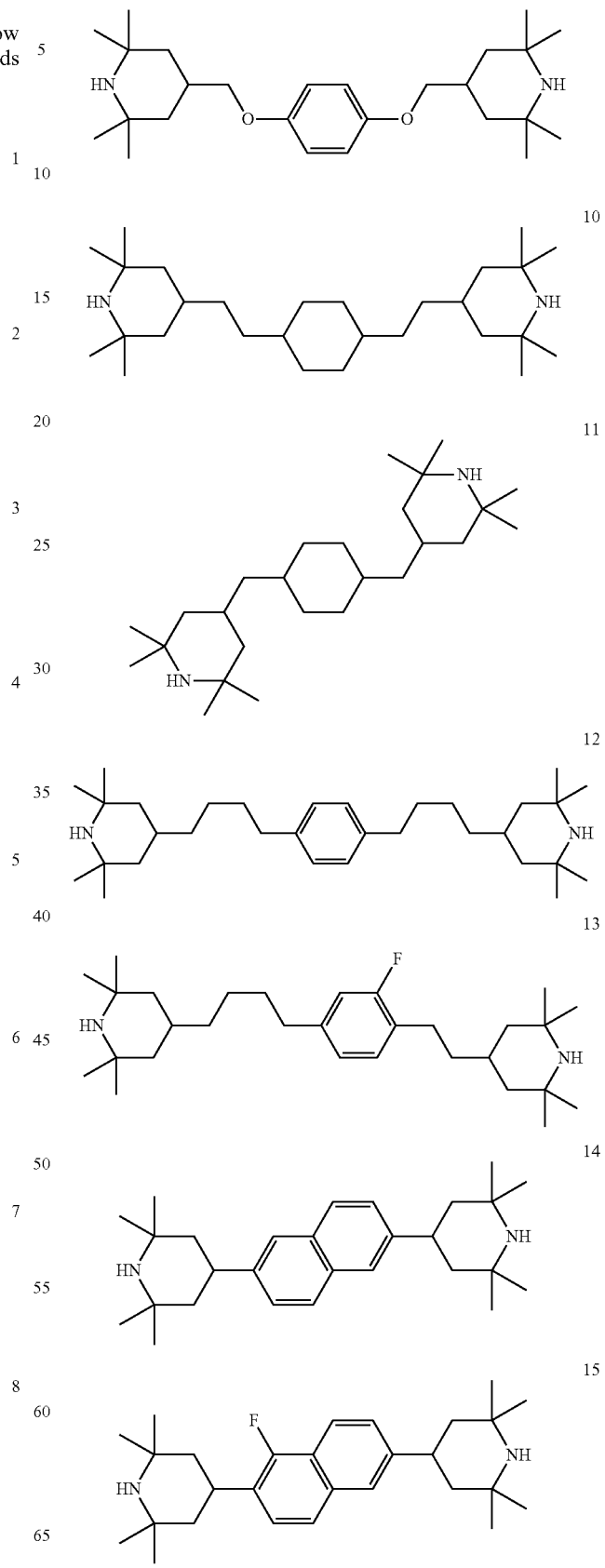

16
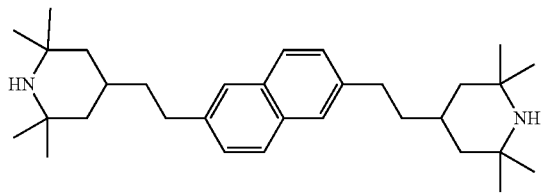
17
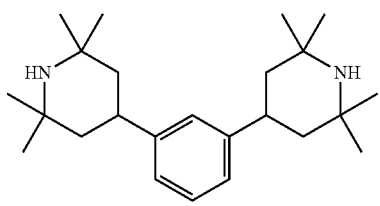
18
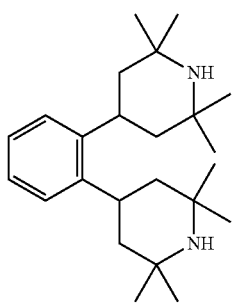
19
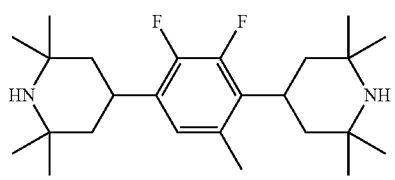
20
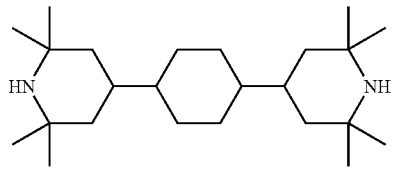
21
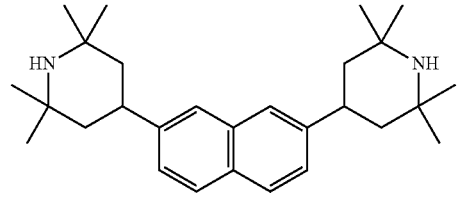
22
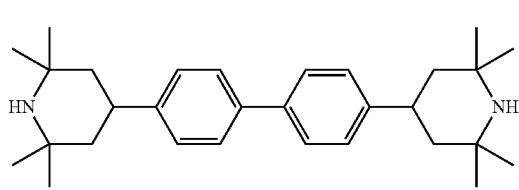
23
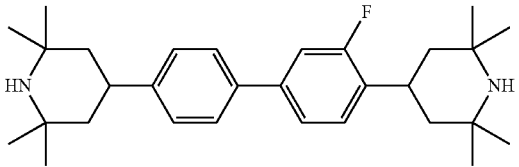
24
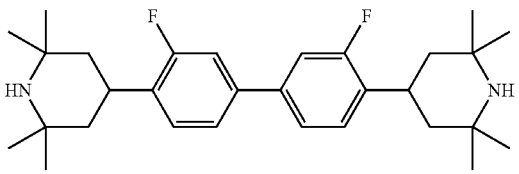
25
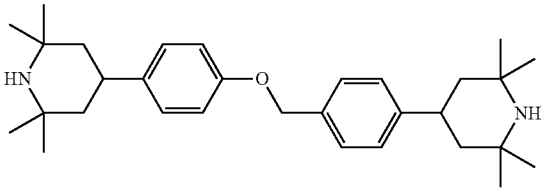
26
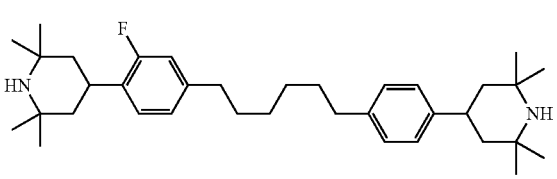
27
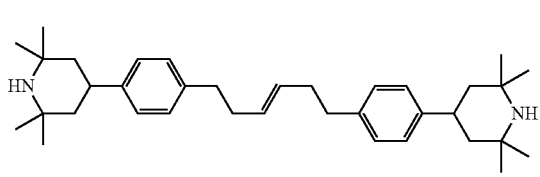
28
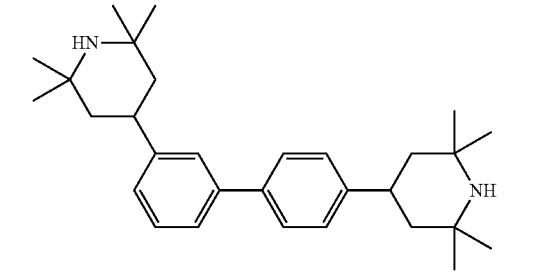
29
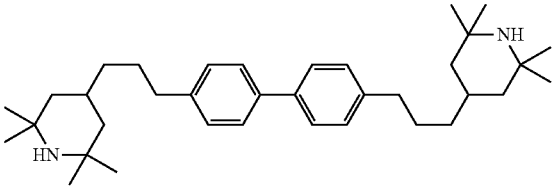

2. Example of Liquid Crystal Composition

A liquid crystal composition of the invention will be described in detail byway of Examples. The invention is not limited by the Examples. The invention includes a mixture of a composition in Example 5 and a composition in Example 6. The invention also includes a mixture in which at least two compositions in Examples were mixed. The compounds in Examples were described using symbols according to the definitions in Table 3 below. In Table 3, a configuration of 1,4-cyclohexylene is trans. A parenthesized number next to a symbolized compound in Examples corresponds to the number of a compound. A symbol (—) means any other liquid crystal compound. A content (percentage) of a liquid crystal compound is expressed in terms of weight percent (% by weight) based on the weight of the liquid crystal composition. Values of physical properties of the liquid crystal composition were summarized in a last part. The physical properties were measured according to the methods described above, and measured values were directly described (without extrapolation).

TABLE 1

| Method for Description of Compounds using Symbols |
|---|
| R—(A$_1$)—Z$_1$— ..... —Z$_n$—(A$_n$)—R' |

| 1) Left-terminal Group R— | Symbol |
|---|---|
| $C_nH_{2n+1}$— | n- |
| $C_nH_{2n+1}O$— | nO— |
| $C_mH_{2m+1}OC_nH_{2n}$— | mOn- |
| $CH_2$=CH— | V— |
| $C_nH_{2n+1}$—CH=CH— | nV— |
| $CH_2$=CH—$C_nH_{2n}$— | Vn- |
| $C_mH_{2m+1}$—CH=CH—$C_nH_{2n}$— | mVn- |
| $CF_2$=CH— | VFF— |
| $CF_2$=CH—$C_nH_{2n}$— | VFFn- |

| 2) Right—terminal Group —R' | Symbol |
|---|---|
| —$C_nH_{2n+1}$ | -n |
| —$OC_nH_{2n+1}$ | —On |
| —CH=$CH_2$ | —V |
| —CH=CH—$C_nH_{2n+1}$ | —Vn |
| —$C_nH_{2n}$—CH=$CH_2$ | -nV |
| —$C_nH_{2n}$—CH=CH—$C_mH_{2m+1}$ | -nVm |
| —CH=$CF_2$ | —VFF |
| —$COOCH_3$ | —EMe |
| —F | —F |
| —Cl | —CL |
| —$OCF_3$ | —OCF3 |
| —$CF_3$ | —CF3 |
| —CN | —C |

| 3) Bonding Group —Z$_n$— | Symbol |
|---|---|
| —$C_2H_4$— | 2 |
| —COO— | E |
| —CH=CH— | V |
| —C≡C— | T |
| —$CF_2O$— | X |
| —$CH_2O$— | 1O |

| 4) Ring Structure —A$_n$— | Symbol |
|---|---|
|  | H |
| 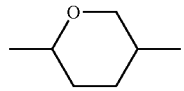 | Dh |
| 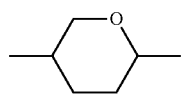 | dh |
|  | B |
| 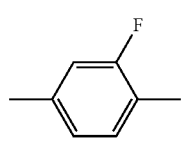 | B(F) |

TABLE 1-continued

Method for Description of Compounds using Symbols
R—(A$_1$)—Z$_1$—.....—Z$_n$—(A$_n$)—R'

 B(2F)

 B(F,F)

 B(2F,5F)

 G

5) Examples of Description

Example 1  3-HH-V1

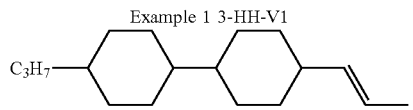

Example 2  3-BB(F)B(F,F)-F

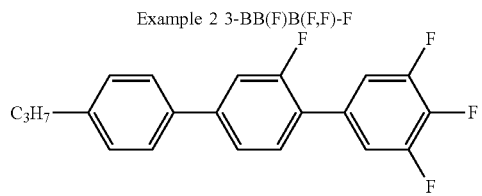

Example 3  4-BB(F)B(F,F)XB(F,F)-F

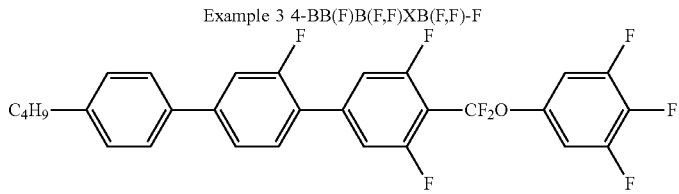

Example 4  V-HHB-1

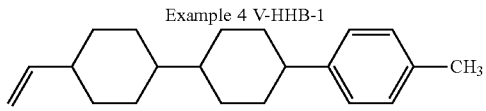

Example 5

Base liquid crystal M described below was prepared.

| | | |
|---|---|---|
| 3-HH-V | (2-1) | 30% |
| 3-HH-V1 | (2-1) | 5% |
| 3-HB-O1 | (2-5) | 2% |
| 3-HB-1 | (2-5) | 3% |
| 4-GHB(F,F)-F | (6-109) | 6% |

-continued

| | | |
|---|---|---|
| 3-HHXB(F,F)-F | (6-100) | 10% |
| 2-HHBB(F,F)-F | (7-6) | 4% |
| 3-HHBB(F,F)-F | (7-6) | 7% |
| 4-HHBB(F,F)-F | (7-6) | 5% |
| 5-HHBB(F,F)-F | (7-6) | 4% |
| 4-BB(F)B(F,F)XB(F,F)-F | (7-47) | 10% |
| 5-BB(F)B(F,F)XB(F,F)-F | (7-47) | 7% |
| 4-GB(F)B(F,F)XB(F,F)-F | (7-57) | 7% |

Characteristics of base liquid crystal M were as described below: NI=109.8° C.; Δn=0.109; Δε=11.2; γ1=114.6 mPa·s.

Measurement of Photolysis Product

Base liquid crystal M (3 mg) to which no light stabilizer was added was irradiated with ultraviolet light (30 mW/cm²) at 80° C. for 10 minutes. An amount of impurity (decomposition product) formed by a photoreaction was measured by gas chromatography. The amount of impurity formed was 4.17%. Next, compound (No. 1) of the invention was added to base liquid crystal M at a proportion of 1,000 ppm to obtain composition (X-1). The composition (3 mg) was irradiated with ultraviolet light under the same conditions. As amount of impurity formed was 3.29%. The amount of impurity formed decreased from 4.17% to 3.29% by adding compound (No. 1). If an amount of formation when no light stabilizer was added was taken as 100, a proportion of the amount of formation decreased to 79 by adding compound (No. 1). (See Table 2). The results show that compound (No. 1) is effective in preventing photolysis of the base liquid crystals caused by ultraviolet light.

Comparative Experiment 1

As comparative compounds, LA-77 made by ADEKA Corporation and bis(2,2,6,6-tetramethylpiperidine-4-yl) terephthalate were selected. The comparative compounds is different from the compound according to the invention in that the comparative compounds have an ester bond. First, LA-77 (1,000 ppm) made by ADEKA Corporation was added to base liquid crystal M to obtain composition (X-2). The composition (3 mg) was irradiated with ultraviolet light under the same conditions. An amount of impurity formed was 3.58%. A proportion of the amount of formation was 86 (see Table 2), and thus the composition was found to be effective in preventing photolysis. However, a degree of effectiveness was less in comparison with 79 in the case of compound (No. 1). Next, bis(2,2,6,6-tetramethylpiperidine-4-yl)terephthalate (1,000 ppm) was added to base liquid crystal M to obtain composition (X-3). The composition (3 mg) was irradiated with ultraviolet light under the same conditions. An amount of impurity formed was 3.64%. A proportion of the amount of impurity formed was 87, which was comparable to the amount in the case of composition (X-2).

From the results described above, the compound of the invention can be concluded to be significantly useful in preventing photolysis of the liquid crystal composition.

Compound No. 1

(X-1)

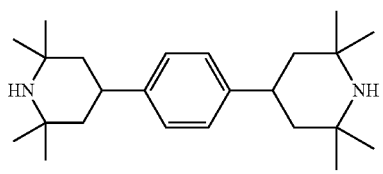

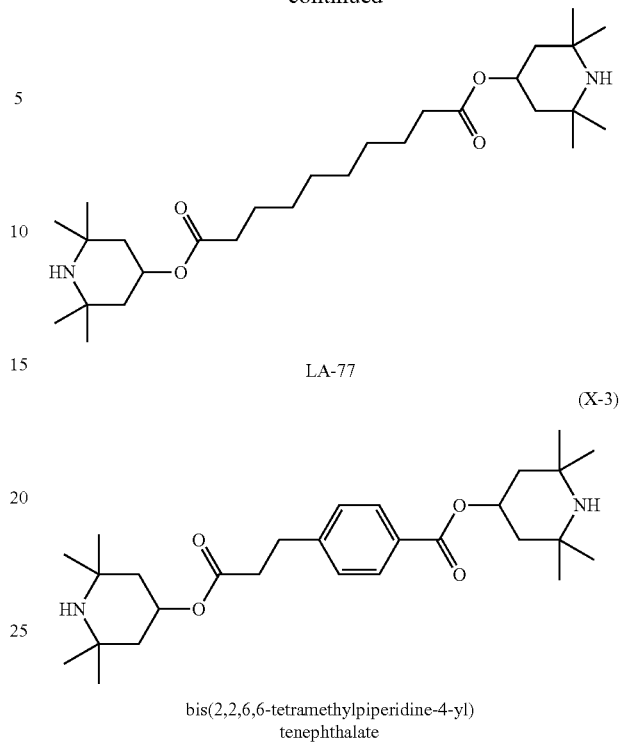

LA-77

(X-3)

bis(2,2,6,6-tetramethylpiperidine-4-yl) tenephthalate

TABLE 2

| | Impurity formed by irradiation with ultraviolet light | | | |
|---|---|---|---|---|
| Composition | Base liquid crystal M | X-1 (Example 5) | X-2 (Comparative Experiment 1) | X-3 (Comparative Experiment 1) |
| Amount of impurity formed (GC %) | 4.17 | 3.29 | 3.58 | 3.64 |
| Proportion of amount of formation | 100 | 79 | 86 | 87 |

Example 6

Composition (Y-1) was obtained by adding compound (No. 9) of the invention, at a proportion of 2,000 ppm, to base liquid crystal M in a manner similar to the operation in Example 5. The composition (3 mg) was irradiated with ultraviolet light under the same conditions. An amount of impurity formed was 2.06%. Composition (Y-2) was obtained by adding compound (No. 22), at a proportion of 2,000 ppm, to base liquid crystal M. The composition (3 mg) was irradiated with ultraviolet light under the same conditions. An amount of impurity formed was 2.79%. Composition (Y-3) was obtained by adding compound (No. 23), at a proportion of 2,000 ppm, to base liquid crystal M. The composition (3 mg) was irradiated with ultraviolet light under the same conditions. An amount of impurity formed was 2.89%.

Comparative Experiment 2

As a comparative compound, composition (Y-4) was obtained by adding LA-77 (2,000 ppm) to base liquid crystal M. The composition (3 mg) was irradiated with ultraviolet light under the same conditions. An amount of impurity formed was 3.11%.

From the results described above, the compound according to the invention can be concluded to be significantly useful in preventing photolysis of the liquid crystal composition.

Compound No. 8

(Y-1)

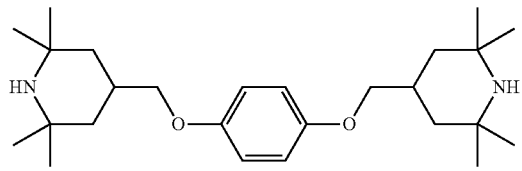

Compound No. 22

(Y-2)

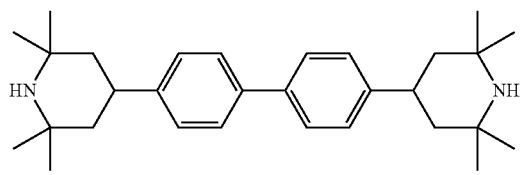

Compound No. 23

(Y-3)

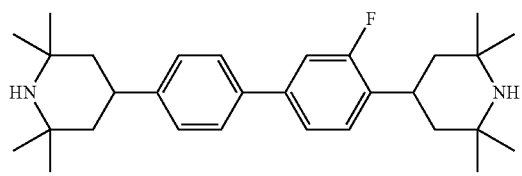

LA-77

TABLE 3

| Impurity formed by irradiation of ultraviolet light | | | | | |
|---|---|---|---|---|---|
| Composition | Base liquid crystal M | Y-1 (Example 6) | Y-2 (Example 6) | Y-3 (Example 6) | Y-4 (Comparative Experiment 2) |
| Amount of Impurity (GC %) | 4.17 | 2.06 | 2.79 | 2.89 | 3.11 |
| Proportion of amount of formation | 100 | 49 | 67 | 69 | 75 |

Example 7

| 3-HHXB(F,F)-F | (6-100) | 13% |
|---|---|---|
| 2-HHBB(F,F)-F | (7-6) | 4% |
| 3-HHBB(F,F)-F | (7-6) | 5% |
| 4-HHBB(F,F)-F | (7-6) | 4% |
| 5-HHBB(F,F)-F | (7-6) | 4% |
| 4-GB(F)B(F,F)XB(F,F)-F | (7-57) | 7% |
| 3-BB(F)B(F,F)XB(F)-F | (7-46) | 4% |
| 3-BB(F)B(F,F)XB(F,F)-F | (7-47) | 3% |
| 4-BB(F)B(F,F)XB(F,F)-F | (7-47) | 8% |
| 5-BB(F)B(F,F)XB(F,F)-F | (7-47) | 6% |
| 3-HH-V | (2-1) | 30% |
| 4-HH-V1 | (2-1) | 5% |
| 7-HB-1 | (2-5) | 3% |
| 3-HHB-O1 | (3-1) | 4% |

To the composition described above, compound (No. 1) was added at a proportion of 0.1% by weight.
NI=107.2° C.; Δn=0.113; Δε=11.0; η=16.0 mPa·s.

Example 8

| 3-HHXB(F,F)-F | (6-100) | 9% |
|---|---|---|
| 4-GHB(F,F)-F | (6-109) | 5% |
| 2-HHBB(F,F)-F | (7-6) | 4% |
| 3-HHBB(F,F)-F | (7-6) | 6% |
| 4-HHBB(F,F)-F | (7-6) | 5% |
| 4-GB(F)B(F,F)XB(F,F)-F | (7-57) | 7% |
| 4-BB(F)B(F,F)XB(F,F)-F | (7-47) | 9% |
| 5-BB(F)B(F,F)XB(F,F)-F | (7-47) | 7% |
| 3-HHB-CL | (6-1) | 3% |
| 3-HH-V | (2-1) | 29% |
| 3-HH-VFF | (2-1) | 4% |
| 3-HB-O2 | (2-5) | 3% |
| 3-HHB-3 | (3-1) | 3% |
| 5-HBB-2 | (3-4) | 3% |
| 3-HBBH-1O1 | (4-1) | 3% |

To the composition described above, compound (No. 23) was added at a proportion of 0.05% by weight.
NI=109.4° C.; Δn=0.112; Δε=10.4; η=15.5 mPa·s.

Example 9

| 3-HHXB(F,F)-F | (6-100) | 11% |
|---|---|---|
| 3-HGB(F,F)-F | (6-103) | 3% |
| 4-GHB(F,F)-F | (6-109) | 10% |
| 3-BB(F,F)XB(F,F)-F | (6-97) | 9% |
| 2-HHBB(F,F)-F | (7-6) | 4% |
| 3-HHBB(F,F)-F | (7-6) | 5% |
| 4-HHBB(F,F)-F | (7-6) | 5% |
| 5-HHBB(F,F)-F | (7-6) | 5% |

| | | |
|---|---|---|
| 4-BB(F)B(F,F)XB(F,F)-F | (7-47) | 9% |
| 5-BB(F)B(F,F)XB(F,F)-F | (7-47) | 3% |
| 3-HH-V | (2-1) | 20% |
| 3-HH-V1 | (2-1) | 5% |
| 3-HHB-1 | (3-1) | 8% |
| 3-HBB-2 | (3-4) | 3% |

To the composition described above, compound (No. 1) was added at a proportion of 0.05% by weight.
NI=106.8° C.; Δn=0.109; Δε=11.3; η=20.1 mPa·s.

Example 10

| | | |
|---|---|---|
| 3-HHB(F,F)-F | (6-3) | 3% |
| 3-HHXB(F,F)-F | (6-100) | 13% |
| 3-HB(F)B(F,F)-F | (6-50) | 5% |
| 3-BB(F,F)XB(F,F)-F | (6-97) | 16% |
| 3-HHHB(F,F)-F | (7-6) | 3% |
| 4-GBB(F)B(F,F)-F | (7-55) | 3% |
| 3-HBBXB(F,F)-F | (7-31) | 8% |
| 3-HBB(F,F)XB(F,F)-F | (7-34) | 6% |
| 3-HH-V | (2-1) | 24% |
| 3-HH-V1 | (2-1) | 7% |
| V2-BB-1 | (2-8) | 3% |
| 3-HHEH-3 | (3-13) | 3% |
| 1-BB(F)B-2V | (3-6) | 3% |
| 5-HBB(F)B-2 | (4-5) | 3% |

To the composition described above, compound (No. 23) was added at a proportion of 0.1% by weight.
NI=85.0° C.; Δn=0.109; Δε=8.5; η=17.0 mPa·s.

Example 11

| | | |
|---|---|---|
| 3-HB-CL | (5-2) | 6% |
| 5-HXB(F,F)-F | (5-13) | 5% |
| 3-HHB(F,F)-F | (6-3) | 10% |
| 3-HHEB(F,F)-F | (6-12) | 9% |
| 3-HHXB(F,F)-F | (6-100) | 19% |
| 2-HBEB(F,F)-F | (6-39) | 3% |
| 3-HBEB(F,F)-F | (6-39) | 3% |
| 3-BBXB(F,F)-F | (6-91) | 3% |
| 3-BB(F,F)XB(F,F)-F | (6-97) | 7% |
| 3-dhBB(F,F)XB(F,F)-F | (7-50) | 4% |
| 3-BB(F)B(F,F)XB(F)B(F,F)-F | (—) | 3% |
| 3-HH-V | (2-1) | 7% |
| 3-HH-V1 | (2-1) | 10% |
| 5-HH-V | (2-1) | 7% |
| 3-HHEBH-3 | (4-6) | 4% |

To the composition described above, compound (No. 1) was added at a proportion of 0.04% by weight.
NI=78.8° C.; Δn=0.085; Δε=10.0; η=16.8 mPa·s.

Example 12

| | | |
|---|---|---|
| 3-GB(F,F)XB(F,F)-F | (6-113) | 4% |
| 3-BB(F)B(F,F)-CF3 | (6-69) | 3% |
| 3-BB(F,F)XB(F,F)-F | (6-97) | 16% |
| 3-HHB(F)B(F,F)-F | (7-9) | 4% |
| 3-HBBXB(F,F)-F | (7-31) | 10% |
| 4-GB(F)B(F,F)XB(F,F)-F | (7-57) | 4% |
| 5-GB(F)B(F,F)XB(F,F)-F | (7-57) | 4% |
| 4-BB(F)B(F,F)XB(F,F)-F | (7-47) | 7% |
| 3-HH-V | (2-1) | 25% |
| 3-HH-O1 | (2-1) | 3% |
| 1-BB-3 | (2-8) | 3% |
| V-HHB-1 | (3-1) | 11% |
| 5-B(F)BB-2 | (3-8) | 3% |
| 2-BB(F)B-3 | (3-6) | 3% |

To the composition described above, compound (No. 23) was added at a proportion of 0.07% by weight.
NI=73.9° C.; Δn=0.120; Δε=12.4; η=17.5 mPa·s.

Example 13

| | | |
|---|---|---|
| 3-HBB(F,F)-F | (6-24) | 4% |
| 3-GB(F)B(F,F)-F | (6) | 3% |
| 3-BB(F)B(F,F)-F | (6-69) | 6% |
| 3-BB(F,F)XB(F,F)-F | (6-97) | 18% |
| 3-HBBXB(F,F)-F | (7-31) | 3% |
| 3-BB(F)B(F,F)XB(F,F)-F | (7-47) | 3% |
| 4-BB(F)B(F,F)XB(F,F)-F | (7-47) | 7% |
| 4-BB(F,F)XB(F)B(F,F)-F | (7-56) | 3% |
| 3-HH-V | (2-1) | 29% |
| V-HHB-1 | (3-1) | 11% |
| 2-BB(F)B-2V | (3-6) | 4% |
| 3-HB(F)HH-5 | (4-7) | 3% |
| 5-HBBH-3 | (4-1) | 3% |
| 3-HB(F)BH-3 | (4-2) | 3% |

To the composition described above, compound (No. 1) was added at a proportion of 0.06% by weight.
NI=80.6° C.; Δn=0.124; Δε=9.9; η=20.6 mPa·s.

Example 14

| | | |
|---|---|---|
| 3-HHXB(F,F)-F | (6-100) | 10% |
| 4-GHB(F,F)-F | (6-109) | 10% |
| 3-BB(F,F)XB(F,F)-F | (6-97) | 6% |
| 2-HHBB(F,F)-F | (7-6) | 4% |
| 3-HHBB(F,F)-F | (7-6) | 6% |
| 4-HHBB(F,F)-F | (7-6) | 5% |
| 5-HHBB(F,F)-F | (7-6) | 5% |
| 3-GBB(F)B(F,F)-F | (7-55) | 3% |
| 4-BB(F)B(F,F)XB(F,F)-F | (7-47) | 8% |
| 5-BB(F)B(F,F)XB(F,F)-F | (7-47) | 3% |
| 3-HH-V | (2-1) | 19% |
| 2-HH-3 | (2-1) | 4% |
| 3-HH-4 | (2-1) | 3% |
| V2-BB-1 | (2-8) | 6% |
| 3-HHB-1 | (3-1) | 5% |
| 5-HBB(F)B-3 | (4-5) | 3% |

To the composition described above, compound (No. 23) was added at a proportion of 0.12% by weight.
NI=107.1° C.; Δn=0.115; Δε=10.6; η=19.2 mPa·s.

Example 15

| | | |
|---|---|---|
| 5-HB-CL | (5-2) | 3% |
| 7-HB(F)-F | (5-3) | 7% |
| 3-HH-4 | (2-1) | 12% |
| 3-HH-EMe | (2-2) | 20% |
| 3-HHEB-F | (6-10) | 8% |
| 5-HHEB-F | (6-10) | 8% |
| 3-HHEB(F,F)-F | (6-12) | 10% |
| 4-HHEB(F,F)-F | (6-12) | 5% |
| 4-HGB(F,F)-F | (6-103) | 5% |
| 5-HGB(F,F)-F | (6-103) | 6% |
| 2-H2GB(F,F)-F | (6-106) | 4% |

| | | |
|---|---|---|
| 3-H2GB(F,F)-F | (6-106) | 5% |
| 5-GHB(F,F)-F | (6-109) | 7% |

To the composition described above, compound (No. 22) was added at a proportion of 0.1% by weight.
NI=79.2° C.; Δn=0.063; Δε=5.7; η=19.2 mPa·s.

Example 16

| | | |
|---|---|---|
| 5-HB(F)B(F,F)XB(F,F)-F | (7-41) | 5% |
| 3-BB(F)B(F,F)XB(F,F)-F | (7-47) | 3% |
| 4-BB(F)B(F,F)XB(F,F)-F | (7-47) | 7% |
| 5-BB(F)B(F,F)XB(F,F)-F | (7-47) | 3% |
| 3-HH-V | (2-1) | 38% |
| 3-HH-V1 | (2-1) | 7% |
| 3-HHEH-5 | (3-13) | 3% |
| 3-HHB-1 | (3-1) | 4% |
| V-HHB-1 | (3-1) | 5% |
| V2-BB(F)B-1 | (3-6) | 5% |
| 1V2-BB-F | (5-1) | 3% |
| 3-BB(F,F)XB(F,F)-F | (6-97) | 14% |
| 3-HHBB(F,F)-F | (7-6) | 3% |

To the composition described above, compound (No. 22) was added at a proportion of 0.08% by weight.
NI=80.3° C.; Δn=0.107; Δε=7.2; η=14.0 mPa·s.

Example 17

| | | |
|---|---|---|
| 5-HB-CL | (5-2) | 5% |
| 7-HB(F)-F | (5-3) | 7% |
| 3-HH-4 | (2-1) | 10% |
| 3-HH-EMe | (2-2) | 20% |
| 3-HHEB-F | (6-10) | 8% |
| 5-HHEB-F | (6-10) | 8% |
| 3-HHEB(F,F)-F | (6-12) | 10% |
| 4-HHEB(F,F)-F | (6-12) | 5% |
| 4-HGB(F,F)-F | (6-103) | 5% |
| 5-HGB(F,F)-F | (6-103) | 6% |
| 2-H2GB(F,F)-F | (6-106) | 4% |
| 3-H2GB(F,F)-F | (6-106) | 5% |
| 5-GHB(F,F)-F | (6-109) | 7% |

To the composition described above, compound (No. 9) was added at a proportion of 0.1% by weight.
NI=77.8° C.; Δn=0.064; Δε=5.8; η=19.3 mPa·s.

Example 18

| | | |
|---|---|---|
| 5-HB(F)B(F,F)XB(F,F)-F | (7-41) | 5% |
| 3-BB(F)B(F,F)XB(F,F)-F | (7-47) | 3% |
| 4-BB(F)B(F,F)XB(F,F)-F | (7-47) | 7% |
| 5-BB(F)B(F,F)XB(F,F)-F | (7-47) | 3% |
| 3-HH-V | (2-1) | 39% |
| 3-HH-V1 | (2-1) | 6% |
| 3-HHEH-5 | (3-13) | 3% |
| 3-HHB-1 | (3-1) | 5% |
| V-HHB-1 | (3-1) | 4% |
| V2-BB(F)B-1 | (3-6) | 5% |
| 1V2-BB-F | (5-1) | 3% |
| 3-BB(F,F)XB(F,F)-F | (6-97) | 14% |
| 3-HHBB(F,F)-F | (7-6) | 3% |

To the composition described above, compound (No. 9) was added at a proportion of 0.06% by weight.
NI=80.0° C.; Δn=0.106; Δε=7.2; η=14.1 mPa·s.

INDUSTRIAL APPLICABILITY

Compound (1) is effective in preventing photolysis of a liquid crystal composition, and has high solubility in the liquid crystal composition. The liquid crystal composition containing compound (1) satisfies at least one of characteristics such as a high maximum temperature, a low minimum temperature, a small viscosity, a suitable optical anisotropy, a large dielectric anisotropy, a suitable elastic constant and a large specific resistance. The composition is stable to light. A liquid crystal display device including the composition has characteristics such as a short response time, a large voltage holding ratio, a large contrast ratio and a long service life, and thus can be used for a liquid crystal projector, a liquid crystal television and so forth.

What is claimed is:

1. A compound, represented by formula (1):

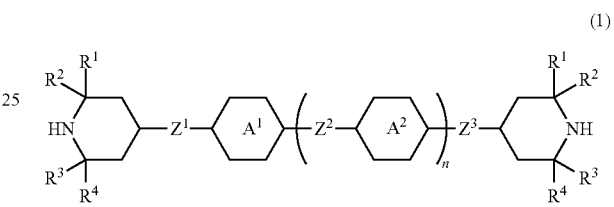

wherein, in formula (1),
$R^1$, $R^2$, $R^3$ and $R^4$ are independently hydrogen or alkyl having 1 to 4 carbons;
ring $A^1$ and ring $A^2$ are independently 1,4-cyclohexylene, 1,4-cyclohexenylene, 1,2-phenylene, 1,3-phenylene, 1,4-phenylene, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, decahydronaphthalene-2,6-diyl, dihydropyrane-2,5-diyl, tetrahydropyran-2,5-diyl, 1,3-dioxane-2,5-diyl, pyrimidine-2,5-diyl or pyridine-2,5-diyl, and in the rings, at least one piece of hydrogen may be replaced by halogen, alkyl having 1 to 5 carbons, alkoxy having 1 to 5 carbons, or alkyl having 1 to 5 carbons in which at least one piece of hydrogen is replaced by halogen;
$Z^1$ and $Z^3$ are independently a single bond, —O—, or alkylene having 2 to 10 carbons, and in the alkylene, at least one —CH$_2$— may be replaced by —O—, at least one —CH$_2$—CH$_2$— may be replaced by —CH=CH— or —C≡C—, and at least one hydrogen may be replaced by fluorine,
$Z^2$ is a single bond, or alkylene having 1 to 10 carbons, and in the alkylene, at least one —CH$_2$— may be replaced by —O—, at least one —CH$_2$—CH$_2$— may be replaced by —CH=CH— or —C≡C—, and at least one hydrogen may be replaced by fluorine; and
n is 0, 1 or 2.

2. The compound according to claim 1, wherein, in formula (1) described in claim 1,
$R^1$, $R^2$, $R^3$ and $R^4$ are independently hydrogen or alkyl having 1 to 4 carbons;
ring $A^1$ and ring $A^2$ are independently 1,4-cyclohexylene, 1,4-cyclohexenylene, 1,4-phenylene, 1,4-phenylene in which at least one hydrogen is replaced by fluorine, tetrahydropyran-2,5-diyl, pyridine-2,5-diyl, 1,3-dioxane-2,5-diyl, naphthalene-2,6-diyl, naphthalene-2,6- diyl in which at least one hydrogen is replaced by fluorine, or decahydronaphthalene-2,6-diyl;

$Z^1$ and $Z^3$ are independently a single bond, —O—, or alkylene having 2 to 10 carbons, and in the alkylene, at least one —CH$_2$— may be replaced by —O— and at least one —CH$_2$—CH$_2$— may be replaced by —CH═CH—, $Z^2$ is a single bond, or alkylene having 1 to 10 carbons, and in the alkylene, at least one —CH$_2$— may be replaced by —O—, at least one —CH$_2$—CH$_2$— may be replaced by —CH═CH—; and n is 0, 1 or 2.

3. The compound according to claim 1, wherein, in formula (1) described in claim 1, $R^1$, $R^2$, $R^3$ and $R^4$ are independently alkyl having 1 to 4 carbons;

ring $A^1$ and ring $A^2$ are independently 1,4-cyclohexylene, 1,4-cyclohexenylene, 1,4-phenylene, 1,4-phenylene in which at least one hydrogen is replaced by fluorine, naphthalene-2,6-diyl, or naphthalene-2,6-diyl in which at least one hydrogen is replaced by fluorine;

$Z^1$ and $Z^3$ are independently a single bond, —O—, or alkylene having 2 to 10 carbons, and in the alkylene, at least one —CH$_2$— may be replaced by —O— and at least one —CH$_2$—CH$_2$— may be replaced by —CH═CH—, $Z^2$ is a single bond, or alkylene having 1 to 10 carbons, and in the alkylene, at least one —CH$_2$— may be replaced by —O—, at least on —CH$_2$—CH$_2$— may be replaced by —CH═CH—; and n is 0, 1 or 2.

4. The compound according to claim 1, wherein, in formula (1) described in claim 1, $R^1$, $R^2$, $R^3$ and $R^4$ are methyl;

ring $A^1$ and ring $A^2$ are independently 1,4-cyclohexylene, 1,4-phenylene, or 1,4-phenylene in which at least one hydrogen is replaced by fluorine;

$Z^1$ and $Z^3$ are single bonds, and $Z^2$ is a single bond, —CH$_2$—, —CH$_2$CH$_2$—, —CH═CH—, —OCH$_2$— or —CH$_2$O—; and n is 0 or 1.

5. The compound according to claim 1, wherein, in formula (1) described in claim 1, $R^1$, $R^2$, $R^3$ and $R^4$ are methyl;

ring $A^1$ and ring $A^2$ are independently 1,4-phenylene or 2-fluoro-1,4-phenylene;

$Z^1$, $Z^2$ and $Z^3$ are single bonds; and n is 0 or 1.

6. A liquid crystal composition, containing at least one compound according to claim 1.

7. The liquid crystal composition according to claim 6, further containing at least one compound selected from the group of compounds represented by formulas (2) to (4):

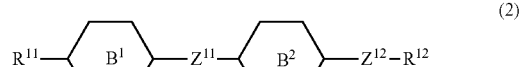

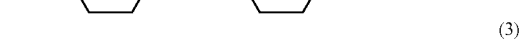

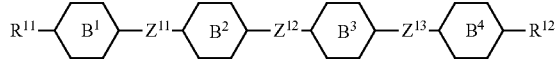

wherein, in formulas (2) to (4), $R^{11}$ and $R^{12}$ are independently alkyl having 1 to 10 carbons or alkenyl having 2 to 10 carbons, and in the alkyl or the alkenyl, at least one —CH$_2$— may be replaced by —O—, and at least one hydrogen may be replaced by fluorine;

ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and $Z^{11}$, $Z^{12}$ and $Z^{13}$ are independently a single bond, —CH$_2$CH$_2$—, —CH═CH—, —C≡C— or —COO—.

8. The liquid crystal composition according to claim 6, further containing at least one compound selected from the group of compounds represented by formulas (5) to (7):

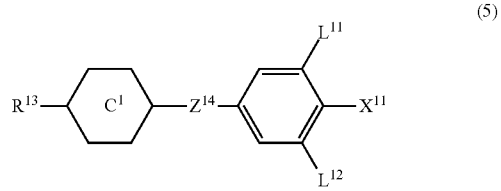

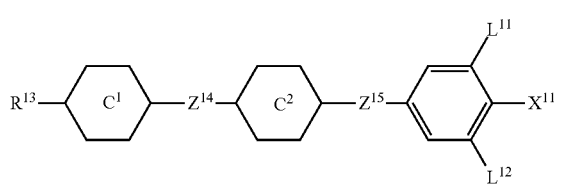

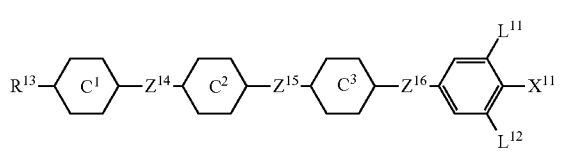

wherein, in formulas (5) to (7), $R^{13}$ is alkyl having 1 to 10 carbons or alkenyl having 2 to 10 carbons, and in the alkyl and the alkenyl, at least one —CH$_2$— may be replaced by —O—, and at least one hydrogen may be replaced by fluorine;

$X^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;

ring $C^1$, $C^2$ and $C^3$ are independently 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;

$Z^{14}$, $Z^{15}$ and $Z^{16}$ are independently a single bond, —CH$_2$CH$_2$—, —CH═CH—, —C≡C—, —COO—, —CF$_2$O—, —OCF$_2$—, —CH$_2$O— or —(CH$_2$)$_4$—; and $L^{11}$ and $L^{12}$ are independently hydrogen or fluorine.

9. The liquid crystal composition according to claim 6, further containing at least one compound selected from the group of compounds represented by formula (8):

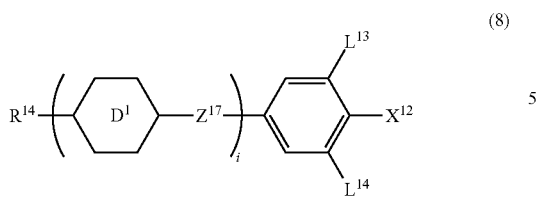

(8)

wherein, in formula (8),
$R^{14}$ is alkyl having 1 to 10 carbons or alkenyl having 2 to 10 carbons, and in the alkyl and the alkenyl, at least one —$CH_2$— may be replaced by —O—, and at least one hydrogen may be replaced by fluorine;
$X^{12}$ is —C≡N or —C≡C—C≡N;
ring $D^1$ is 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;
$Z^{17}$ is a single bond, —$CH_2CH_2$—, —C≡C—, —COO—, —$CF_2O$—, —$OCF_2$— or —$CH_2O$—;
$L^{13}$ and $L^{14}$ are independently hydrogen or fluorine; and
i is 1, 2, 3 or 4.

10. The liquid crystal composition according to claim 6, further containing at least one of a polymerizable compound, a polymerization initiator, a polymerization inhibitor, an optically active compound, an antioxidant, an ultraviolet light absorber, a light stabilizer, a heat stabilizer and an antifoaming agent.

11. A liquid crystal display device, including at least one liquid crystal composition according to claim 6.

* * * * *